United States Patent [19]
Klein et al.

[11] Patent Number: 5,998,169
[45

Figure 1A:
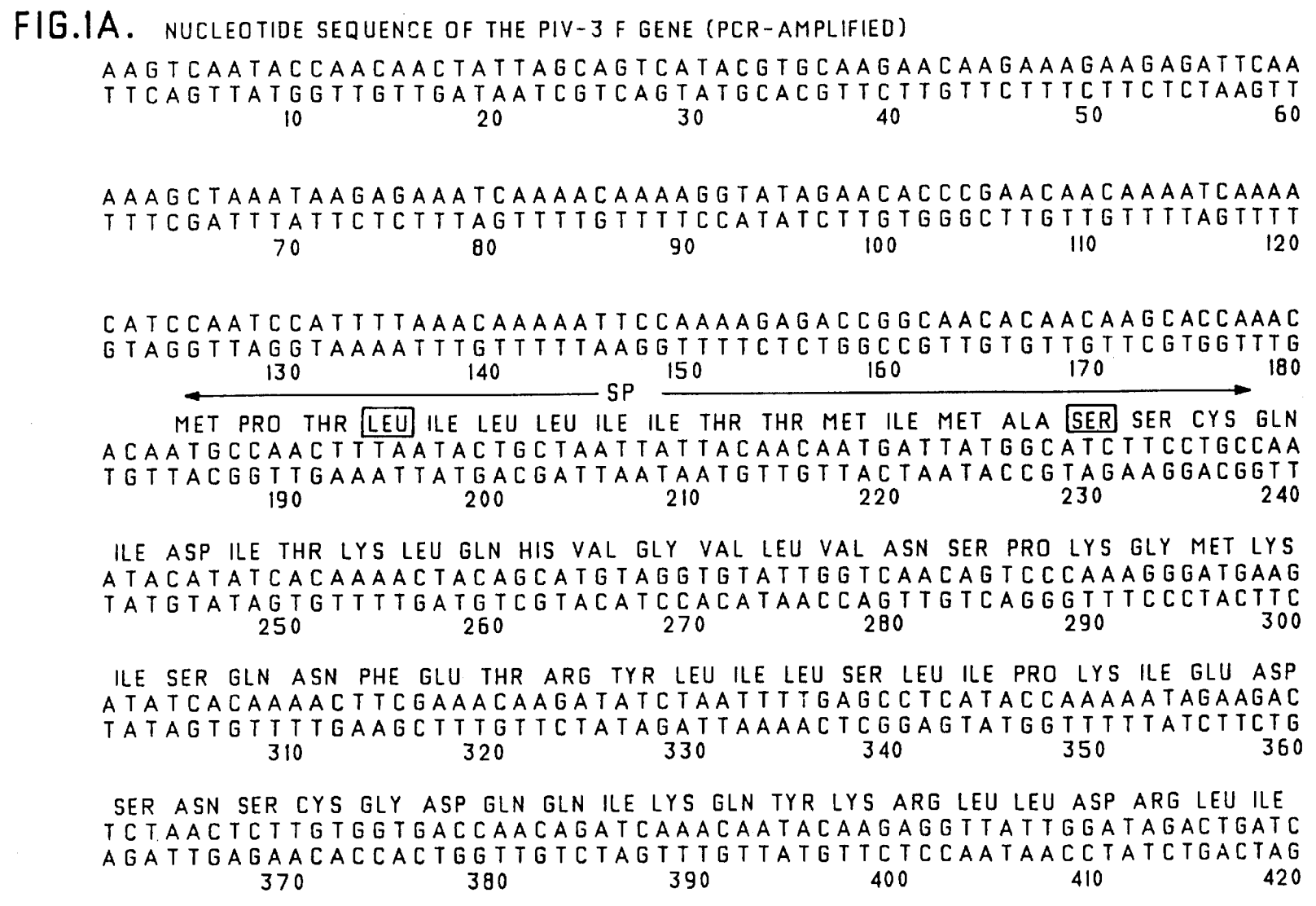

FIG.1A. NUCLEOTIDE SEQUENCE OF THE PIV-3 F GENE (PCR-AMPLIFIED)

```
AAGT

FIG.1B.

```
          ILE PRO LEU TYR ASP GLY LEU ARG LEU GLN LYS ASP VAL ILE VAL THR  ASN GLN GLU SER
          ATCCCTCTATATGATGGATTAAGATTACAGAAAGATGTGATAGTAACCAATCAAGAATCC
          TAGGGAGATATACTACCTAATTCTAATGTCTTTCTACACTATCATTGGTTAGTTCTTAGG
                   430            440            450            460            470            480
                                                         F2-F1 CLEAVAGE SITE
          ASN GLU ASN THR ASP PRO ARG THR ARG ARG SER PHE GLY GLY VAL ILE GLY THR ILE ALA
          AATGAAAACACTGATCCCAGAACAAGACGATCCTTTGGAGGGTAATTGGAACCATTGCT
          TTACTTTTGTGACTAGGGTCTTGTTCTGCTAGGAAACCTCCCATTAACCTTGGTAACGA
                   490            500            510            520            530            540

LEU GLY VAL ALA THR SER ALA GLN ILE THR ALA ALA VAL ALA LEU VAL GLU ALA LYS GLN
          CTGGGAGTAGCAACCTCAGCACAAATTACAGCGGCAGTTGCTCTGGTTGAAGCCAAGCAG
          GACCCTCATCGTTGGAGTCGTGTTTAATGTCGCCGTCAACGAGACCAACTTCGGTTCGTC
                   550            560            570            580            590            600

ALA LYS SER ASP ILE GLU LYS LEU LYS GLU ALA ILE ARG ASP THR ASN LYS ALA VAL GLN
          GCAAAATCACACGTGATATCGAAAAACTCAAAGAAGCAATCAGGGACACAAACAAGGCAGTGCAG
          CGTTTTAGTGTGTAGCTTTTGAGTTTCTTCGTTAGTCCCTGTGTTTGTTCGTCACGTC
                   610            620            630            640            650            660

SER VAL GLN SER SER ILE GLY ASN LEU ILE VAL ALA ILE LYS SER VAL GLN ASP TYR VAL
          TCAGTTCAGAGCTCTATAGGAAATTTAATAGTAGCAATTAAATCAGTCCAAGATTATGTC
          AGTCAAGTCTCGAGATATCCTTTAAATTATCATCGTTAATTTAGTCAGGTTCTAATACAG
                   670            680            690            700            710            720

ASN ASN GLU ILE VAL PRO SER ILE ALA ARG LEU GLY CYS GLU ALA ALA GLY LEU GLN LEU
          AACAACGAAATCGTGCCATCGATTGCTAGACTGCTAGGTTGTGAAGCAGGACTTCAATTA
          TTGTTGCTTTAGCACGGTAGCTAACGATCTGATCGATCCAACACTTCGTCCTGAAGTTAAT
                   730            740            750            760            770            780

GLY ILE ALA LEU THR GLN HIS TYR SER GLU LEU THR ASN ILE PHE GLY ASP ASN ILE GLY
          GGAATTGCATTAACACAGCATTACTCAGAATTAACAACATATTTGGTGATAACATAGGA
          CCTTAACGTAATTGTGTCGTAATGAGTCTTAATTGTTGTATAAACCACTATTGTATCCT
                   790            800            810            820            830            840
```

FIG. 1C.

```
    SER LEU GLN GLU LYS GLY ILE LYS LEU GLN GLY ILE ALA SER LEU TYR ARG THR ASN ILE
    TCGTTACAAGAAAAAGGAATAAATTACAAGGTATAGCATCATTATACCGCACAAATATC
    AGCAATGTTCTTTTTCCTTATTTTAATGTTCCATATCGTAGTAATATGGCGTGTTTATAG
                    850                 860                 870                 880                 890                 900

THR GLU ILE PHE THR THR THR SER THR VAL ASP LYS TYR ASP ILE TYR ASP LEU LEU PHE THR
    ACAGAAATATTCACAACATCAACAGTTGATAAATATGATATATCTATGATCTATTATTACA
    TGTCTTTATAAGTGTTGTAGTTGTCAACTATTTATACTATATAGATACTAGATAATAATGT
                    910                 920                 930                 940                 950                 960

GLU SER ILE LYS VAL ARG VAL ILE ASP VAL ASP TYR ASN ASP TYR SER ILE THR LEU GLN
    GAATCAATAAAGGTGAGAGTTATAGATGTTGATTTGAATGATTACTCAATCACCCTCCAA
    CTTAGTTATTTCCACTCTCAATATCTACAACTAAACTTACTAATGAGTTAGTGGGAGGTT
                    970                 980                 990                 1000                1010                1020

VAL ARG LEU PRO LEU LEU THR ARG LEU LEU ASN THR GLN ILE TYR LYS VAL ASP SER ILE
    GTCAGACTCCCTTATTAACTAGGCTGCTGAACACTCAGATCTACAAAGTAGATTCCATA
    CAGTCTGAGGGAATAATTGATCCGACGACTTGTGAGTCTAGATGTTCATCTAAGGTAT
                    1030                1040                1050                1060                1070                1080

SER TYR ASN ILE GLN ASN ARG GLU TRP TYR ILE PRO LEU PRO SER HIS ILE MET THR LYS
    TCATATAATATCCAAAACAGAGAATGGTATATCCCTCTTCCCAGCCATATCATGACGAAA
    AGTATATTATAGGTTTTGTCTCTTACCATATAGGGAGAAGGGTCGGTATAGTACTGCTTT
                    1090                1100                1110                1120                1130                1140

GLY ALA PKE LEU GLY GLY ALA ASP VAL LYS GLU CYS ILE GLU ALA PHE SER SER TYR ILE
    GGGGCATTTCTAGGTGGAGCAGATGTCAAGGAATGTATAGAAGCATTCAGCAGTTATATA
    CCCCGTAAAGATCCACCTCGTCTACAGTTCCTTACACATATCTTCGTAAGTCGTCAATATAT
                    1150                1160                1170                1180                1190                1200

CYS PRO SER ASP PRO GLY PHE VAL LEU ASN HIS GLU KET GLU SER CYS LEU SER GLY ASN
    TGCCCTTCTGATCCAGGATTTGTACTAAACCATGAAATGGAGAGCTGCTTATCAGGAAAC
    ACGGGAAGACTAGGTCCTAAACATGATTTGGTACTTTACCTCTCGACGAATAGTCCTTTG
                    1210                1220                1230                1240                1250                1260
```

FIG.1D.

```
     ILE SER GLN CYS PRO ARG THR  THR  VAL  THR  SER ASP ILE VAL PRO ARG TYR ALA PHE VAL
     ATATCCCAATGTCCAAGAACCACGGTCACAGATCAGACATTGTTCCAAGATATGCATTCGTC
     TATAGGGTTACAGGTTCTTGGTGCCAGTGTCTAGTGTCTGTAACAAGGTTCTATACGTAAGCAG
          1270            1280            1290            1300            1310            1320

ASN GLY GLY VAL VAL ALA ASN CYS ILE THR THR THR CYS ASN GLY ILE  ASP  ASN
     AATGGAGGAGTGGTTGCAAACTGTATAACAACCACCTGTACATGCAACGGAATCGACAAT
     TTACCTCCTCACCAACGTTTGACATATTGTTGGTGGACATGTACGTTGCCTTAGCTGTTA
          1330            1340            1350            1360            1370            1380

ARG ILE ASN GLN PRO PRO ASP GLN GLY VAL LYS ILE ILE THR HIS LYS GLU CYS ASN THR
     AGAATCAATCAACCACCTGATCAAGGAGTAAAAATTATAACACATAAAGAATGTAATACA
     TCTTAGTTAGTTGGTGGACTAGTTCCTCATTTTTAATATTGTATTTCTTACATTATGT
          1390            1400            1410            1420            1430            1440

ILE GLY ILE ASN GLY MET LEU PHE ASN THR ASN LYS GLU GLY THR LEU ALA PHE TYR THR
     ATAGGTATCAACGGAATGCTGTTCAATACAAATAAAGAAGGAACTCTTGCATTCTACACA
     TATCCATAGTTGCCTTACGACAAGTTATGTTATTTCTTCCTTGAGAACGTAAGATGTGT
          1450            1460            1470            1480            1490            1500

PRO ASN ASP ILE THR LEU ASN ASN SER VAL ALA LEU ASP PRO ILE ASP ILE SER ILE GLU
     CCAAATGATATAACACTAAATAATTCTGTTGCACTTGATCCAATTGACATATCAATCGAG
     GGTTTACTATATTGTGATTTATTAAGACAACGTGAACTAGGTTAACTGTATAGTTAGCTC
          1510            1520            1530            1540            1550            1560

LEU ASN LYS ALA LYS SER ASP LEU GLU GLU SER LYS GLU TRP ILE ARG ARG SER ASN GLN
     CTTAACAAAGCCAAATCAGATCTAGAAGAATCAAAAGAATGGATAAGAAGGTCAAATCAA
     GAATTGTTTCGGTTTAGTCTAGATCTTCTTAGTTTTCTTACCTATTCTTCCAGTTAGTT
          1570            1580            1590            1600            1610            1620
                                                                                    ├── TM
     LYS LEU ASP SER ILE GLY ASN TRP HIS GLN SER SER THR THR ILE ILE  ILE  LEU ILE
     AAACTAGATTCTATTGGAAACTGGCATCAGCACTACAATCATAATTATTTAATA
     TTTGATCTAAGATAACCTTTGACCGTAGTTAGATCGTGATGTTAGTATTAATAAAATTAT
          1630            1640            1650            1660            1670            1680
                                                                                    ↑
```

FIG.1E

MET ILE ILE ILE LEU PHE ILE ILE ASN VAL THR ILE ILE ALA [ILE] LYS TYR TYR
ATGATCATTATTATTGTTTATAATTAATGTAACGATAATTACAATTGCAATTAAGTATTAC
TACTAGTAATAATAACAAATATTAATTACATTGCTATTAATGTTAACGTTAATTCATAATG
   1690     1700     1710     1720     1730     1740

ARG ILE GLN LYS ARG ASN ARG VAL ASP GLN ASN ASP LYS PRO TYR VAL LEU [THR] ASN LYS
AGAATTCAAAAGAGAAATCGAGTGGATCAAATGACAAGCCATATGTACTAACAAACAAA
TCTTAAGTTTTCTCTTTAGCTCACCTAGTTTACTGTTCGGTATACATGATTGTTTGTTT
   1750     1760     1770     1780     1790     1800

TGACATATCTATAGATCATTAGATATTAAAATTATAAAAAACTT
ACTGTATAGATATCTAGTAATCTATAATTTAATATTTTTGAA
   1810     1820     1830     1840

NUCLEOTIDE SEQUENCE OF THE PIV-3 F GENE. THE cDNA SEQUENCE
IS SHOWN IN THE PLUS (mRNA) STRAND SENSE IN THE 5' TO 3'
DIRECTION. THE SIGNAL PEPTIDE (SP) AND THE TRANSMEMBRANE (TM)
ANCHOR DOMAIN ARE UNDERLINED. THE PREDICTED F2-F1 CLEAVAGE SITE IS
INDICATED BY THE ARROW (↓). AMINO ACIDS DIFFERING FROM THE
PUBLISHED PRIMARY SEQUENCE OF THE PROTEIN ENCODED BY THE PIV-3 F
GENE ARE BOXED.

FIG.3A. NUCLEOTIDE SEQUENCE OF THE PIV-3 HN GENE.

```
                                    MET GLU TYR TRP LYS HIS THR ASN HIS GLY LYS ASP ALA GLY
5' AGACAAATCCAAATTCGAGATGGAATACTGGAAGCATACCAATCACGGAAAGGATGCTGG 60
   TCTGTTTAGGTTTAAGCTCTACCTTATGACCTTCGTATGGTTAGTGCCTTTCCTACGACC
            10          20          30          40          50
                                                                    ←—TM——
   ASN GLU LEU GLU THR SER MET ALA THR [ASN] GLY ASN LYS [LEU] THR ASN LYS ILE THR TYR
   AATGAGCTGGAGACGTCCATGGCTACTAATGGCAACAAGCTCACCAATAAGATAACATA 120
   TTACTCGACCTCTGCAGGTACCGATGATTACCGTTGTTCGAGTGGTTATTCTATTGTAT
            70          80          90         100         110

ILE LEU TRP THR ILE ILE LEU VAL LEU SER ILE ILE VAL PHE ILE VAL LEU ILE ASN
   ATATTATGGACAATAATCCTGGTGTTATTATCAATAGTCTTCATCATAGTACGATTAA 180
   TATAATACCTGTTATTAGGACCACAATAATAGTTATCAGAAGTAGTATCACGATTAATT
           130         140         150         160         170

SER ILE LYS SER GLU LYS ALA HIS GLU SER LEU LEU GLN ASP ASN ASN GLU PHE MET
   TCCATCAAAAGTGAAAAAGGCTCATGAATCATTGCTGCAAGACATAAATAATGAGTTTAT 240
   AGGTAGTTTTCACTTTTTCCGAGTACTTAGTAACGACGTTCTGTATTTATTACTCAAATA
           190         200         210         220         230

ALA SER ASP ASN LEU ILE GLN SER GLY
   GCATCGGATAACCAATGATCTAATACAGTCAGG 300
   CGTAGCCTATTGGTTACCTAGATTATGTCAGTCC
           250         260         270         280         290

GLU [ILE] THR GLU LYS ILE LEU LEU LEU THR ILE GLN SER HIS VAL GLN ASN TYR ILE PRO ILE SER LEU
   GGAAATTACAGAGAAAATCCTTTCTTACAATTCAGAGTCATGTCCAGAATTATACCAATATCACT 360
   CCTTTAATGTCTCTTTTAGGAAATGTTAAGTCTCAGTACAGGTCTTAATATATGGTTATAGTGA
           310         320         330         340         350

VAL ASN THR ARG LEU LEU THR ILE GLN SER HIS VAL GLN ASN TYR ILE PRO ILE SER LEU
   AGTGAATACAAGGCTTCTTACAATTCAGAGTCATGTCCAGAATTATACCAATATCACT
   TCACTTATGTTCCGAAGAATGTTAAGTCTCAGTACAGGTCTTAATATATGGTTATAGTGA
```

```
THR GLN GLN MET SER ASP LEU ARG LYS PHE ILE SER GLU ILE THR ILE ARG ASN ASP ASN
GACACAACAGATGTCAGATCTTAGGAAATTCATTAGTGAAATTACAATTAGAAATGATAA
CTGTGTTGTCTACAGTCTAGAATCCTTTAAGTAATCACTTTAATGTTACTTTACTATT
                    380                         400                420

GLN GLU VAL LEU PRO GLN ARG ILE THR ILE THR HIS ASP VAL GLY ILE LYS PRO LEU ASN PRO ASP
    TCAAGAAGTGCTGCCACAAAGAATAACACATGATGTGGGTATAAAACCTTTAAATCCAGA
    AGTTCTTCACGACGGTGTTTCTTATTGTACTACACCCATATTTTGGAAATTTAGGTCT
                        440                         460                480

ASP PHE TRP ARG CYS THR SER GLY LEU PRO SER LEU MET LYS THR PRO LYS ILE ARG LEU
TGATTTTTGGAGATGCACGTCTGGTCTTCCATCTCTTAATGAAAACTCCAAAAATAAGGTT
ACTAAAAACCTCTACGTGCAGACCAGAAGGTAGAGAATTACTTTTGAGGTTTTATTCCAA
                    500                         520                540

MET PRO GLY PRO GLY LEU LEU ALA MET PRO THR THR VAL ASP GLY CYS ILE ARG THR PRO
AATGCCAGGGCCGGGATTATTAGCTATGCCAACGACTGTTGATGGCTGTATCAGAACTCC
TTACGGTCCCGGCCCTAATAATCGATACGGTTGCTGACAACTACCGACATAGTCTTGAGG
                    560                         580                600

SER LEU VAL ILE ASN ASP LEU ILE TYR ALA TYR THR SER ASN LEU ILE THR ARG GLY CYS
GTCCTTAGTTATATAAATGATCTTATATGCTTATACCTCAAATCTAATTACTCGAGGTTG
CAGGAATCAATATATTTACTAGACTAAAATACGAATATGGAGTTTAGATTAATGAGCTCCAAC
                    620                         640                660

GLN ASP ILE GLY LYS SER TYR GLN VAL LEU GLN ILE GLY ILE THR ILE THR VAL ASN SER ASP
TCAGGATATAGGAAAATCATATCAAGTCTTACAGATCTTACAGAATAACTGTAAACTCAGA
AGTCCTATATCCTTTTAGTATAGTTCAGAATGTCTATATTATTGACATTTGAGTCT
                    680                         700                720

LEU VAL PRO ASP LEU ASN PRO ARG ILE SER HIS THR PHE ASN ILE ASN ASP ASN ARG LYS
CTTGGTACCTGACTTAAATCCCAGGATCTCTCATACTTTAACATAAATGACAATAGGAA
GAACCATGGACTGAATTTAGGGTCCTAGAGAGTATGAAAATTGTATTTACTGTTATCCTT
                    740                         760                780
```

FIG. 3B.

```
SRE CYS SER LEU ALA LEU LEU ASN THR ASP VAL TYR GLN LEU CYS SER THR PRO LYS VAL
GTCATGTTCTCTAGCACTCCTAAATACAGATGTATATCAACTGTGTTCAACTCCCAAAGT
CAGTACAAGAGATCGTGAGGATTTATGTCTACATATAGTTGACACAAGTTGAGGGTTTCA
                790                  800                  810                  820                  830                  840

ASP GLU ARG SER ASP TYR ALA SER SER GLY ILE GLU ASP ILE VAL LEU ASP ILE VAL ASN
TGATGAAAGATCAGATTATGCATCATCAGGCATAGAAGATATTGTACTTGATATTGTCAA
ACTACTTTCTAGTCTAATACGTAGTAGTCCGTATCTTCTATAACATGAACTATAACAGTT
                850                  860                  870                  880                  890                  900

TYR ASP GLY SER ILE SER THR THR ARG PHE LYS ASN ASN ILE SER PHE ASP GLN PRO
TTATGATGGCTCAATCTCAACAACAAGATTTAAGAATAACATAAGCTTTGATCAACC
AATACTACCGAGTTAGAGTTGTTGTTCTAAATTCTTATTGTATTCGAAACTAGTTGG
                910                  920                  930                  940                  950                  960

TYR ALA ALA LEU TYR PRO SER VAL GLY PRO GLY ILE TYR TYR LYS GLY LYS ILE ILE PHE
TTATGCTGCACTATACCCATCTGTTGGACCAGGGATATACTACAAAGGCAAAATAATATT
AATACGACGTGATATGGGTAGACAACCTGGTCCCTATATGATGTTTCCGTTTTATTATAA
                970                  980                  990                 1000                 1010                 1020

LEU GLY TYR GLY GLY LEU GLU HIS PRO ILE ASN GLU ASN [VAL] ILE CYS ASN THR THR GLY
TCTCGGGTATGGAGGTCTTGAACATCCAATAAATGAGAATGTAATCTGCAACAACTGG
AGAGCCCATACCTCCAGAACTTGTAGGTTATTTACATTAGACGTTGTGTTGACC
               1030                 1040                 1050                 1060                 1070                 1080

CYS PRO GLY LYS THR GLN ARG ASP CYS ASN GLN ALA SER HIS SER PRO TRP PHE SER ASP
GTGTCCCGGGAAAACAGAGACTGCAATCAGGCATCTCATAGTCCATGGTTTCAGA
CACAGGGCCCTTTTGTCTCTGACGTTAGTCCGTAGAGTATCAGGTACCAAAAGTCT
               1090                 1100                 1110                 1120                 1130                 1140

ARG ARG MET VAL ASN SER ILE ILE VAL VAL ASP LYS GLY LEU ASN SER ILE PRO LYS LEU
TAGGAGGATGGTCAACTCTATCATTGTTGTTGACAAAGGCTTAAACTCAATTCCAAAATT
ATCCTCCTACCAGTTGAGATAGTAACAACAACTGTTTCCGAATTTGAGTTAAGGTTTTAA
               1150                 1160                 1170                 1180                 1190                 1200
```

FIG.3C.

```
LYS VAL TRP THR ILE SER MET ARG GLN ASN TYR TRP TRP GLY SER GLU GLY ARG LEU LEU LEU
GAAGGTATGGACGAGATATCTATGAGACAGAATTACTGGGGGGTCAGAAGGAAGGTTACTTCT
CTTCCATACCTGCTATAGATACTCTGTCTTAATGACCCCAGTCTTCCTTCCAATGAAGA
                    1210                1220                1230                1240                1250                1260

LEU GLY ASN LYS ILE TYR THR ARG SER THR TRP HIS SER LYS LEU GLN LEU
ACTAGGTAACAAGATCTATATATACAAGATCCACAAGTTGGCATAGCAAGTTACAATT
TGATCCATTGTTCTAGATATATATGTTCTAGGTGTTCAACCGTATCGTTCAATGTTAA
                    1270                1280                1290                1300                1310                1320

GLY ILE ILE ASP THR ASP TYR SER ASP ILE ARG ILE LYS TRP THR TRP HIS ASN VAL
AGGAATAATTGATATTACTGATTACAGTGATATAAGGATAAAATGGACATGGCATAATGT
TCCTTATTAACTATAATGACTAATGTCACTATATTCCTATTTTACCTGTACCGTATTACA
                    1330                1340                1350                1360                1370                1380

LEU SER ARG PRO GLY ASN ASN GLU CYS TRP GLY HIS SER CYS PRO ASP GLY CYS ILE
GCTATCAAGAGACCAGGAAACAATGAATGTCCATGGGGACATTCATGTCCAGATGGATGTAT
CGATAGTTCTCTGGTCCTTTGTTACTTACAGGTACCCCTGTAAGTACAGGTCTACCATA
                    1390                1400                1410                1420                1430                1440

THR GLY VAL TYR THR ASP ALA TYR PRO LEU ASN PRO THR GLY SER ILE VAL SER SER VAL
AACAGGAGTATATACTGATGCATATCCACTCAATCCCACAGGAGCATTGTGTCATCTGT
TTGTCCTCATATATGACTACGTATAGGTGAGTTAGGGTGTCCTCGTAACACAGTAGACA
                    1450                1460                1470                1480                1490                1500

ILE LEU ASP SER GLN LYS SER ARG VAL ASN PRO VAL ILE THR TYR SER THR [ALA] THR GLU
CATATTAGATTCACAAAAATCGAGAGTGAACCCAGTCATAACTTACTCAACAGCACCGA
GTATAATCTAAGTGTTTTTTAGCTCTCACTTGGTCAGTATTGAATGAGTTGTCGTTGGCT
                    1510                1520                1530                1540                1550                1560

ARG VAL ASN GLU LEU ALA ILE [ARG] ASN ARG THR LEU SER ALA GLY TYR THR THR THR SER
AAGAGTAAACGAGAGCTGGCCATCCGAAACAGAACACTCTCAGCTGGATATACAACAAG
TTCTCATTTGCTCTCGACCGGTAGGCTTTGTCTTGTGAGAGTCGACCTATATGTTGTTC
                    1570                1580                1590                1600                1610                1620
```

FIG.3D.

```
CYS ILE THR HIS TYR ASN LYS GLY TYR CYS PHE HIS ILE VAL GLU ILE ASN [GLN] LYS SER
CTGCATCACACACTATAAACAAAGGATATTGTTTCATATAGTAGAAATAAATCAGAAAAG
              1630              1640              1650              1660              1670              1680
GACGTAGTGTGTGATATTGTTTCCTATAACAAAGTATCATCTTTATTTAGTCTTTTC

LEU [ASN] THR [LEU] GLN PRO MET LEU PHE LYS THR GLU [VAL] PRO LYS SER CYS SER ***
CTTAAACACTTCAACCCATGTTGTTCAAGACAGAGGTTCCAAAAGCTGCAGTTAATC
              1690              1700              1710              1720              1730              1740
GAATTTGTGAAGTTGGGTACAACAAGTTCTGTCTCCAAGGTTTTTCGACGTCAATTAG

ATAATTAACCGCAATATGCATTAACCTATCTATAATACAAGTATATGATAAGTAATCAGC
TATTAATTGGCGTTATACGTAATTGGATAGATATTATGTTCATATACTATTCATTAGTCG
              1750              1760              1770              1780              1790              1800

AATCAGACAATAGACAAAAGGGAAATATAAAAA
TTAGTCTGTTATCTGTTTTCCCTTTATATTTTT
              1810              1820              1830

NUCLEOTIDE SEQUENCE OF THE PIV-3 HN GENE. THE cDNA SEQUENCE
IS SHOWN IN THE PLUS (mRNA) STRAND SENSE IN THE 5' TO 3'
DIRECTION. THE TRANSMEMBRANE (TM) ANCHOR DOMAIN IS UNDERLINED. AMINO ACIDS
DIFFERING FROM THE PUBLISHED PRIMARY SEQUENCE OF THE PROTEIN ENCODED BY THE PIV-3
HN GENE ARE BOXED.
```

FIG.3E.

RESTRICTION MAP OF THE PIV-3 HN GENE

FIG.5A. NUCLEOTIDE SEQUENCE OF THE RSV F GENE.

```
                                                    SP
5' MET GLU LEU  PRO  ILE LEU LYS ALA ASN ALA ILE THR THR ILE LEU ALA  ALA  VAL THR PHE
   ATG GAG TTG CCA ATC CTC AAA GCA AAT GCA ATT ACC ACA ATC CTC GCT GCA GTC ACA TTT
                         10                    20                    30                    40                    50                    60

CYS PHE ALA  SER  SER GLN ASN ILE THR GLU GLU PHE TYR GLN SER THR CYS SER ALA VAL
   TGC TTT GCT TCT AGT CAA ACA ATC ACT GAA GAA TTT TAT CAA TCA ACA TGC AGT GCA GTT
                         70                    80                    90                   100                   110                   120

SER LYS GLY TYR LEU SER ALA LEU ARG THR GLY TRP TYR THR SER VAL ILE THR ILE GLU
   AGC AAA GGC TAT CTT AGT GCT CTA AGA ACT GGT TGG TAT ACT AGT GTT ATA ACT ATA GAA
                        130                   140                   150                   160                   170                   180

LEU SER ASN ILE LYS GLU ASN LYS CYS ASN GLY THR ASP ALA LYS VAL LYS LEU  MET  LYS
   TTA AGT AAT ATC AAG GAA AAT AAG TGT AAT GGA ACA GAT GCT AAG GTA AAA TTG ATG AAA
                        190                   200                   210                   220                   230                   240

GLN GLU LEU ASP LYS TYR LYS ASN ALA VAL THR GLU LEU GLN LEU LEU MET GLN SER THR
   CAA GAA TTA GAT AAA TAT AAA AAT GCT GTA ACA GAA TTG CAG TTG CTC ATG CAA AGC ACA
                        250                   260                   270                   280                   290                   300

PRO  ALA  ALA ASN ASN ARG ALA ARG ARG GLU LEU PRO ARG PHE MET ASN TYR THR LEU ASN
   CCA GCA GCA AAC AAT CGA GCC AGA AGA GAA CTA CCA AGG TTT ATG AAT TAT ACA CTC AAC
                        310                   320                   330                   340                   350                   360
```

FIG. 5B.

```
                                                                    F2-F1 CLEAVAGE SITE
ASN [THR] LYS LYS THR ASN VAL THR LEU SER LYS LYS ARG ARG↓PHE LEU GLY PHE
AAT ACC AAA AAA ACC AAT GTA ACA TTA AGC AAG AAA AGA AGA GAT TTC TTG GTT T
    370                         380                390                 400                410                  420
TTA TGG TTT TTT TGG TTA CAT TGT AAT TCG TTC TTT CTA AAG AAC CAA AA

LEU LEU GLY VAL GLY SER ALA [ILE] ALA VAL SER LYS VAL LEU HIS LEU
TTG TTA GGT GTT GGA TCT GCA ATT GCT GTA TCT AAG GTC CTG CAC TTA
    430                 440                 450                460                  470                    480
AAC AAT CCA CAA CCT AGA CGT TAA CGA CAT AGA TTC CAG GAC GTG AAT

GLU GLY VAL ASN LYS ILE LYS SER ALA LEU LEU SER THR ASN LYS ALA VAL VAL SER
GAA GGA GAA GTG AAC AAG ATC AAA AGT GCT CTA CTA CCA AAA CAA GGC CGT AGT CAG T
    490                500                 510                  520                    530              540
CTT CCT CTT CAC TTG TTC TAG TTT TCA CGA GAT GAT GGT TTT GTT CCG GCA TCA GTC A

LEU SER ASN GLY VAL SER VAL LEU THR SER LYS VAL LEU ASP LEU LYS ASN TYR ILE ASP
TTA TCA AAT GGA GTT AGT GTC TTA ACC AGC AAA GTG TTA GAC CTC AAA AAC TAT AGA T
    550                 560                 570                 580                    590                600
AAT AGT TTA CCT CAA TCA CAG AAT TGG TCG TTT CAC AAT CTG GAG TTT TTG ATA TAT CTA

LYS GLN LEU LEU PRO ILE VAL ASN LYS GLN SER CYS [ARG] ILE SER ASN ILE GLU THR VAL
AAA CAA TTG TTA CCT ATT GTG AAT AAG CAG AAG CTG CAG AAT ATC AAA TAG TTT GAT GTG
    610                620                 630                 640                 650               660
TTT GTT AAC AAT GGA TAA CAC TTA TTC GCT TCG ACG TCT TAT AGT TTA TAT CTT TGA CAC

ILE GLU PHE GLN HIS LYS ASN ASN ARG LEU LEU GLU ILE THR ARG GLU PHE SER VAL ASN
ATA GAG TTC CAA CAA CAA GAA CAA CAA GAA CTA GAG ATT ACC AGG GAA TTT AGT GTT AAT
    670                  680                 690                  700                      710                720
TAT CTC AAG GTT GTT GTT CTT GTT GTT CTT GAT CTC TAA TGG TCC CTT AAA TCA CAA TTA

ILE GLY VAL THR THR PRO VAL SER THR TYR MET LEU THR ASN SER GLU LEU LEU SER LEU
ATA GGT GTA ACT ACA CCT GTA AGC ACT TAC ATG TTA ACT AAT AGT GAA TTA TTG TCA TTA
    730                        740                  750                 760                    770                780
CGT TCC ACA TTG ATG TGG ACA TTC GTG AAT GTA CAA TTG ATT ATC ACT TAA TAA CAG TAA T
```

FIG. 5C.

```
ILE ASN ASP MET PRO ILE THR ASN ASP GLN LYS LYS LEU MET SER ASN ASN VAL GLN ILE
ATCAATGATATGCCTATAACAAATGATCAGAAAAAGTTAATGTCCAACAATGTTCAAATA
TAGTTACTATACGGATATTGTTTACTAGTCTTTTTCAATTACAGGTTGTTACAAGTTTAT
            790           800           810           820           830          840

VAL ARG GLN SER TYR SER ILE MET SER ILE ILE LYS GLU GLU VAL LEU ALA TYR VAL
GTTAGACAGCAAAGTTACTCTATCATGTCCATAATAAAAGAAGAAGTCTTAGCATATGTA
CAATCTGTCGTTTCAATGAGATAGTACAGGTATTATTTTCTTCTTCAGAATCGTATACAT
            850           860           870           880           890           900

VAL GLN LEU PRO LEU TYR GLY VAL ILE ASP THR PRO CYS TRP LYS LEU HIS THR SER PRO
GTACAATTACCACTATATGGTGTGATAGATACACCTTGTTGGAAATTACACACATCCCCT
CATGTTAATGGTGATATACCACACTATCTATGTGGAACAACCTTTAATGTGTGTAGGGGA
            910           920           930           940           950           960

LEU CYS THR THR ASN THR LYS GLU GLY SER ASN ILE CYS LEU THR ARG THR ASP ARG GLY
CTATGTACAACCAACACAAAAGAAGGGTCAAACATCTGTTTAACAAGAACTGACAGAGGA
GATACATGTTGGTTGTGTTTTCTTCCCAGTTTGTAGACAAATTGTTCTTGACTGTCTCCT
            970           980           990          1000          1010          1020

TRP TYR CYS ASP ASN ALA GLY SER VAL SER PHE PHE PRO GLN ALA GLU THR CYS LYS [VAL] ASN
TGGTACTGTGACAATGCAGGATCAGTATCTTTCTTCCCACAAGCTGAAACATGTAAAGTT
ACCATGACACTGTTACGTCCTAGTCATAGAAAGAAGGGTGTTCGACTTTGTACATTTCAA
           1030          1040          1050          1060          1070          1080

GLN SER ASN ARG VAL PHE CYS ASP THR MET ASN SER LEU THR LEU PRO SER GLU VAL ASN
CAATCGAATCGAGTATTTTGTGACACAATGAACAGTTTAACATTACCAAGTGAAGTAAAT
GTTAGCTTAGCTCATAAAACACTGTGTTACTTGTCAAATTGTAATGGTTCACTTCATTTA
           1090          1100          1110          1120          1130          1140

LEU CYS ASN VAL ASP ILE PHE ASN PRO LYS TYR ASP CYS LYS ILE MET THR SER LYS THR
CTCTGCAATGTTGACATATTCAATCCCAAATATGATTGTAAAATTATGACTTCAAAAACA
GAGACGTTACAACTGTATAAGTTAGGGTTTATACTAACATTTTAATACTGAAGTTTTGT
           1150          1160          1170          1180          1190          1200
```

FIG. 5D.

```
ASP VAL SER SER VAL ILE THR SER LEU GLY ALA ILE VAL SER CYS TYR GLY LYS THR
GATGTAAGCAGCTCGTTATCACATCTCTAGGAGCCATTGTGTCATGCTATGGCAAAACT
CTACATTCGTCGAGGCAATAGTGTAGAGATCCTCGGTAACACAGTACGATACCGTTTTGA   1260
                1220            1230            1240            1250

LYS CYS THR ALA SER ASN LYS ASN ARG GLY ILE ILE LYS THR PHE SER ASN GLY CYS ASP
AAATGTACAGCAGCATCCAATAAAAATCGTGGAATCATAAAGACATTTCTAACGGGTGTGAT
TTTACATGTCGTAGGTTATTTTTAGCACCTTAGTATTTCTGTAAAGATTGCCCACACTA    1320
                1280            1290            1300            1310

TYR VAL SER ASN LYS GLY VAL ASP THR VAL SER VAL GLY ASN THR LEU TYR TYR VAL ASN
TATGTATCAAATAAAGGGGTGGACACTGTGTCTGTAGGTAACACATTATATTATGTAAAT
ATACATAGTTTATTTCCCACCTGTGACACAGATCCATTGTAATATAATACATTTA        1380
                1330            1340            1350            1360            1370

LYS GLU GLY LYS SER LEU TYR VAL LYS GLY PRO ILE ILE ASN PHE TYR ASP PRO
AAGCAAGAAGGCAAAAGTCTCTATGTAAAAGGTGAACCAATAAATTTCTATGACCCA
TTCGTTCTTCCGTTTTCAGAGATACATTTTCCACTTGGTTATTTAAAGATACTGGGT      1440
                1390            1400            1410            1420            1430

LEU VAL PHE PRO SER ASP GLU PHE ASP GLU PHE ALA SER ILE SER GLN VAL ASN GLU LYS ILE ASN
TTAGTATTCCCCTCTGATGAATTTGATGCATCAATATCTCAAGTCAACGAGAAGATTAAC
AATCATAAGGGGAGACTACTTAAACTACGTAGTTATAGAGTTCAGTTGCTCTTCTAATTG   1500
                1450            1460            1470            1480            1490

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
GTCTCAAATCGTAAATAAGCATTTAGGCTACTTAATAATGTATTACATTTACGACCATTT   1560
                1510            1520            1530            1540            1550

SER THR ASN ILE MET ILE THR ILE ILE GLU ILE ILE VAL ILE ILE LEU LEU SER
TCAACCACAAATATCATGATAACTATTATAGAGATTATAGTAAATTGTTATCA
AGTTGGTGTTTATAGTACTATTGATGATATCTCTAATATCATTATAACAATAGT        1620
                1570            1580            1590            1600            1610
                                    TM
```

```
         LEU ILE ALA VAL GLY LEU LEU LEU TYR CYS LYS ALA ARG SER THR PRO VAL THR LEU SER
TTAATTGCTGTTGGACTGCTCCTATACTGTAAGGCCAGAAGCACCAGTCACACTAAGC
AATTAACGACAACCTGACGAGGATATGACATTCCGGTCTTCGTGGTCAGTGTGATTCG
                1630                1640                1650                1660                1670                1680

LYS ASP GLN LEU SER GLY ILE ALA ASN ASN ILE ALA PHE SER ASN
AGGATCAACTGAGTGGTATAAATAATATTGCATTTAGTAACTGAATAAAAATAGCACCT
TTCCTAGTTGACTCACCATATTTATTATAACGTAAATCATTGACTTATTTTATCGTGGA
                1690                1700                1710                1720                1730                1740

AATCATGTTCTTACAATGGTTTACTATCTGCTCATAGACAACCCATCTATCATTGGATTT
TTAGTACAAGAATGTTACCAAATGATAGACGAGTATCTGTTGGGTAGATAGTAACCTAAA
                1750                1760                1770                1780                1790                1800

TCTTAAAATCTGAACTTCATCGAAACTCTTATCTATAAACCATCTCACTTACACTATTTA
AGAATTTTAGACTTGAAGTAGCTTTGAGAATAGATATTTGGTAGAGTGAATGATAAAT
                1810                1820                1830                1840                1850                1860

AGTAGATTCCTAGTTTATAGTTATAT   3'
TCATCTAAGGATCAAATATCAATATA
                1870                1880

NUCLEOTIDE SEQUENCE OF THE RSV F GENE. THE cDNA SEQUENCE IS SHOWN IN THE PLUS (mRNA)
STRAND SENSE IN THE 5' TO 3' DIRECTION. THE SIGNAL PEPTIDE (SP) AND THE TRANSMEMBRANE (TM)
ANCHOR DOMAIN ARE UNDERLINED. THE PREDICTED F2-F1 CLEAVAGE SITE IS INDICATED BY THE ARROW
(↑). AMINO ACIDS DIFFERING FROM THE PUBLISHED PRIMARY SEQUENCE OF THE PROTEIN ENCODED BY
THE RSV F GENE ARE BOXED.
```

FIG.5E.

FIG. 7A. NUCLEOTIDE SEQUENCE OF THE RSV G GENE

```
              MET   SER   LYS   ASN   LYS   ASP   GLN   ARG
         T G C A A A C A T G T C C A A A A A C A A G G A C C A A C G
         A C G T T T G T A C A G G T T T T T G T T C C T G G T T G C
                       10                  20                  30

THR   ALA   LYS   THR   LEU   GLU  [LYS]  THR   TRP   ASP
     C A C C G C T A A G A C A C T A G A A A A G A C C T G G G A
     G T G G C G A T T C T G T G A T C T T T T C T G G A C C C T
                   40                  50                  60

THR   LEU   ASN   HIS   LEU   LEU   PHE   ILE   SER   SER
     C A C T C T C A A T C A T T T A T T A T T C A T A T C A T C
     G T G A G A G T T A G T A A A T A A T A A G T A T A G T A G
                   70                  80                  90
                                                              ←
    [GLY]  LEU   TYR   LYS   LEU   ASN   LEU   LYS   SER   VAL
     G G G C T T A T A T A A G T T A A A T C T T A A A T C T G T
     C C C G A A T A T A T T C A A T T T A G A A T T T A G A C A
                  100                 110                 120
    ─────────────────────── TM ───────────────────────
         ALA   GLN   ILE   THR   LEU   SER   ILE   LEU   ALA   MET
         A G C A C A A A T C A C A T T A T C C A T T C T G G C A A T
         T C G T G T T T A G T G T A A T A G G T A A G A C C G T T A
                       130                 140                 150
    ─────────────────────────────────────────────────────
     ILE   ILE   SER   THR   SER   LEU   ILE   ILE  [THR]  ALA
     G A T A A T C T C A A C T T C A C T T A T A A T T A C A G C
     C T A T T A G A G T T G A A G T G A A T A T T A A T G T C G
                  160                 170                 180
    ─────────────────────────────────────────────────→
     ILE   ILE   PHE   ILE   ALA   SER   ALA   ASN   HIS   LYS
     C A T C A T A T T C A T A G C C T C G G C A A A C C A C A A
     G T A G T A T A A G T A T C G G A G C C G T T T G G T G T T
                  190                 200                 210

VAL   THR  [LEU]  THR   THR   ALA   ILE   ILE   GLN   ASP
         A G T C A C A C T A A C A A C T G C A A T C A T A C A A G A
         T C A G T G T G A T T G T T G A C G T T A G T A T G T T C T
                       220                 230                 240

ALA   THR   SER   GLN   ILE   LYS   ASN   THR   THR   PRO
         T G C A A C A A G C C A G A T C A A G A A C A C A A C C C C
         A C G T T G T T C G G T C T A G T T C T T G T G T T G G G G
                       250                 260                 270

THR   TYR   LEU   THR   GLN  [ASP]  PRO   GLN   LEU   GLY
         A A C A T A C C T C A C T C A G G A T C C T C A G C T T G G
         T T G T A T G G A G T G A G T C C T A G G A G T C G A A C C
                       280                 290                 300
```

FIG.7B.

```
    ILE   SER  [PHE]  SER   ASN  [LEU]  SER   GLU   ILE   THR
    A A T C A G C T T C T C C A A T C T G T C T G A A A T T A C
    T T A G T C G A A G A G G T T A G A C A G A C T T T A A T G
              310                 320                 330

SER   GLN  [THR]  THR   THR   ILE   LEU   ALA   SER   THR
    A T C A C A A A C C A C C A C C A T A C T A G C T T C A A C
    T A G T G T T T G G T G G T G G T A T G A T C G A A G T T G
              340                 350                 360

THR   PRO   GLY   VAL   LYS   SER  [ASN]  LEU   GLN  [PRO]
    A A C A C C A G G A G T C A A G T C A A A C C T G C A A C C
    T T G T G G T C C T C A G T T C A G T T T G G A C G T T G G
              370                 380                 390

THR   THR   VAL   LYS   THR   LYS   ASN   THR   THR   THR
    C A C A A C A G T C A A G A C T A A A A A C A C A A C A A C
    G T G T T G T C A G T T C T G A T T T T T G T G T T G T T G
              400                 410                 420

THR   GLN   THR   GLN   PRO   SER   LYS   PRO   THR   THR
    A A C C C A A A C A C A A C C C A G C A A G C C C A C T A C
    T T G G G T T T G T G T T G G G T C G T T C G G G T G A T G
              430                 440                 450

LYS   GLN   ARG   GLN   ASN   LYS   PRO   PRO  [ASN]  LYS
    A A A A C A A C G C C A A A A C A A A C C A C C A A A C A A
    T T T T G T T G C G G T T T T G T T T G G T G G T T T G T T
              460                 470                 480

PRO   ASN   ASN   ASP   PHE   HIS   PHE   GLU   VAL   PHE
    A C C C A A T A A T G A T T T T C A C T T C G A A G T G T T
    T G G G T T A T T A C T A A A A G T G A A G C T T C A C A A
              490                 500                 510

ASN   PHE   VAL   PRO   CYS   SER   ILE   CYS   SER   ASN
    T A A C T T T G T A C C C T G C A G C A T A T G C A G C A A
    A T T G A A A C A T G G G A C G T C G T A T A C G T C G T T
              520                 530                 540

ASN   PRO   THR   CYS   TRP   ALA   ILE   CYS   LYS   ARG
    C A A T C C A A C C T G C T G G G C T A T C T G C A A A A G
    G T T A G G T T G G A C G A C C C G A T A G A C G T T T T C
              550                 560                 570

ILE   PRO   ASN   LYS   LYS   PRO   GLY   LYS   LYS   THR
    A A T A C C A A A C A A A A A A C C A G G A A A G A A A A C
    T T A T G G T T T G T T T T T T G G T C C T T T C T T T T G
              580                 590                 600
```

FIG. 7C.

```
      THR   THR   LYS   PRO   THR   LYS   LYS   PRO   THR   PHE
    C A C C A C C A A G C C T A C A A A A A A A C C A A C C T T
    G T G G T G G T T C G G A T G T T T T T T T G G T T G G A A
                  610                 620                 630

LYS   THR   THR   LYS   LYS   ASP  |LEU|  LYS   PRO   GLN
    C A A G A C A A C C A A A A A A G A T C T C A A A C C T C A
    G T T C T G T T G G T T T T T T C T A G A G T T T G G A G T
                  640                 650                 660

THR   THR   LYS  |PRO|  LYS   GLU   VAL   PRO   THR   THR
    A A C C A C T A A A C C A A A G G A A G T A C C C A C C A C
    T T G G T G A T T T G G T T T C C T T C A T G G G T G G T G
                  670                 680                 690

LYS   PRO   THR   GLU   GLU   PRO   THR   ILE   ASN   THR
    C A A G C C C A C A G A A G A G C C A A C C A T C A A C A C
    G T T C G G G T G T C T T C T C G G T T G G T A G T T G T G
                  700                 710                 720

THR   LYS   THR   ASN   ILE  |THR|  THR   THR   LEU   LEU
    C A C C A A A A C A A A C A T C A C A A C T A C A C T G C T
    G T G G T T T T G T T T G T A G T G T T G A T G T G A C G A
                  730                 740                 750

THR  |ASN|  ASN   THR   THR   GLY   ASN   PRO  |LYS|  LEU
    C A C C A A C A A C A C C A C A G G A A A T C C A A A A C T
    G T G G T T G T T G T G G T G T C C T T T A G G T T T T G A
                  760                 770                 780

THR   SER   GLN   MET   GLU   THR   PHE   HIS   SER   THR
    C A C A A G T C A A A T G G A A A C C T T C C A C T C A A C
    G T G T T C A G T T T A C C T T T G G A A G G T G A G T T G
                  790                 800                 810

SER   SER   GLU   GLY   ASN  |LEU|  SER   PRO   SER   GLN
    C T C C T C C G A A G G C A A T C T A A G C C C T T C T C A
    G A G G A G G C T T C C G T T A G A T T C G G G A A G A G T
                  820                 830                 840

VAL   SER   THR   THR   SER   GLU  |HIS|  PRO   SER   GLN
    A G T C T C C A C A A C A T C C G A G C A C C C A T C A C A
    T C A G A G G T G T T G T A G G C T C G T G G G T A G T G T
                  850                 860                 870

PRO   SER   SER   PRO   PRO   ASN   THR  |THR|  ARG   GLN
    A C C C T C A T C T C C A C C C A A C A C A A C A C G C C A
    T G G G A G T A G A G G T G G G T T G T G T T G T G C G G T
                  880                 890                 900
```

```
***
GTAGTTATTAAAAAAAAAA
CATCAATAATTTTTTTTTT
     910         920
```

NUCLEOTIDE SEQUENCE OF THE RSV G GENE. THE cDNA SEQUENCE IS SHOWN IN THE PLUS (mRNA) STRAND SENSE IN THE 5' TO 3' DIRECTION. THE TRANSMEMBRANE (TM) ANCHOR DOMAIN IS UNDERLINED. AMINO ACIDS DIFFERING FROM THE PUBLISHED PRIMARY SEQUENCE OF THE PROTEIN ENCODED BY THE RSV G GENE ARE BOXED.

FIG.7D.

Construction of a Bluescript-based expression vector containing the chimeric F$_{PIV-3}$ -F$_{RSV}$ gene with the 5' untranslated region of the PIV-3 F gene intact but lacking the nucleotide sequences coding for the hydrophobic anchor domains and cytoplasmic tails of both the PIV-3 and RSV F genes.

Step 1: Preparation of the plasmid containing the modified PIV-3 F gene

```
                    BspHI                        BamHI
           5'  __ATCAATCAAAGGTCCTGTGATAATAG____ 3'
               CGTAGTTAGTTTCCAGGACACTATTATCCTAG
```

FIG.9A.

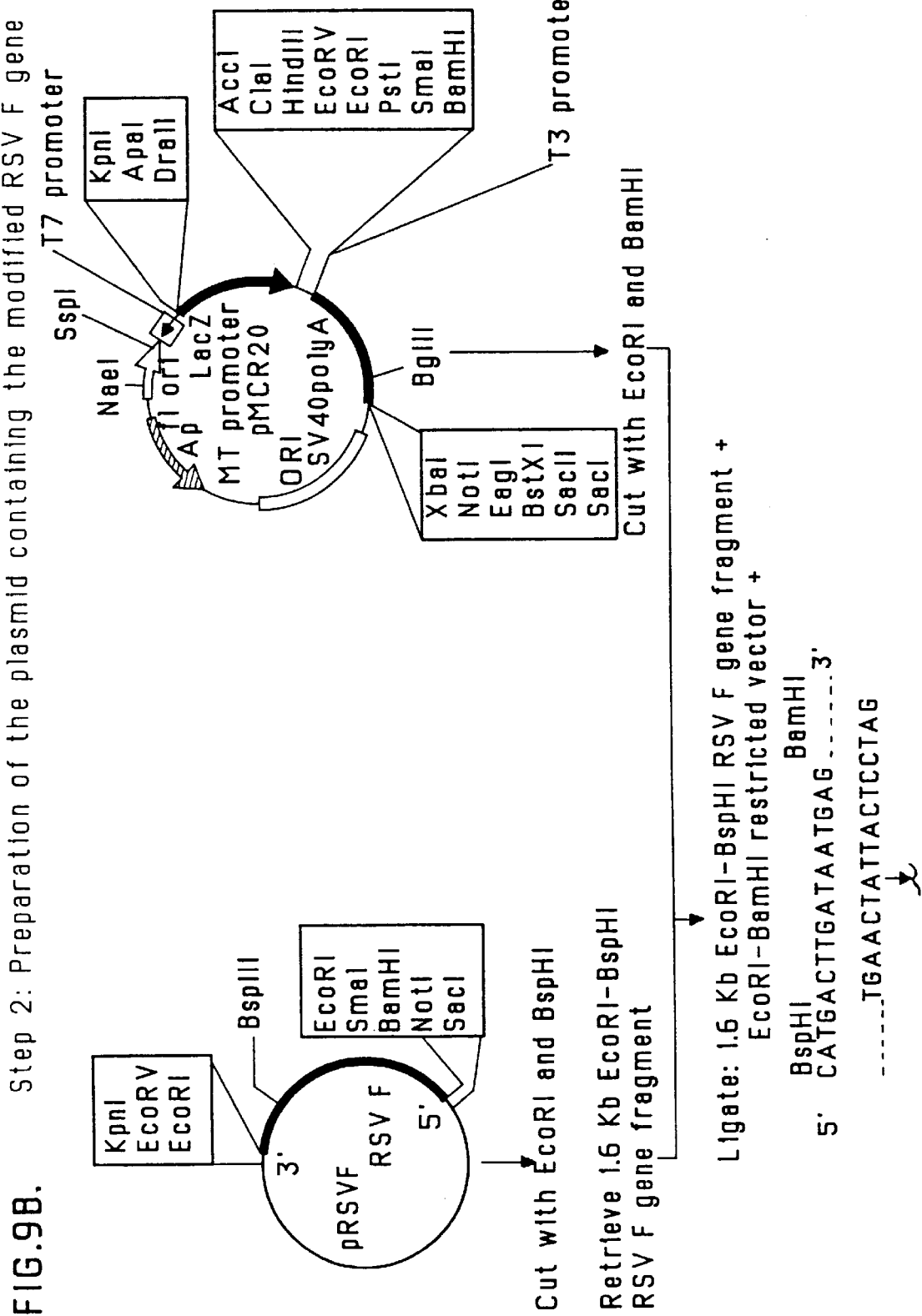
FIG.9B. Step 2: Preparation of the plasmid containing the modified RSV F gene

FIG.10B.

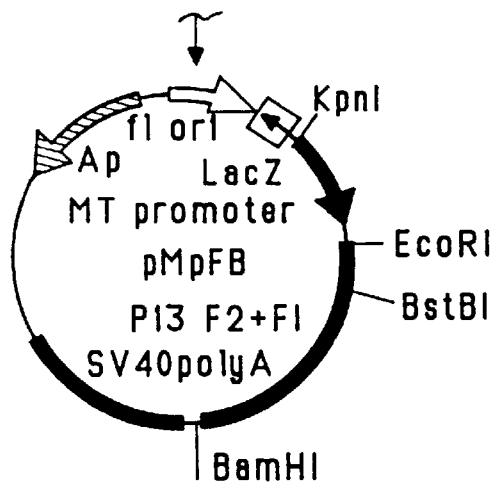

Cut with EcoRI and BstBI

↓

Retreive: EcoRI-BstBI restricted vector

↓

Ligate: EcoRI-BstBI restricted vector +

EcoRI                                                              PpuMI

AATTCATGCCAACTTTAATACTGCTAATTATTACAACAATGATTATGG
CATCTTCCTGCCAAATAGATATCACAAAACTACAGCAATGTAGGTGTA
TTGGTCAACAGTCCCAAAGGGATGAAGATATCACAAAACTT ____ 3'
____ GTACGGTTGAAATTATGACGATTAATAATGTTGTTACTAATACC
GTAGAAGGACGGTTTATCTATAGTGTTTTGATGTCGTACATCCACATA
ACCAGTTGTCAGGGTTTCCCTACTTCTATAGTGTTTTGAAGCTT

↓

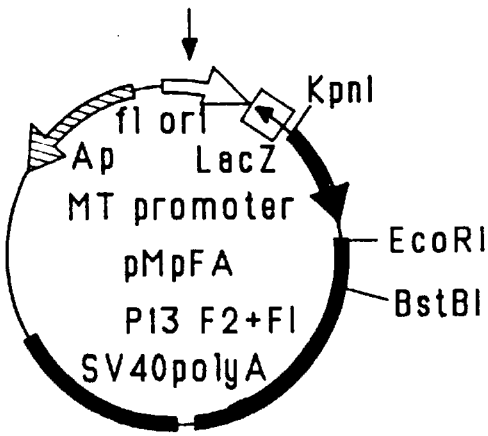

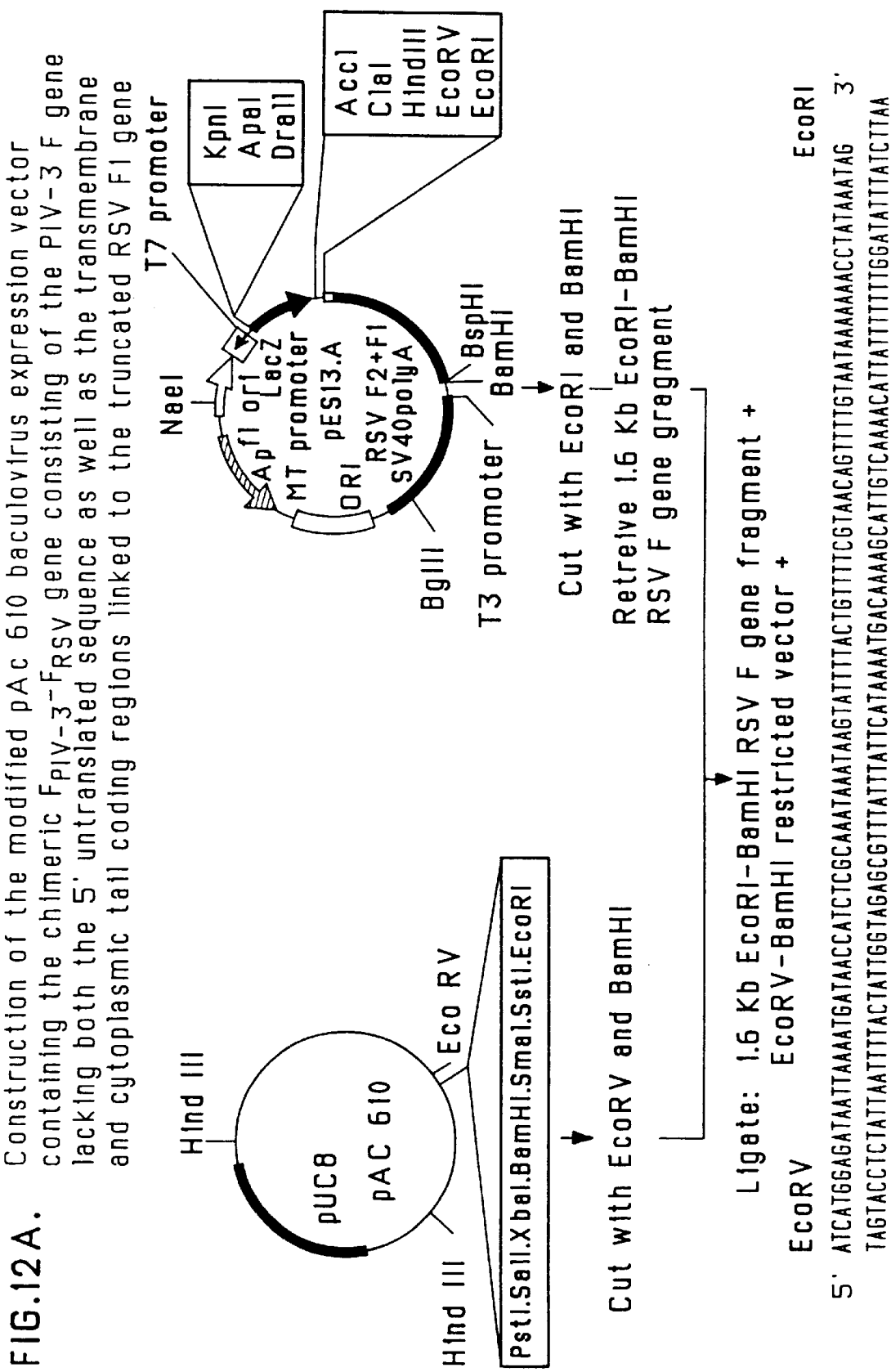
FIG.12A. Construction of the modified pAc 610 baculovirus expression vector containing the chimeric F_PIV-3-F_RSV gene consisting of the PIV-3 F gene lacking both the 5' untranslated sequence as well as the transmembrane and cytoplasmic tail coding regions linked to the truncated RSV F1 gene FIG.13
IMMUNOBLOTS OF CELL LYSATES FROM Sf9 CELLS
INFECTED WITH RECOMBINANT BACULOVIRUSES

| 1 | 2 | 3 | | 1 | 2 | 3 |
|---|---|---|---|---|---|---|
| RSV F2+1 | $F_{PIV-3}-F_{RSV}$ | WILD TYPE | | RSV F2+1 | $F_{PIV-3}-F_{RSV}$ | WILD TYPE |

A                                    B

FIG 13 : Immunoblots of cell lysates from Sf9 cells
infected wirth recombinant baculoviruses containing
the truncated RSV F gene ( Lane 1), the chimeric
$F_{PIV-3}-F_{RSV}$ gene (Lane 2) or infected with wild type
virus ( Lane 3) reacted with anti-F RSV Mab (panel A)
and anti-F1 PIV-3 antiserum (panel B)

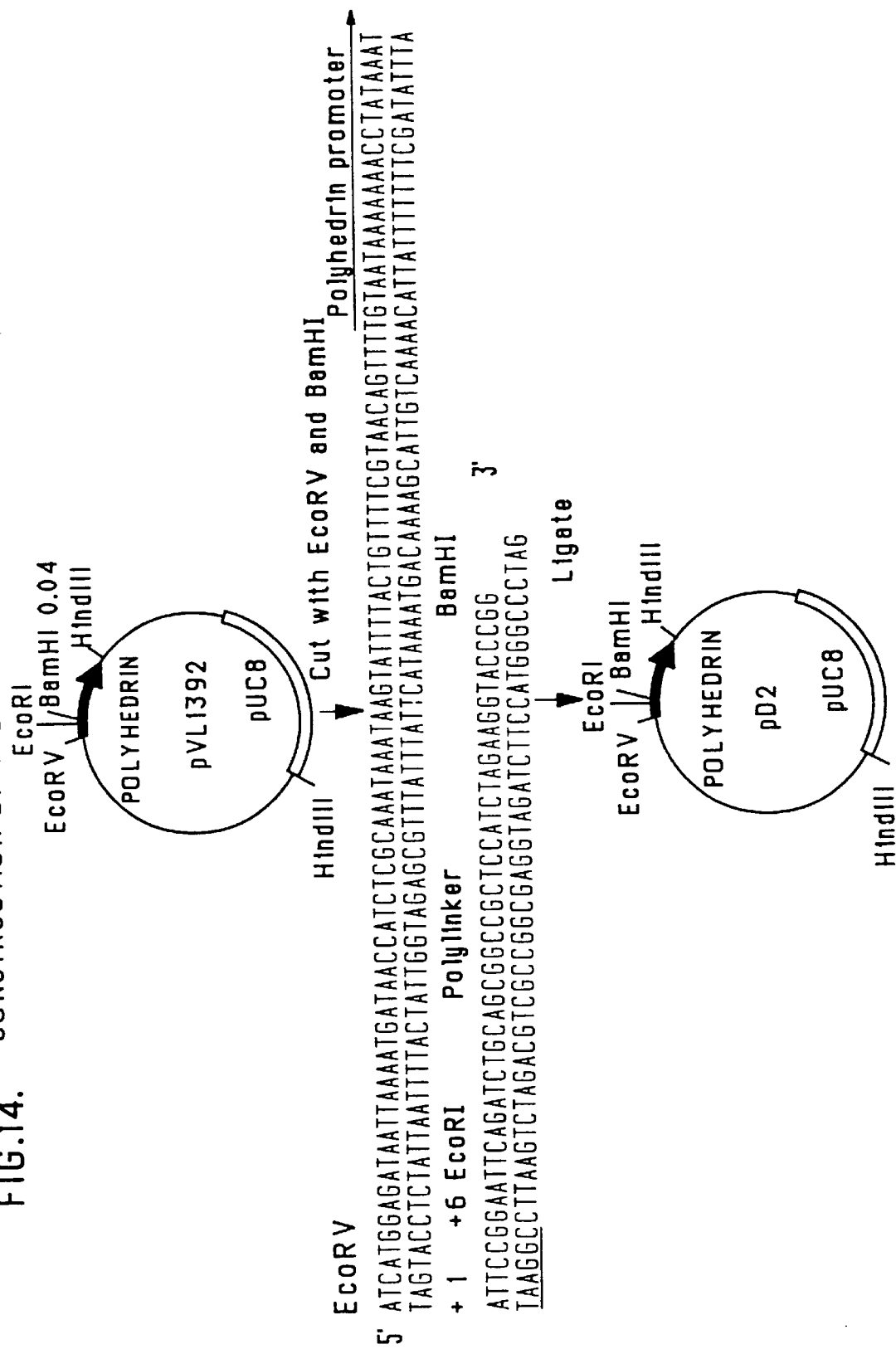
FIG. 14. CONSTRUCTION OF THE BACULOVIRUS TRANSFER VECTOR pD2

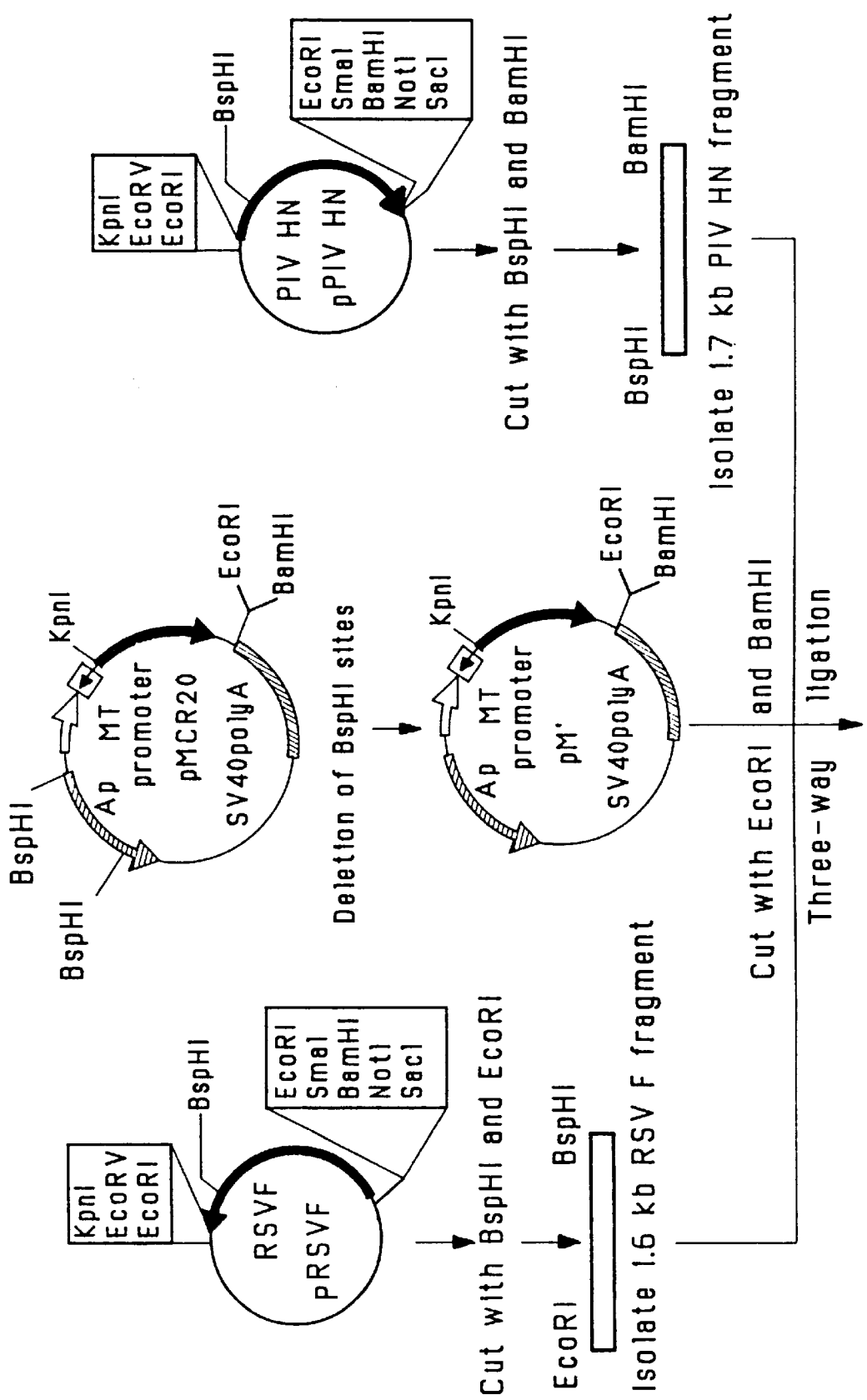
FIG. 15A. CONSTRUCTION OF THE $F_{RSV}$-$HN_{PIV3}$ CHIMERIC GENE

FIG.16
SDS POLY ACRYLAMIDE GEL AND IMMUNOBLOTS OF PURIFIED $F_{RSV}-HN_{PIV-3}$ CHIMERIC PROTEIN

106 K
80 K
50 K
33 K
28 K

← F-HN 1   2

A           B

FIG 16 : A) Coomassie-stained SDS polyacrylamide gel of immunoaffinity- purified $F_{RSV}-HN_{PIV-3}$ protein.

B) Immunoblots of $F_{RSV}-HN_{PIV-3}$ protein reacted with an anti-F RSV Mab ( lane 1 ) and anti-HN PIV-3 antiserum ( lane 2)

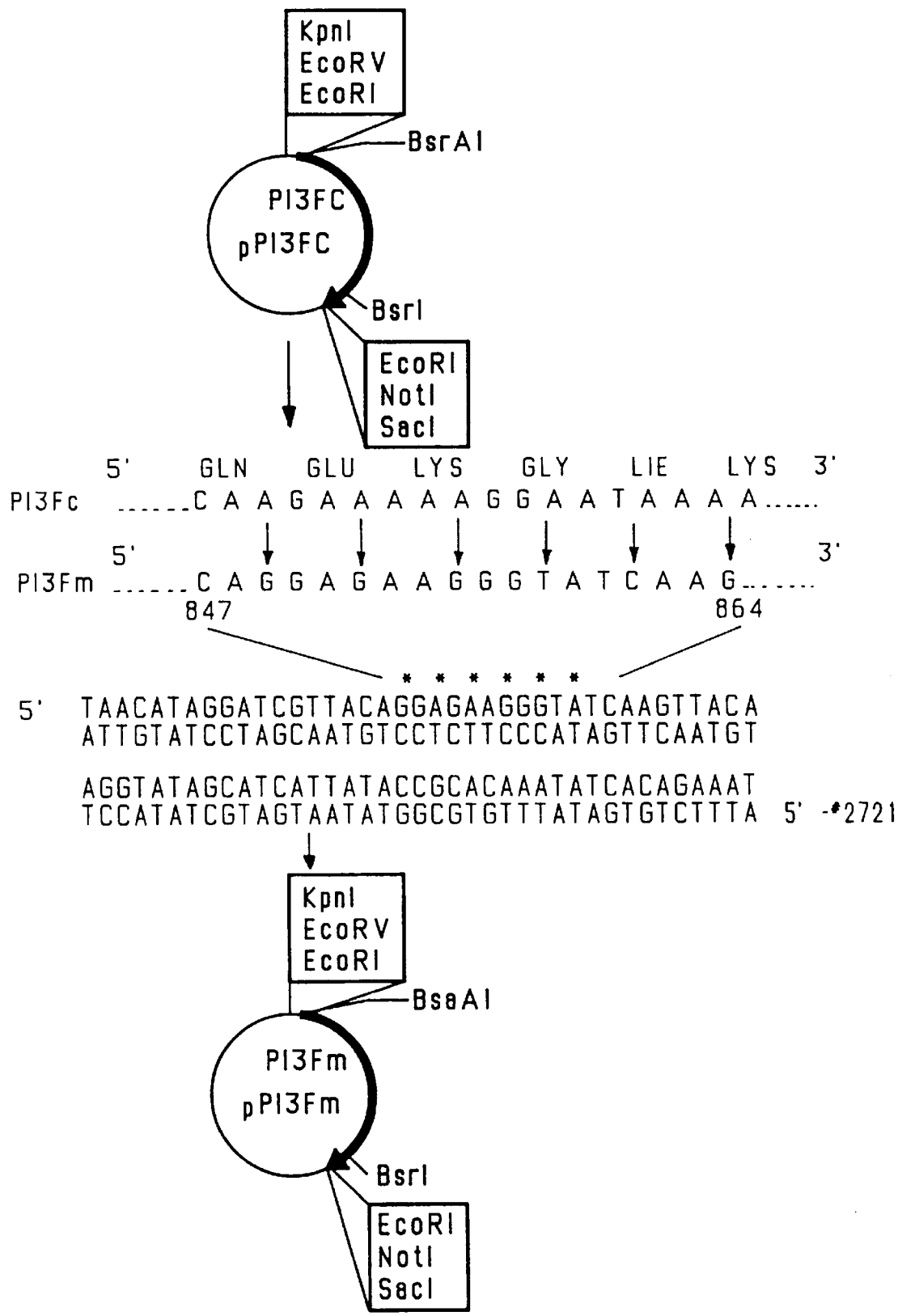
FIG.17. MUTAGENESIS OF THE PIV-3 F GENE

FIG. 18. CONSTRUCTION OF THE $F_{PIV3}$-$G_{RSV}$ CHIMERIC GENE

MULTIMERIC HYBRID GENE ENCODING A CHIMERIC PROTEIN WHICH CONFERS PROTECTION AGAINST PARAINFLUENZA VIRUS AND RESPIRATORY SYNCYTIAL VIRUS

This application is a continuation of application Ser. No. 08/001,554 filed Jan. 6, 1993 which application is now pending.

FIELD OF INVENTION

The present invention relates to the engineering and expression of multimeric hybrid genes containing sequences from the gene coding for immunogenic proteins or protein fragments of numerous pathogens.

BACKGROUND TO THE INVENTION

The advantage of the approach taken by the present invention is to produce single immunogens containing protective antigens from a range of pathogens. Such chimeras greatly simplify the development of combination vaccines, in particular, with the view ultimately to produce single dose multivalent vaccines. Multivalent vaccines are currently made by separately producing pathogens and/or their pertinent antigens and combining them in various formulations. This is a labour intensive, costly and complex manufacturing procedure. In contrast, the availability of a single immunogen capable of protecting against a range of diseases would solve many of the problems of multivalent vaccine production. Several chimeric immunogens of the type provided herein may be combined to decrease the number of individual antigens required in a multivalent vaccine.

Human Parainfluenza virus types 1,2,3 and Respiratory syncytial virus types A and B are the major viral pathogens responsible for causing severe respiratory tract infections in infants and young children. It is estimated that, in the United States alone, approximately 1.6 million infants under one year of age will have a clinically significant RSV infection each year and an additional 1.4 million infants will be infected with PIV-3. Approximately 4000 infants less than one year of age in the United States die each year from complications arising from severe respiratory tract disease caused by infection with RSV and PIV-3. The WHO and NIALD vaccine advisory committees ranked RSV number two behind HIV for vaccine development while the preparation of an efficacious PIV-3 vaccine is ranked in the top ten vaccines considered a priority for vaccine development.

Safe and effective vaccines for protecting infants against these viral infections are not available and are urgently required. Clinical trials have shown that formaldehyde-inactivated and live-attenuated viral vaccines failed to adequately protect vaccinees against these infections. In fact, infants who received the formalin-inactivated RSV vaccine developed more serious lower respiratory tract disease during subsequent natural RSV infection than did the control group. [Am. J. Epidemiology 89, 1969, p.405–421; J. Inf. Dis. 145, 1982, p.311–319]. Furthermore, RSV glycoproteins purified by immunoaffinity chromatography using elution at acid pH induced immunopotentiation in cotton rats. [Vaccine, 10(7), 1992, p.475–484]. The development of efficacious PIV-3 and RSV vaccines which do not cause exacerbated pulmonary disease in vaccinees following injection with wild-type virus would have significant therapeutic implications. It is anticipated that the development of a single recombinant immunogen capable of simultaneously protecting infants against diseases caused by infection with both Parainfluenza and Respiratory syncytial viruses could significantly reduce the morbidity and mortality caused by these viral infections.

It has been reported that a protective response against PIV-3 and RSV is contingent on the induction of neutralizing antibodies against the major viral surface glycoproteins. For PIV, these protective immunogens are the HN protein which has a molecular weight of 72 kDa and possesses both hemagglutination and neuraminidase activities and the fusion (F) protein, which has a molecular weight of 65 kDa and which is responsible for both fusion of the virus to the host cell membrane and cell-to-cell spread of the virus. For RSV, the two major immunogenic proteins are the 80 to 90 kDa G glycoprotein and the 70 kDa fusion (F) protein. The G and F proteins are thought to be functionally analogous to the PIV HN and F proteins, respectively. The PIV and RSV F glycoproteins are synthesized as inactive precursors (FO) which are proteolytically cleaved into N-terminal F2 and C-terminal F1 fragments which remain linked by disulphide bonds.

Recombinant surface glycoproteins from PIV and RSV have been individually expressed in insect cells using the baculovirus system [Ray et al., (1989), Virus Research, 12: 169–180; Coelingh et al., (1987), Virology, 160: 465–472; Wathen et al., (1989), J. of Inf. Dis. 159: 253–263] as well as in mammalian cells infected with recombinant poxviruses [Spriggs, et al., (1987), J. Virol. 61: 3416–3423; Stott et al., (1987), J. Virol. 61: 3855–3861]. Recombinant antigens produced in these systems were found to protect immunized cotton rats against live virus challenge. More recently, hybrid RSV F-G [Wathan et al., (1989), J. Gen Virol. 70: 2625–2635; Wathen, published International Patent application WO 89/05823] and PIV-3 F-HN [Wathen, published International Patent Application WO 89/10405], recombinant antigens have been engineered and produced in mammalian and insect cells. The RSV F-G hybrid antigen was shown to be protective in cotton rats [Wathan et al., (1989), J. Gen. Virol. 70: 2637–2644] although it elicited a poor anti-G antibody response [Connors et al., (1992), Vaccine 10: 475–484]. The protective ability of the PIV-3 F-HN protein was not reported in the published patent application. These antigens were engineered with the aim to protect against only the homologous virus, that is either RSV or PIV-3. However, it would be advantageous and economical to engineer and produce a single recombinant immunogen containing at least one protective antigen from each virus in order simultaneously to protect infants and young children against both PIV and RSV infections. The chimeric proteins provided herein for such purpose also may be administered to pregnant women or women of child bearing age to stimulate maternal antibodies to both PIV and RSV. In addition, the vaccine also may be administered to other susceptible individuals, such as the elderly.

SUMMARY OF INVENTION

In its broadest aspect, the present invention provides a multimeric hybrid gene, comprising a gene sequence coding for an immunogenic region of a protein from a first pathogen linked to a gene sequence coding for an immunogenic region of a protein from a second pathogen and to a chimeric protein encoded by such multimeric hybrid gene. Such chimeric protein comprises an immunogenic region of a protein from a first pathogen linked to an immunogenic region of a protein from a second pathogen.

The first and second pathogens are selected from bacterial and viral pathogens and, in one embodiment, may both be viral pathogens. Preferably, the first and second pathogens are selected from those causing different respiratory tract diseases, which may be upper and lower respiratory tract diseases. In a preferred embodiment, the first pathogen is parainfluenza virus and the second pathogen is respiratory syncytial virus. The PIV protein particularly is selected from PIV-3 F and HN proteins and the RSV protein particularly is selected from RSV G and F proteins. Another aspect of the invention provides cells containing the multimeric hybrid gene for expression of a chimeric protein encoded by the gene. Such cells may be bacterial cells, mammalian cells, insect cells, yeast cells or fungal cells. Further, the present invention provides a live vector for antigen delivery containing the multimeric hybrid gene, which may be a viral vector or a bacterial vector, and a physiologically-acceptable carrier therefor. Such live vector may form the active component of a vaccine against diseases caused by multiple pathogenic infections. Such vaccine may be formulated to be administered in an injectable form, intranasally or orally.

In an additional aspect of the present invention, there is provided a process for the preparation of a chimeric protein, which comprises isolating a gene sequence coding for an immunogenic region of a protein from a first pathogen; isolating a gene sequence coding for an immunogenic region of a protein from a second pathogen; linking the gene sequences to form a multimeric hybrid gene; and expressing the multimeric hybrid gene in a cellular expression system. The first and second pathogens are selected from bacterial and viral pathogens. Such cellular expression system may be provided by bacterial cells, mammalian cells, insect cells, yeast cells or fungal cells. The chimeric protein product of gene expression may be separated from a culture of the cellular expression system and purified.

The present invention further includes a vaccine against diseases caused by multiple pathogen infections, comprising the chimeric protein encoded by the multimeric hybrid gene and a physiologically-acceptable carrier therefor. Such vaccine may be formulated to be administered in an injectable form, intranasally or orally.

The vaccines provided herein may be used to immunize a host against disease caused by multiple pathogenic infections, particularly those caused by a parainfluenza virus and respiratory syncytial virus, by administering an effective amount of the vaccine to the host. As noted above, for human PIV and RSV, the host may be infants and young children, pregnant women as well as those of a child-bearing age, and other susceptible persons, such as the elderly.

The chimeric protein provided herein also may be used as a diagnostic reagent for detecting infection by a plurality of different pathogens in a host, using a suitable assaying procedure.

It will be appreciated that, while the description of the present invention which follows focuses mainly on a chimeric molecule which is effective for immunization against diseases caused by infection by PIV and RSV, nevertheless the invention provided herein broadly extends to any chimeric protein which is effected for immunization against diseases caused by a plurality of pathogens, comprising an antigen from each of the pathogens linked in a single molecule, as well as to genes coding for such chimeric molecules.

In this application, by the term "multimeric hybrid genes" we mean genes encoding antigenic regions of proteins from different pathogens and by the term "chimeric proteins" we mean immunogens containing antigenic regions from proteins from different pathogens.

BRIEF DESCRIPTION OF DRAWINGS

FIG. 3 shows the nucleotide (SEQ ID No: 3) and amino acid (SEQ ID No: 4) sequences of the PIV-3 HN gene and HN protein, respectively;

FIG. 5 shows the nucleotide (SEQ ID No: 5) and amino acid (SEQ ID No: 6) sequences of the RSV F gene and RSV F protein, respectively;

FIG. 7 shows the nucleotide (SEQ ID No: 7) and amino acid (SEQ ID No: 8) sequences of the RSV G gene and RSV G protein, respectively;

FIGS. 13A and 13B show immunoblots of cell lysates from Sf9 cells infected with recombinant baculoviruses;

FIG. 14 shows the steps involved in constructing a baculovirus transfer vector (pD2);

FIGS. 16A and 16B show an SDS-PAGE gel and immunoblot of purified $F_{RSV}$-$HN_{PIV-3}$ chimeric protein;

FIG. 17 illustrates mutagenesis of a PIV-3 F gene; and

FIG. 18 shows the steps involved in the construction of a chimeric $F_{PIV-3}$-$G_{RSV}$ gene.

GENERAL DESCRIPTION OF INVENTION

Figure 1:
FIG. 1 shows the nucleotide (SEQ ID No: 1) and amino acid (SEQ ID No: 2) sequence of a PCR-amplified PIV-3 F gene and F protein, respectively.

In the present invention, a chimeric molecule protective against two different major childhood diseases is provided. The present invention specifically relates to the formulation of various recombinant Parainfluenza virus (PIV)/Respiratory syncytial virus (RSV) immunogens to produce safe and efficacious vaccines capable of protecting infants and young children, as well as other susceptible individuals, against diseases caused by infection with both PIV and RSV. However, as described above, the present invention extends to the construction of multimeric hybrid genes containing genes coding for protective antigens from many pathogens. Such vaccines may be administered in any desired manner, such as a readily-injectable vaccine, intranasally or orally.

In the present invention, the inventors have specifically engineered several model PIV/RSV chimeric genes containing relevant sequences from selected genes coding for PIV-3 and RSV surface glycoproteins linked in tandem. All genes in the chimeric constructs described herein were obtained from recent clinical isolates of PIV-3 and RSV. The chimeric gene constructs may include gene sequences from either PIV-3 F or HN genes linked in tandem to either RSV F or G genes in all possible relative orientations and combinations.

The chimeric gene constructs provided herein may consist of either the entire gene sequences or gene segments coding for immunogenic and protective epitopes thereof. The natural nucleotide sequence of these genes may be modified by mutation while retaining antigenicity and such modifications may include the removal of putative pre-transcriptional terminators to optimize their expression in eukaryotic cells. The genes were designed to code for hybrid PIV-RSV surface glycoproteins linked in tandem in a single construct to produce gene products which elicit protective antibodies against both parainfluenza and respiratory syncytial viruses. Such multimeric hybrid genes consist of a gene sequence coding for a human PIV-3 F or HN protein or an immunogenic epitope-containing fragment thereof linked to a gene sequence coding for a human RSV G or F protein or an immunogenic epitope-containing fragment thereof. Specific gene constructs which may be employed include $F_{PIV-3}$-$F_{RSV}$, $F_{RSV}$-$HN_{PIV-3}$ and $F_{PIV-3}$-$G_{RSV}$ hybrid genes.

In addition, the present invention also extends to the construction of other multimeric genes, such as trimeric genes containing PIV and RSV genes or gene segments, linked in all possible relative orientations. For example:

$F_{PIV}$-$HN_{PIV}$-F or $G_{RSV}$ $F_{PIV}$-$F_{RSV}$-$G_{RSV}$ $HN_{PIV}$-$F_{RSV}$-$G_{RSV}$

The multimeric genes provided herein also may comprise at least one gene encoding at least one immunogenic and/or immunostimulating molecule.

The multimeric hybrid genes provided herein may be sub-cloned into appropriate vectors for expression in cellular expression systems. Such cellular expression systems may include bacterial, mammalian, insect and fungal, such as yeast, cells.

The chimeric proteins provided herein also may be presented to the immune system by the use of a live vector, including live viral vectors, such as recombinant poxviruses, adenoviruses, retroviruses, Semliki Forest viruses, and live bacterial vectors, such as Salmonella and mycobacteria (e.g. BCG).

Chimeric proteins, such as a PIV/RSV chimera, present in either the supernatants or cell lysates of transfected, transformed or infected cells then can be purified in any convenient manner.

To evaluate the immunogenicity and protective ability of the chimeric proteins, suitable experimental animals are immunized with either varying doses of the purified chimeric proteins, such as the PIV/RSV chimera, and/or live recombinant vectors as described above. Such chimeric proteins may be presented to the immune system by either the use of physiologically-acceptable vehicles, such as aluminum phosphate, or by the use of delivery systems, such as ISCOMS and liposomes. The chimeras also may be formulated to be capable of eliciting a mucosal response, for example, by conjugation or association with immunotargeting vehicles, such as the cholera toxin B subunit, or by incorporation into microparticles. The vaccines may further comprise means for delivering the multimeric protein specifically to cells of the immune system, such as toxin molecules or antibodies. To further enhance the immunoprotective ability of the chimeric proteins, they may be supplemented with other immunogenic and/or immunostimulating molecules. The chimeric PIV/RSV proteins specifically described herein may be formulated with an adjuvant, such as aluminum phosphate, to produce readily-injectable vaccines for protection against the diseases caused by both PIV-3 and RSV. The chimeric proteins also may be administered intranasally or orally. The chimeric proteins may be used in test kits for diagnosis of infection by PIV-3 and RSV.

The invention is not limited to the preparation of chimeric PIV-3 and RSV proteins, but is applicable to the production of chimeric immunogens composed of either the entire sequences or regions of the immunogenic proteins from at least two pathogens sequentially linked in a single molecule. Chimeric antigens also may be synthesized to contain the immunodominant epitopes of several proteins from different pathogens. These chimeric antigens may be useful as vaccines or as diagnostic reagents.

SEQUENCE IDENTIFICATION

Figure 9C:
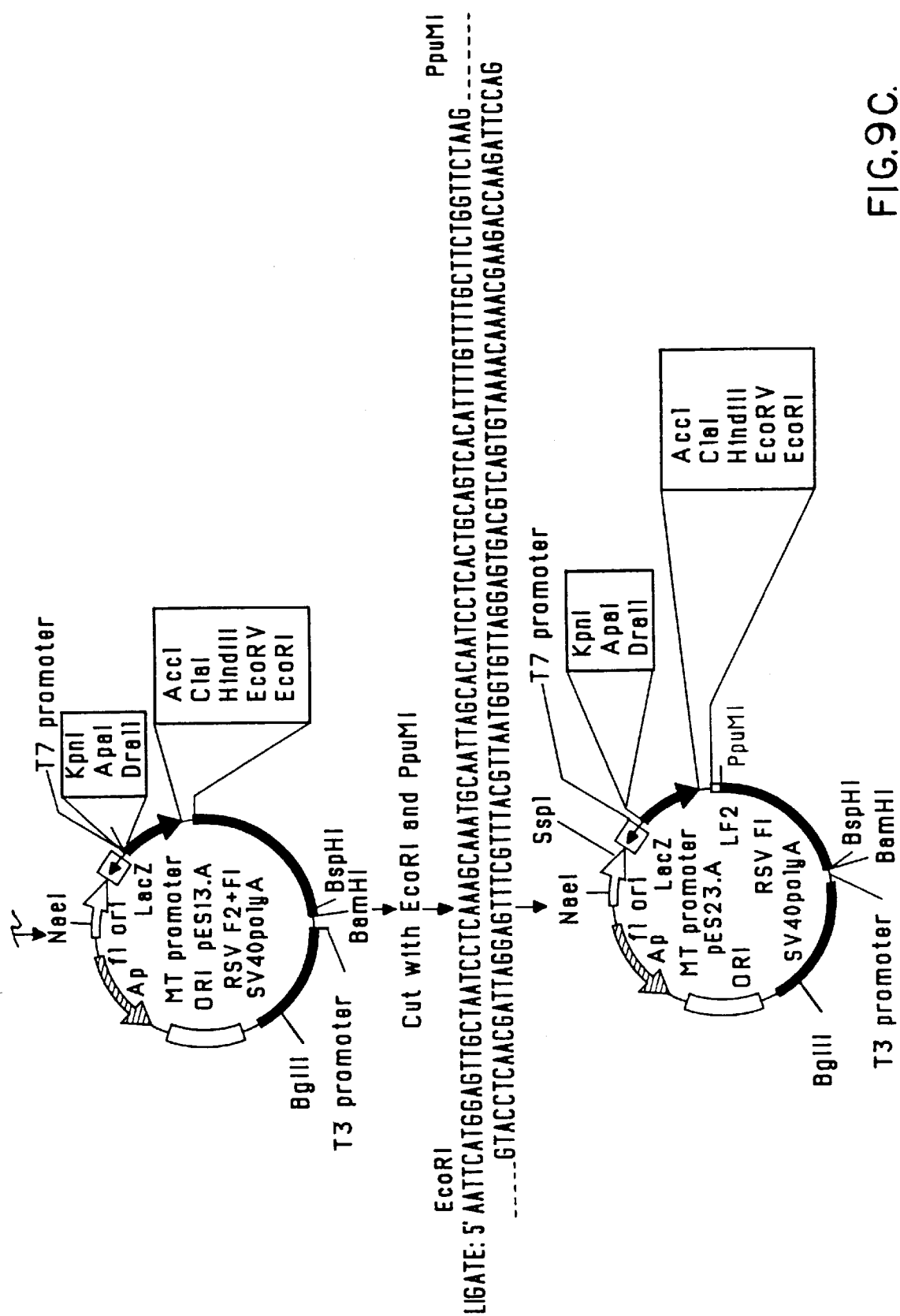
FIG. 9 shows the steps involved in the construction of an expression vector containing a chimeric $F_{PIV-3}$-$F_{RSV}$ gene.
Figure 9D:
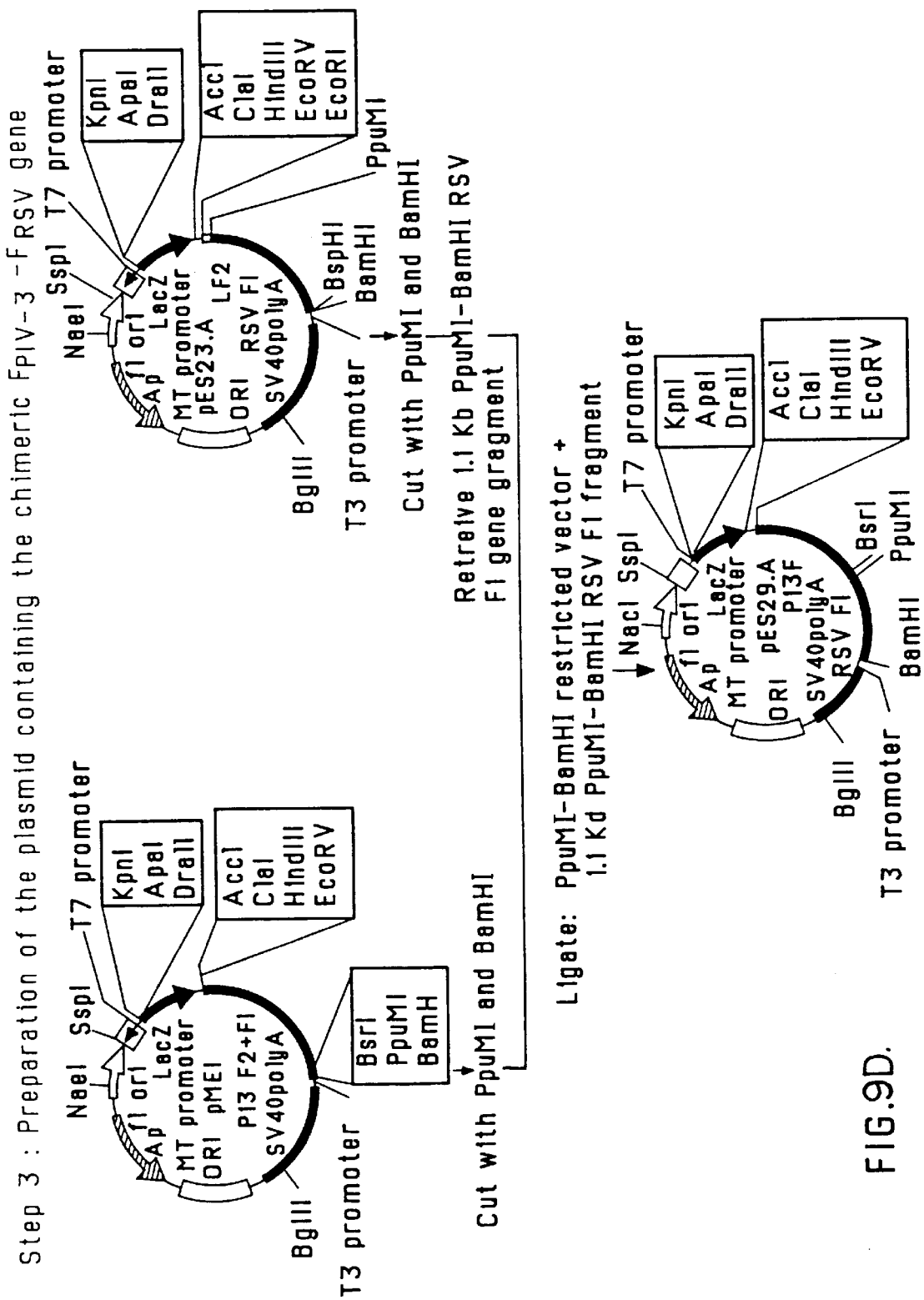
Figure 10A:
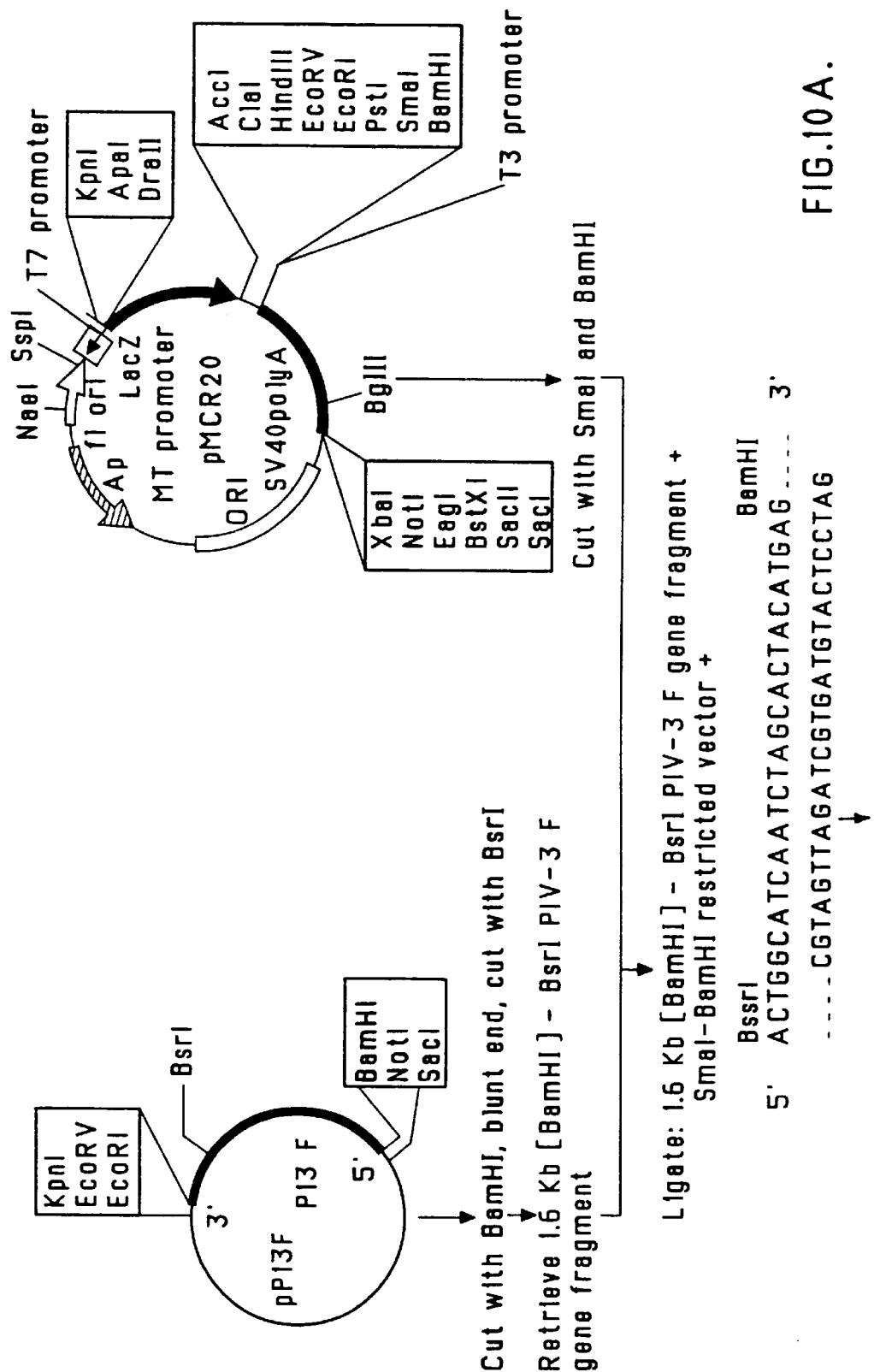
FIG. 10 shows the steps involved in the construction of an expression vector containing a $F_{PIV-3}$ gene lacking the 5'-untranslated sequence and transmembrane anchor and cytoplasmic tail coding regions.
Figure 11:
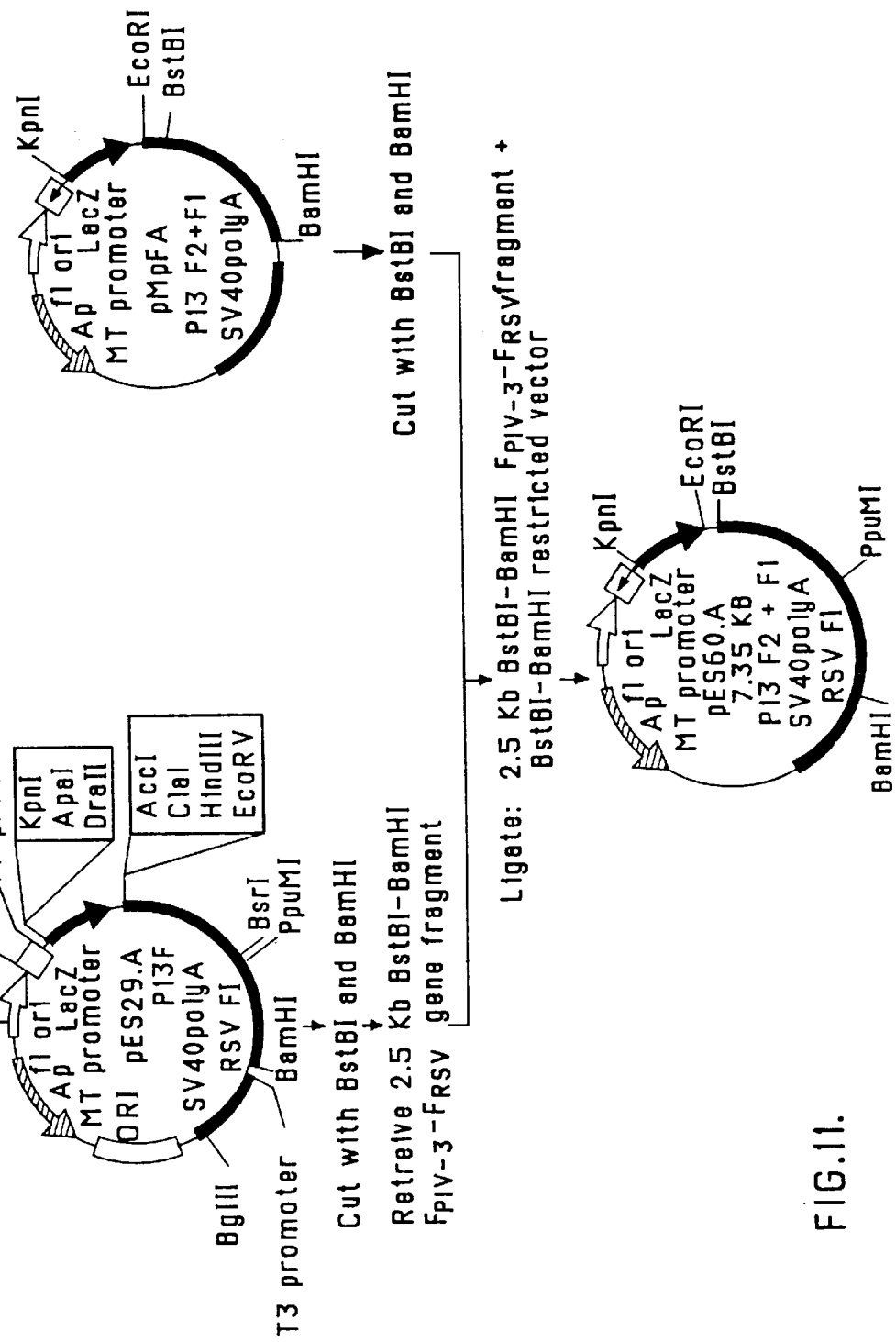
FIG. 11 shows the steps involved in the construction of an expression vector containing a chimeric $F_{PIV-3}$-$F_{RSV}$ gene containing a truncated PIV-3 F gene devoid of 5'-untranslated region linked to a truncated RSV F1 gene.
Figure 15B:
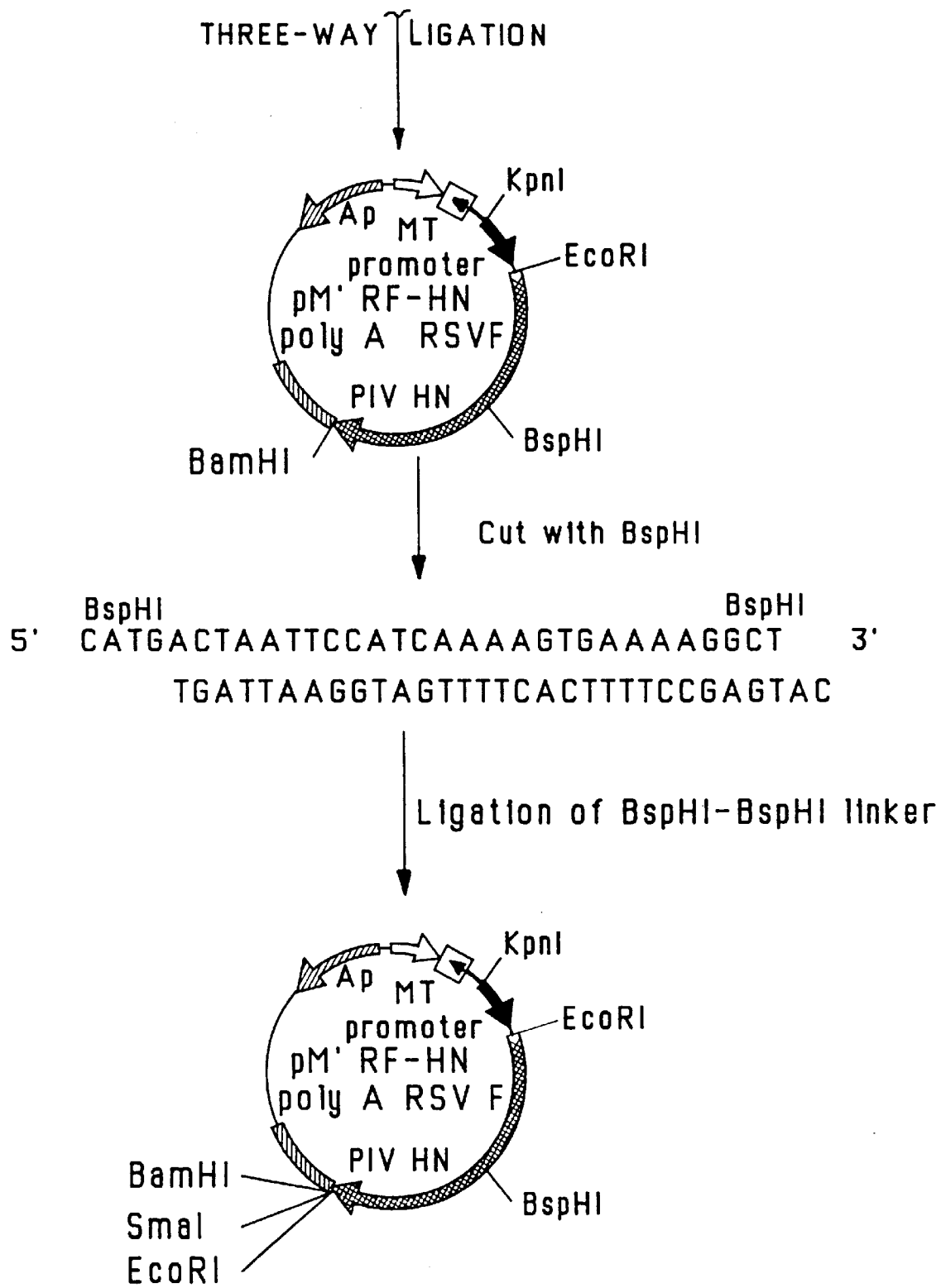
FIG. 15 shows the steps involved in construction of a chimeric $F_{RSV}$-$HN_{PIV-3}$ gene.

Several nucleotide and amino acid sequences are referred to in the disclosure of this application. The following table identifies the sequences and the location of the sequence:

| SEQ ID No. | Identification | Location |
|---|---|---|
| 1 | Nucleotide sequence for PCR-amplified PIV-3 F gene | FIG. 1, Example 1 |
| 2 | Amino acid sequence for PCR-amplified PIV-F protein | FIG. 1, Example 1 |
| 3 | Nucleotide sequence for PIV-3 HN qene | FIG. 3, Example 1 |
| 4 | Amino acid sequence for PIV-3 HN protein | FIG. 3, Example 1 |
| 5 | Nucleotide sequence for RSV F gene | FIG. 5, Example 1 |
| 6 | Amino acid sequenae for RSV F protein | FIG. 5, Example 1 |
| 7 | Nucleotide sequence for RSV G gene | FIG. 7, Example 1 |
| 8 | Amino acid sequence for RSV G protein | FIG. 7, Example 1 |
| 9 | BsrI - BamHI oligo-nucleotide cassette | FIG. 9, Example 2 |
| 10 | BspHI - BamHI oligo-nucleotide cassette | FIG. 9, Example 2 |
| 11 | EcoRI - Ppu MI oligo-nucleotide cassette | FIG. 9, Example 2 |
| 12 | BrsI - BamHI oligo-nucleotide cassette | FIG. 10, Example 3 |
| 13 | EcoRI -Bsr BI oligo-nucleotide cassette | FIG. 10, Example 3 |
| 14 | EcoRV - EcoRI oligo-nucleotide cassette | FIG. 11, Example 4 |
| 15 | EcORV - BamHI oligo-nucleotide cassette | FIG. 14, Example 8 |
| 16 | BspHI - BspHI oligo-nucleotide cassette | FIG. 15, Example 9 |
| 17 | Nucleotide sequence for PIV-3 F gene | Example 15 |
| 18 | Mutagenic oligo-nucleotide #2721 | FIG. 17, Example 15 |
| 19 | Nucleotide sequence for part of oligo-nucleotide #2721 | Example 15 |
| 20 | Oligonucleotide probe | Example 15 |

DEPOSIT INFORMATION

Certain plasmid DNAs described and referred to herein have been deposited with the American Type Culture Collection (ATCC) located at 10801 University Boulevard, Manassas, Va. 20110-2209, USA, pursuant to the Budapest Treaty and prior to the filing of this application. The deposited purified plasmids will become available to the public and all restrictions imposed on access to the deposits will be irrevocable removed. The deposit will be replaced if viable samples cannot be dispensed by the depository upon grant of this U.S. patent application or upon publication of its corresponding European patent application, whichever first occurs. The invention described and claimed herein is not to be limited in scope by the plasmid DNAs of the constructs deposited, since the deposited embodiment is intended only as an illustration of the invention. The following purified plasmids were deposited at the ATCC with the noted accession numbers on Dec. 17, 1992:

| Plasmid   | Example No. | Accession No. |
|-----------|-------------|---------------|
| pAC DR7   | 5           | 75387         |
| pD2RF-HN  | 9           | 75388         |
| pD2F-G    | 16          | 75389         |

Any equivalent plasmids that can be used to produce equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods for cloning and sequencing the PIV-3 and RSV genes as well as the procedures for sub-cloning the genes into appropriate vectors and expressing the gene constructs in mammalian and insect cells are not explicitly described in this disclosure but are well within the scope of those skilled in the art.

Example 1

This Example outlines the strategy used to clone and sequence the PIV-3 F, HN and RSV F, G genes (from a type A isolate). These genes were used in the construction of the $F_{PIV-3}$-$F_{RSV}$, $F_{RSV}$-$HN_{PIV-3}$, and $F_{PIV-3}$-$G_{RSV}$ chimeric genes detailed in Examples 2 to 4, 9 and 15, respectively.

Two PIV-3 F gene clones initially were obtained by PCR amplification of cDNA derived from viral RNA extracted from a recent clinical isolate of PIV-3. Two other PIV-3 F gene clones as well as the PIV-3 HN, RSV F and RSV G genes were cloned from a cDNA library prepared from mRNA isolated from MRC-5 cells infected with clinical isolates of either PIV-3 or RSV (type A isolate). The PIV-3 F (both PCR amplified and non-PCR amplified), PIV-3 HN, RSV F and RSV G gene clones were sequenced by the dideoxynucleotide chain termination procedure. Sequencing of both strands of the genes was performed by a combination of manual and automated sequencing.

Figure 2:
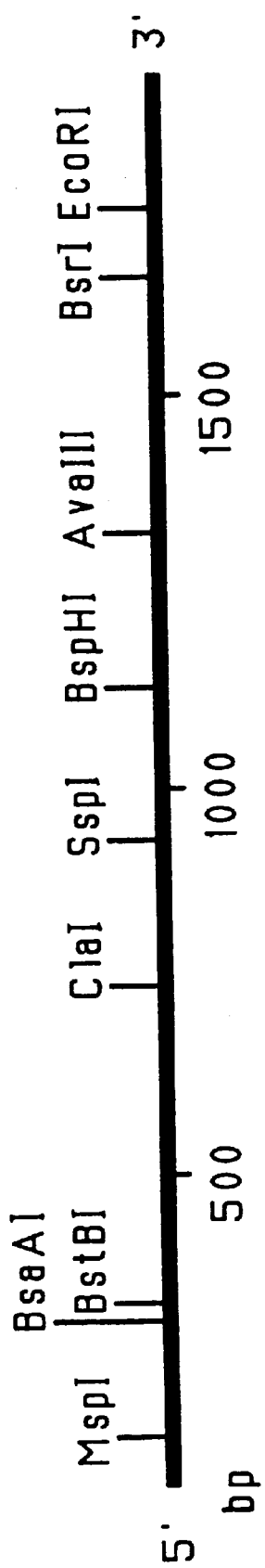
FIG. 2 shows the restriction map of the PIV-3 F gene.

The nucleotide (SEQ ID No: 1) and amino acid (SEQ ID No: 2) sequences of the PCR amplified PIV-3 F gene and F protein, respectively, are presented in FIG. 1 and the restriction map of the gene is shown in FIG. 2. Sequence analysis of the 1844 nucleotides of two PCR amplified PIV-3 F gene clones confirmed that the clones were identical. Comparison of the coding sequence of the PCR-amplified PIV-3 F gene clone with that of the published PIV-3 F gene sequence revealed a 2.6% divergence in the coding sequence between the two genes resulting in fourteen amino acid substitutions.

The nucleotide sequence of the non-PCR amplified PIV-3 F gene clone differed from the PCR amplified gene clone in the following manner: the non-PCR amplified clone had ten additional nucleotides (AGGACAAAAG-SEQ ID NO: 38) at the 5' untranslated region of the gene and differed at four positions, 8 (T in PCR-amplified gene to C in non-PCR amplified gene), 512 (C in PCR-amplified gene to T in non-PCR amplified gene), 518 (G in PCR-amplified gene to A in non-PCR amplified gene) and 1376 (A in PCR-amplified gene to G in non-PCR amplified gene). These changes resulted in three changes in the amino acid sequence of the F protein encoded by the non-PCR amplified PIV-3 F gene. Serine (position 110), glycine (position 112), and aspartic acid (position 398) in the primary amino acid sequence of the F protein encoded by the PCR amplified PIV-3 F gene was changed to phenylalanine (position 110), glutamic acid (position 112) and glycine (position 398), respectively, in the primary amino acid sequence of the F protein encoded by the PCR amplified clone.

Figure 4:
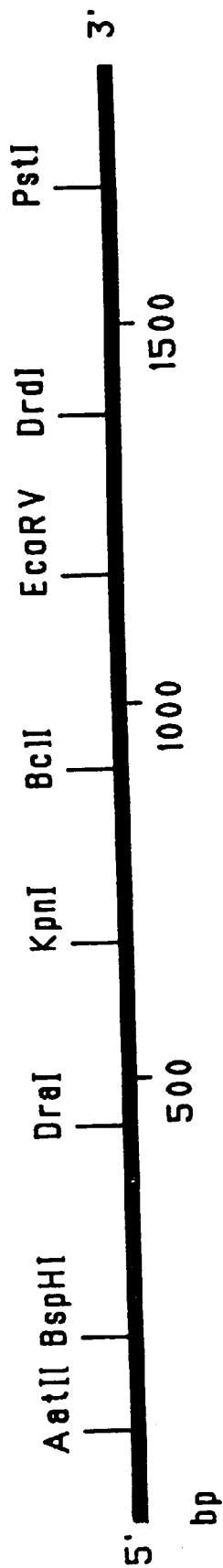
FIG. 4 shows the restriction map of the PIV-3 HN gene.

FIG. 3 shows the nucleotide (SEQ ID No: 3) and amino acid (SEQ ID No: 4) sequences of the PIV-3 HN gene and protein, respectively and the restriction map of the gene is presented in FIG. 4. Analysis of the 1833 nucleotide sequence from two HN clones confirmed that the sequences were identical. A 4.4% divergence in the coding sequence of the PIV-3 HN gene was noted when the S sequence was compared to the published PIV-3 HN coding sequence. This divergence resulted in seventeen amino acid substitutions in the amino acid sequence of the protein encoded by the PIV-3 HN gene.

Figure 6:
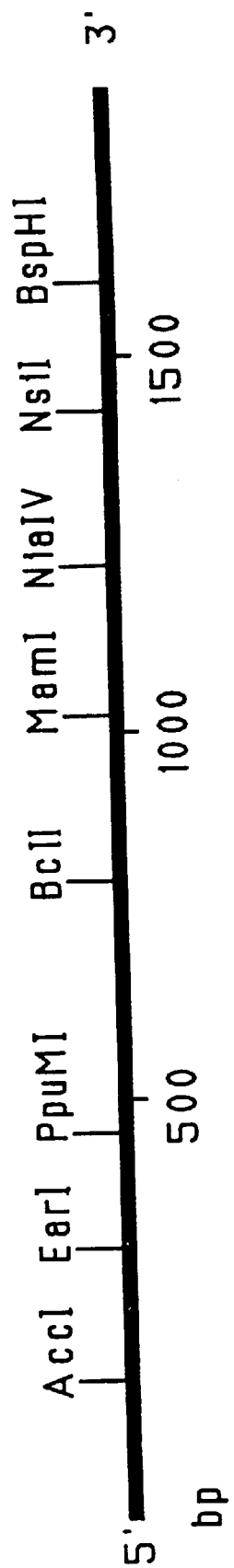
FIG. 6 shows the restriction map of the RSV F gene.

The nucleotide (SEQ ID No: 5) and amino acid (SEQ ID No: 6) sequences of the RSV F gene and RSV F protein, respectively, are shown in FIG. 5 and the restriction map of the gene is shown in FIG. 6. Analysis of the 1886 nucleotide sequence from two RSV F clones verified complete sequence homology between the two clones. Comparison of this nucleotide sequence with that reported for the RSV F gene revealed approximately 1.8% divergence in the coding sequence resulting in eleven amino acid substitutions.

Figure 8:
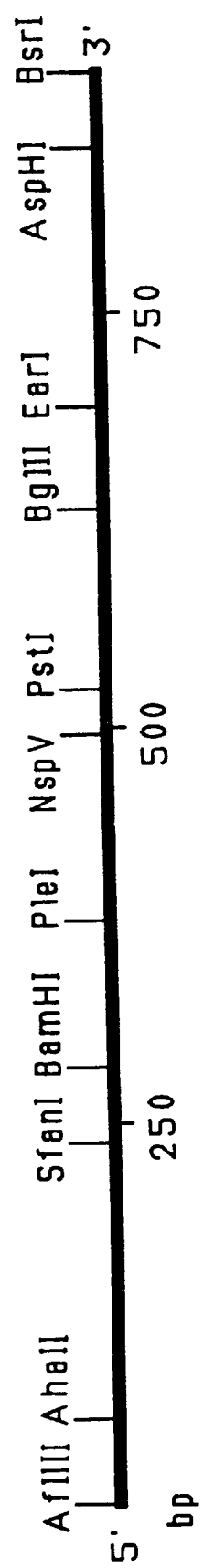
FIG. 8 shows the restriction map of the RSV G gene.

The nucleotide (SEQ ID No: 7) and amino acid (SEQ ID No: 8) sequences of the RSV G gene and RSV G protein, respectively, are presented in FIG. 7 while the restriction map of the gene is outlined in FIG. 8. Comparison of the 920 nucleotide sequence of the G gene clone with the published G sequence (type A isolate) revealed a 4.2% divergence in the nucleotide sequence and a 6.7% divergence in the amino acid sequence of the gene product. This divergence resulted in twenty amino acid substitutions.

The full-length PIV-3 F (non-PCR amplified), PIV-3 HN, RSV F and RSV G genes were cloned into λgtll and subcloned into the multiple cloning site of a Bluescript M13-SK vector, either by blunt end ligation or using appropriate linkers. The PCR-amplified PIV-3 F gene was directly cloned into the Bluescript vector. The cloning vectors containing the PIV-3 F-PCR amplified, PIV-3 F non-PCR amplified, PIV-3 HN, RSV F and RSV G genes were named pPI3F, pPI3Fc, pPIVHN, pRSVF and pRSVG, respectively.

Example 2

This Example illustrates the construction of a Bluescript-based expression vector (pMCR20) containing the chimeric $F_{PIV-3}$-$F_{RSV}$ gene. This chimeric gene construct contains the 5' untranslated region of the PIV-3 F gene but lacks the hydrophobic anchor and cytoplasmic tail coding regions of both the PIV-3 and RSV F genes. The steps involved in the construction of this plasmid are summarized in FIG. 9.

To prepare the PIV-3 portion of the chimeric gene (FIG. 9, step 1), the full length PIV-3 gene lacking the transmembrane region and cytoplasmic tail coding regions was retrieved from plasmid pPI3F by cutting the polylinker with BamHI, blunt-ending the linearized plasmid with Klenow polymerase and cutting the gene with BsrI. A BsrI-BamHI oligonucleotide cassette (SEQ ID No: 9) containing a PpuMI site and three successive translational stop codons were ligated to the truncated 1.6 Kb [BamHI]-BsrI PIV-3 F gene fragment and cloned into the EcoRV-BamHI sites of a Bluescript M13-SK expression vector containing the human methallothionen promoter and the poly A and IVS sequences of the SV40 genome (designated pMCR20), to generate plasmid pME1.

To engineer the RSV F gene component of the chimeric construct (FIG. 9, step 2), the RSV F gene lacking the transmembrane region and cytoplasmic tail coding regions was retrieved from plasmid pRSVF by cutting the polylinker with EcoRI and the gene with BspHI. A synthetic BspHI-BamHI oligonucleotide cassette (SEQ ID No: 10) containing three successive translational stop codons was ligated to the 1.6 Kb truncated RSV F gene and cloned into the EcoRI-BamHI sites of the Bluescript based expression vector, pMCR20 to produce plasmid pES13A. Plasmid pES13A then was cut with EcoRI and PpuMI to remove the leader and F2 coding sequences from the truncated RSV F gene. The leader sequence was reconstructed using an EcoRI-PpuMI oligocassette (SEQ ID No: 11) and ligated to the RSV F1 gene segment to generate plasmid pES23A.

To prepare the chimeric FpIV-3-FRsv gene (FIG. 9, step 3) containing the 5' untranslated region of the PIV-3 F gene linked to the truncated RSV F1 gene fragment, plasmid pME1 (containing the 1.6 Kb truncated PIV-3 F gene) first was cut with PpuMI and BamHI. The PpuMI-BamHI restricted pME1 vector was dephosphorylated with intestinal alkaline phosphatase. The 1.1 Kb RSV F1 gene fragment was retrieved from plasmid pES23A by cutting the plasmid with PpuMI and BamHI. The 1.1 Kb PpuMI-BamHI RSV F1 gene fragment was cloned into the PpuMI-BamHI sites of the dephosphorylated pME1 vector to generate plasmid pES29A. This chimeric gene construct contains the 5' untranslated region of the PIV-3 F gene but lacks the nucleotide sequences coding for the hydrophobic anchor domains and cytoplasmic tails of both the PIV-3 and RSV F proteins.

Example 3

This Example illustrates the construction of a Bluescript-based expression vector containing the PIV-3 F gene lacking both the 5' untranslated and transmembrane anchor and cytoplasmic tail coding regions. The steps involved in constructing this plasmid are outlined in FIG. 10.

Plasmid pPI3F containing the full length PIV-3 F gene was cut with BamHI, blunt ended with Klenow polymerase and then cut with BsrI to remove the transmembrane and cytoplasmic tail coding regions. The Bluescript-based expression vector, pMCR20, was cut with SmaI and BamHI. A synthetic BsrI-BamHI oligonucleotide cassette (SEQ ID No: 12) containing a translational stop codon was ligated with the 1.6 Kb blunt ended-BsrI PIV-3 F gene fragment to the SmaI-BamHI restricted pMCR20 vector to produce plasmid PMpFB. The PIV-3 F gene of this construct lacked the DNA fragment coding for the transmembrane and cytoplasmic anchor domains but contained the 5' untranslated region. To engineer a plasmid containing the PIV-3 F gene devoid of both the 5' untranslated region and the DNA fragment coding for the hydrophobic anchor domain, plasmid pMpFB was cut with EcoRI and BstBI. An EcoRI-BstBI oligocassette (SEQ ID No: 13) containing the sequences to reconstruct the signal peptide and coding sequences removed by the EcoRI-BstBI cut was ligated to the EcoRI-BstBI restricted pMpFB vector to produce plasmid pMpFA.

Example 4

This Example illustrates the construction of the chimeric $F_{PIV-3}$-$F_{RSV}$ gene composed of the truncated PIV-3 F gene devoid of the 5' untranslated region linked to the truncated RSV F1 gene. The steps involved in constructing this plasmid are summarized in FIG. 11.

To prepare this chimeric gene construct, plasmid pES29A (Example 2) was cut with BstBI and BamHI to release the 2.5 Kb BstBI-BamHI PI3-3 F-RSV F1 chimeric gene fragment. This BstBI-BamHI fragment was isolated from a low melting point agarose gel and cloned into the BstBI-BamHI sites of the dephosphorylated vector pMpFA to produce plasmid pES60A. This construct contained the PIV-3 F gene lacking both the 5' untranslated region and the hydrophobic anchor and cytoplasmic tail coding sequences linked to the F1 coding region of the truncated RSV F gene. This chimeric gene was subsequently subcloned into the baculovirus transfer vector (see Example 5).

Example 5

Figure 12B:
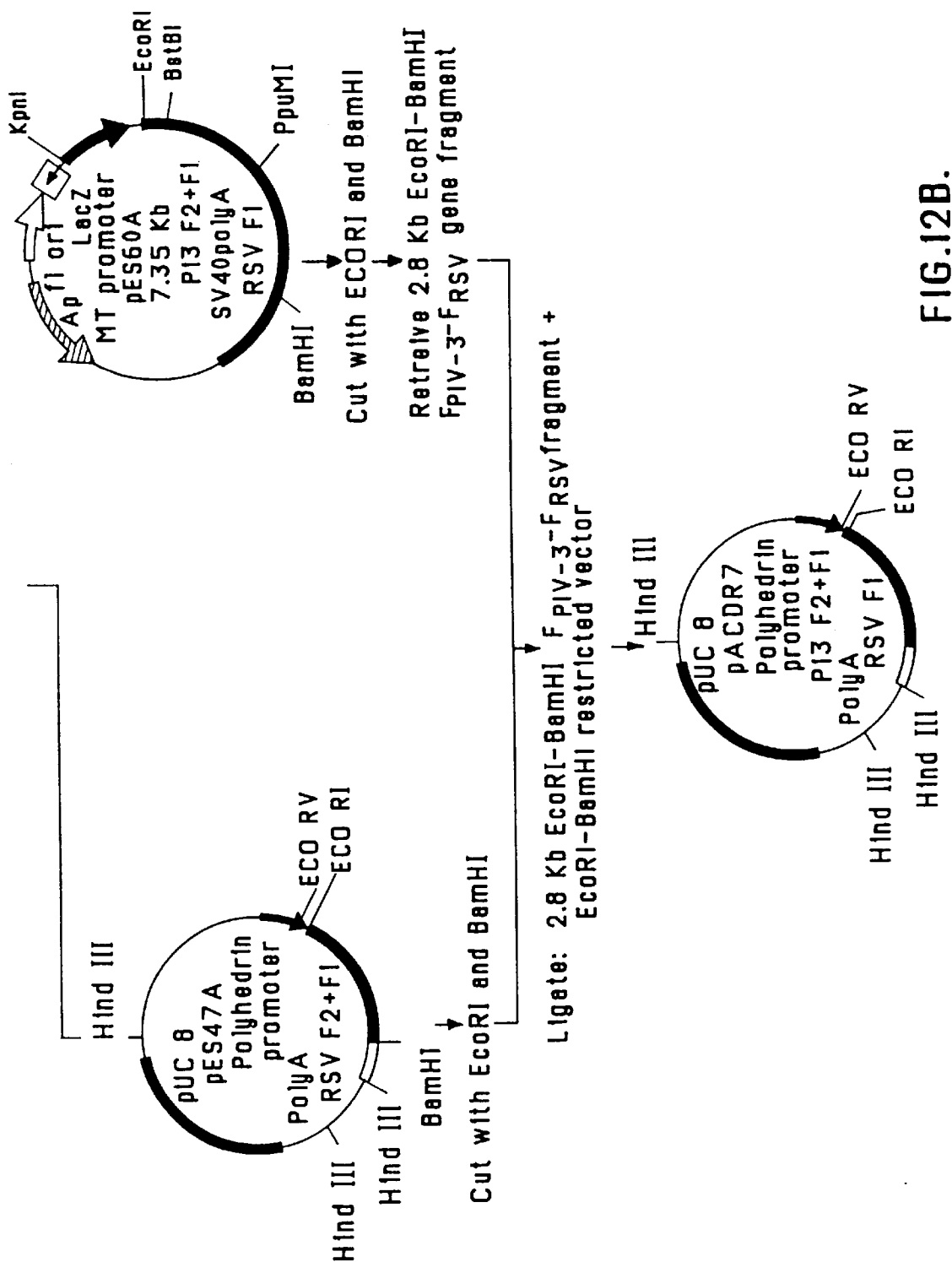
FIG. 12 shows the steps involved in construction of a modified pAC 610 baculovirus expression vector containing a chimeric $F_{PIV-3}$-$F_{RSV}$ gene consisting of the PIV-3 F gene lacking both the 5'-untranslated sequence as well as transmembrane and cytoplasmic tail coding region linked to the truncated RSV F1 gene.

This Example illustrates the construction of the modified pAC 610 baculovirus transfer vector containing the native polyhedrin promoter and the chimeric $F_{PIV-3}$-$F_{RSV}$ gene consisting of the PIV-3 F gene lacking both the 5' untranslated sequence and the nucleotide sequence coding for the hydrophobic anchor domain and cytoplasmic tail linked to the truncated RSV F1 gene. Construction of this plasmid is illustrated in FIG. 12.

The pAC 610 baculovirus expression vector was modified to contain the native polyhedrin promoter in the following manner. Vector pAC 610 was cut with EcoRV and BamHI. The 9.4 Kb baculovirus transfer vector lacking the EcoRV-BamHI DNA sequence was isolated from a low melting point agarose gel and treated with intestinal alkaline phosphatase. In a 3-way ligation, an EcoRV-EcoRI oligonucleotide cassette (SEQ ID No: 14) containing the nucleotides required to restore the native polyhedrin promoter was ligated with the 1.6 Kb EcoRI-BamHI truncated RSV F gene fragment isolated from construct pES13A (Example 2, step 2) and the EcoRV-BamHI restricted pAC 610 phosphatased vector to generate plasmid pES47A. To prepare the pAC 610 based expression vector containing the chimeric $F_{PIV-3}$-$F_{RSV}$ gene, plasmid pES47A was first cut with EcoRI and BamHI to remove the 1.6 Kb truncated RSV F gene insert. The 2.8 Kb $F_{PIV-3}$-$F_{RSV}$ chimeric gene was retrieved by cutting plasmid pES60A (Example 4) with EcoRI and BamHI. The 2.8 Kb EcoRI-BamHI chimeric gene was ligated to the EcoRI-BamHI restricted pES47A vector to generate plasmid pAC DR7 (ATCC 75387).

Example 6

This Example outlines the preparation of plaque-purified recombinant baculoviruses containing the chimeric $F_{PIV-3}$-$F_{RSV}$ gene.

Spodoptera frugiperda (Sf9) cells were co-transfected with 1.0 μg wild-type AcMNPV DNA and 2.5 μg of $pp_{IV-3}$-FRSV plasmid DNA (plasmid pAC DR7-Example 5). Putative recombinant baculoviruses (purified once by serial dilution) containing the $F_{PIV-3}$-$F_{RSV}$ chimeric gene were identified by dot-blot hybridization. Lysates of insect cells infected with the putative recombinant baculoviruses were probed with the $^{32}$P-labelled $F_{PIV-3}$-$F_{RSV}$ chimeric gene insert. Recombinant baculoviruses were plaque-purified twice before being used for expression studies. All procedures were carried out according to the protocols outlined by M. D. Summers and G. E. Smith in "A Manual of Methods for Baculovirus Vectors and Insect Cell Culture Procedures", Texas Agricultural Experiment Station, Bulletin 1555, 1987.

Example 7

This Example illustrates the presence of the chimeric $F_{PIV-3}$-$F_{RSV}$ protein in supernatants and cell lysates of infected Sf9 cells.

Insect cells were infected with the plaque-purified recombinant baculoviruses prepared as described in Example 6 at a m.o.i. of 8. Concentrated supernatants from cells infected with the recombinant viruses were positive in a PIV-3 F specific ELISA. In addition, when lysates from $^{35}$S-methioninelabelled infected cells were subjected to SDS-polyacrylamide gel electrophoresis and gels were analyzed by autoradiography, a strong band with apparent molecular weight of approximately 90 kDa was present in lysates of cells infected with the recombinant viruses but was absent in the lysates from wild-type infected cells. The presence of the chimeric $F_{PIV-3}$-$F_{RSV}$ protein in the lysates of cells infected with the recombinant baculoviruses was confirmed further by Western blot analysis using monospecific anti-PIV-3 F and anti-RSV F antisera and/or monoclonal antibodies (Mabs). Lysates from cells infected with the recombinant baculoviruses reacted with both anti-PIV-3 and anti-RSV antisera in immunoblots. As shown in the immunoblot of FIG. 13, lysates from cells infected with either the RSV F or $F_{PIV-3}$-$F_{RSV}$ recombinant baculoviruses reacted positively with the anti-F RSV Mab. As expected, lysates from cells infected with wild type virus did not react with this Mab. In addition, only lysates from cells infected with the chimeric $F_{PIV-3}$-$F_{RSV}$ recombinant viruses reacted with the anti-PIV-3 $F_1$ antiserum.

Example 8

This Example illustrates modification of the baculovirus transfer vector pVL1392 (obtained from Invitrogen), wherein the polyhedrin ATG start codon was converted to ATT and the sequence CCG was present downstream of the polyhedrin gene at positions +4,5,6. Insertion of a structural gene several base pairs downstream from the ATT codon is known to enhance translation. The steps involved in constructing this modified baculovirus transfer vector are outlined in FIG. 14.

The baculovirus expression vector pVL1392 was cut with EcoRV and BamHI. The 9.5 kb restricted pVL1392 vector was ligated to an EcoRV-BamHI oligonucleotide cassette (SEQ ID No: 15) to produce the pD2 vector.

Example 9

This Example illustrates the construction of the pD2 baculovirus expression vector containing the chimeric $F_{RSV}$-$HN_{PIV-3}$ gene consisting of the truncated RSV F and PIV-3 HN genes linked in tandem. The steps involved in constructing this plasmid are summarized in FIG. 15.

To engineer the $F_{RSV}$-$HN_{PIV-3}$ gene, the RSV F gene lacking the nucleotide sequence coding for the transmembrane domain and cytoplasmic tail of the RSV F glycoprotein was retrieved from plasmid PRSVF (Example 1) by cutting the polylinker with EcoRI and the gene with BspHI. The PIV-3 HN gene devoid of the DNA fragment coding for the hydrophobic anchor domain was retrieved from plasmid pPIVHN (Example 1) by cutting the gene with BspHI and the polylinker with BamHI. The 1.6 Kb EcoRI-BspHI RSV F gene fragment and the 1.7 Kb BspHI-BamHI PIV-3 HN gene fragment were isolated from low melting point agarose gels. For cloning purposes, the two BspHI sites in the Bluescript based mammalian cell expression vector, pMCR20, were mutated. Mutations were introduced in the BspHI sites of the pMCR20 by cutting the expression vector with BspHI, treating both the BspHI restricted vector and the 1.1 Kb fragment released by the BspHI cut with Klenow polymerase and ligating the blunt-ended 1.1 Kb fragment to the blunt-ended Bluescript-based expression vector to generate plasmid pM'. Since insertion of the 1.1 Kb blunt-end fragment in the mammalian cell expression vector in the improper orientation would alter the $Amp^r$ gene of the Bluescript-based expression vector, only colonies of HB101 cells transformed with the pM' plasmid DNA with the 1.1 Kb blunt-ended fragment in the proper orientation could survive in the presence of ampicillin. Plasmid DNA was purified from ampicillin-resistant colonies of HB101 cells transformed with plasmid PM' by equilibrium centrifugation in cesium chloride-ethidium bromide gradients. The 1.6 Kb EcoRI-BspHI RSV F and 1.7 Kb BspHI-BamHI PIV-3 HN gene fragments were directly cloned into the EcoRI-BamHI sites of vector pM' in a 3-way ligation to generate plasmid pM' RF-HN.

To restore specific coding sequences of the RSV F and PIV-3 HN genes removed by the BspHI cut, a BspHI-BspHI oligonucleotide cassette (SEQ ID No: 16) containing the pertinent RSV F and PIV-3 HN gene sequences was ligated via the BspHI site to the BspHI-restricted plasmid pM' RF-HN to produce plasmid pM RF-HN. Clones containing the BspHI-BspHI oligonucleotide cassette in the proper orientation were identified by sequence analysis of the oligonucleotide linker and its flanking regions.

To clone the chimeric $F_{RSV}$-$HN_{PIV-3}$ gene into the baculovirus expression vector pD2 (Example 8), the $F_{RSV}$-$HN_{PIV-3}$ truncated gene first was retrieved from plasmid pM RF-HN by cutting the plasmid with EcoRI. The 3.3 Kb $F_{RSV}$-$HN_{PIV-3}$ gene then was cloned into the EcoRI site of the baculovirus transfer vector plasmid pD2 to generate plasmid pD2 RF-HN (ATCC 75388). Proper orientation of the 3.3 Kb EcoRI $F_{RSV}$-$HN_{PIV-3}$ chimeric gene insert in plasmid pD2 RF-HN was confirmed by sequence analysis.

Example 10

This Example outlines the preparation of plaque-purified recombinant baculoviruses containing the chimeric $F_{RSV}$-$HN_{PIV-3}$ gene.

Spodoptera frugiperda (Sf9) cells were co-transfected with 1 μg wild-type AcNPV DNA and 2 μg of $F_{RSV}$-$HN_{PIV-3}$ plasmid DNA (plasmid pD2 RF-HN-Example 9). Putative recombinant baculoviruses (purified once by serial dilution) containing the $F_{RSV}$-$HN_{PIV-3}$ chimeric gene were identified by dot-blot hybridization. Lysates of insect cells infected with the putative recombinant baculoviruses were probed with the $^{32}$P-labelled RSV F or PTV-3 HN gene oligonucleotide probes. Recombinant baculoviruses were plaque-purified three times before being used for expression studies.

All procedures were carried out according to the protocols outlined by Summers and Smith (Example 6).

Example 11

This Example illustrates the presence of the chimeric $F_{RSV}$-$HN_{PIV-3}$ protein in supernatants of infected Sf9 and High 5 cells.

Insect cells (Sf9 and High 5), maintained in serum free medium EX401, were infected with the plaque purified recombinant baculoviruses of Example 10 at a m.o.i. of 5 to 10 pfu/cell. Supernatants from cells infected with the recombinant baculoviruses tested positive for expressed protein in both the RSV-F and PIV-3 HN specific ELISAS. In addition, supernatants from infected cells reacted positively with both an anti-F RSV monoclonal antibody and anti-HN peptide antisera on immunoblots. A distinct band of approximately 105 kDa was present in the immunoblots. These results confirm the secretion of the chimeric $F_{RSV}$-$HN_{PIV-3}$ protein into the supernatant of Sf9 and High 5 cells infected with the recombinant baculoviruses.

Example 12

This Example illustrates the purification of the chimeric $F_{RSV}$-$HN_{PIV-3}$ protein from the supernatants of infected High 5 cells.

High 5 cells, maintained in serum free medium, were infected with the plaque purified recombinant baculoviruses of Example 10 at a m.o.i of 5 pfu/cell. The supernatant from virus infected cells was harvested 2 days post-infection. The soluble $F_{RSV}$-$HN_{PIV-3}$ chimeric protein was purified from the supernatants of infected cells by immunoaffinity chromatography using an anti-HN PIV-3 monoclonal antibody. The anti-HN monoclonal antibody was coupled to CNBr-activated Sepharose 4B by conventional techniques. The immunoaffinity column was washed with 10 bed volumes of washing buffer (10 mM Tris-HCl pH 7.5, 150 mM NaCl, 0.02% v/v TRITON X-100(Trademark for a non-ionic detergent) which is octadienyl phenol (ethylene glycol)$_{10}$ prior to use. After sample loading, the column was washed with 10 bed volumes of washing buffer followed by 3 bed volumes of high salt buffer (10 mm Tris-HCl pH 7.5, 500 mM NaCl, 0.02% v/v Triton-X 100). The chimeric $F_{RSV}$-$HN_{PIV-3}$ protein was eluted from the immunoaffinity column with 100 MM glycine, pH 2.5, in the presence of 0.02% TRITON X-100. Eluted protein was neutralized immediately with 1M Tris-HCl, pH 10.7.

Polyacrylamide gel electrophoretic analysis (FIG. 16, panel A) of the immunoaffinity-purified $F_{RSV}$-$HN_{PIV-3}$ protein revealed the presence of one major protein band with an apparent molecular weight of 105 kDa. The purified protein reacted with both an anti-RSV F monoclonal antibody and anti-HN peptide antisera on immunoblots (FIG. 16, panel B, lanes 1 and 2, respectively).

Example 13

This Example illustrates the immunogenicity of the $F_{RSV}$-$HN_{PIV-3}$ protein in guinea pigs.

Groups of four guinea pigs were injected intramuscularly with either 1.0 or 10.0 µg of the chimeric $F_{RSV}$-$HN_{PIV-3}$ protein purified as described in Example 12 and adjuvanted with aluminum phosphate. Groups of control animals were immunized with either placebo, or live PIV-3 or RSV (administered intranasally). Guinea pigs were bled 2 and 4 weeks after the primary injection and boosted at 4 weeks with an equivalent dose of the antigen formulation. Serum samples also were taken 2 and 4 weeks after the booster dose. To assess the ability of the chimeric protein to elicit PIV-3 and RSV-specific antibody responses, sera samples were analyzed for the presence of PIV-3 specific hemagglutination inhibiting and neutralizing antibodies as well as RSV neutralizing antibodies. As summarized in Table 1 below (the Tables appear at the end of the disclosure), the sera of animals immunized with two 10 µg doses of the chimeric protein had titres of PIV-3 specific hemagglutination inhibition (HAI) and PIV-3/RSV neutralizing antibodies at the 6 and 8 week time points which were equivalent to the levels obtained following intranasal inoculation with either live PIV-3 or RSV. In addition, animals immunized with only two 1 ug doses of the chimeric protein elicited strong PIV-3 and RSV specific neutralizing antibodies. These results confirmed the immunogenicity of both the RSV and PIV-3 components of the chimeric protein and provided confirmatory evidence that a single recombinant immunogen can elicit neutralizing antibodies against both RSV and PIV-3.

Example 14

This Example illustrates the immunogenicity and protective ability of the $F_{RSV}$-$HN_{PIV-3}$ protein in cotton rats.

Groups of eight cotton rats were injected intramuscularly with either 1.0 or 10.0 ug of the chimeric $F_{RSV}$-$HN_{PIV-3}$ protein (prepared as described in Example 12) adjuvanted with aluminum phosphate. Groups of control animals were immunized with either placebo (PBS+aluminum phosphate) or live PIV-3 or RSV (administered intranasally). Cotton rats were bled 4 weeks after the primary injection and boosted at 4 weeks with an equivalent dose of the antigen formulation. Serum samples were also taken 1 week after the booster dose. As shown in Table 2 below, data from the 4-week bleed demonstrated that both a 1 and 10 µg dose of the chimeric protein was capable of inducing a strong primary response. Reciprocal mean log$_2$ PIV-3 specific HAI and PIV-3/RSV neutralizing titers were equivalent to the titres obtained with live PIV-3 and RSV. Thus, a single inoculation of the chimeric protein was sufficient to elicit neutralizing antibodies against both PIV-3 and RSV. Strong neutralizing PIV-3 and RSV titres also were observed following the booster dose (5 week bleed). These results provide additional evidence that both the RSV and PIV-3 components of the chimeric protein are highly immunogenic.

To assess the ability of the chimeric immunogen to simultaneously protect animals against both RSV and PIV-3, four cotton rats from each group were challenged intranasally with 100 TCID$_{50}$ units of either PIV-3 or RSV. Animals were killed 4 days after virus challenge. Virus titers were determined in lung lavages. As shown in Table 3 below, animals immunized with either 1 or 10 µg of the chimeric $F_{RSV}$-$HN_{PIV-3}$ protein were completely protected against challenge with either PIV-3 or RSV. These results provide evidence that the chimeric protein is not only highly immunogenic but can also simultaneously protect cotton rats against disease caused by both PIV-3 and RSV infection.

Example 15

This Example illustrates the construction of a Bluescript M13-SK vector containing the chimeric $F_{PIV-3}$-$G_{RSV}$ gene. This chimeric gene construct contains the 5' untranslated region of a mutated PIV-3 F gene but lacks the nucleotide sequence coding for the hydrophobic anchor and cytoplasmic tail domains of both a mutated PIV-3 F and the native RSV G genes. The steps involved in constructing this plasmid are outlined in FIGS. 17 and 18.

The first step (FIG. 17) involved in preparing the PIV-3 F component of the chimeric $F_{PIV-3}$-$G_{RSV}$ gene construct was to eliminate the putative pre-termination sites within the 18 nucleotide long sequence 5' CAAGAAAAAGGAATAAAA 3' (SEQ ID No: 17) located between positions 857 and 874 of the non PCR-amplified PIV-3 F gene and positions 847 and 864 of the PCR-amplified PIV-3 F gene (see FIG. 1). To this end, the PIV-F cDNA of the non-PCR amplified PIV-3 F gene was cut at the BsaAI and EcoRI sites. The BsaAI-EcoRI PIV F gene fragment was cloned into the EcoRI site of a Bluescript M13-SK vector using an EcoRI-BsaAI linker. The 857–874 target region of the PIV-3 F gene (non-PCR amplified) then was mutated by oligonucleotide-mediated mutagenesis using the method of Morinaga et al. [1984, Biotechnology 2: 636–639]. Plasmid pPI3Fc (Example 1) was cut with ScaI in the Amp$^r$ gene and dephosphorylated with alkaline phosphatase (plasmid #1). A second sample of plasmid pPI3Fc was cut with BstEII and NsiI to produce a 3.9 Kb restricted plasmid, lacking the 0.9 Kb BstEII-NsiI fragment of the PIV-3 F gene (plasmid #2). A mutagenic 78-mer synthetic oligonucleotide (#2721 shown in FIG. 17-SEQ ID No: 18)) containing the sequence 5' CAGGAGAAGGGTATCAAG 3' (SEQ ID No: 19) was synthesized to specifically mutate the 857–874 DNA segment without changing the F protein sequence. This oligonucleotide was added to plasmid DNAs #1 and #2, denatured at 100° C. for 3 min. and renatured by gradual cooling. The mixture then was incubated in the presence of DNA polymerase, dNTPs and T4 ligase and transformed into HB101 cells. Bacteria containing the 1.8 Kb mutated PIV-3 F gene were isolated on YT agar plates containing 100 μg/ml ampicillin. Hybridization with the oligonucleotide probe 5' AGGAGAAGGGTATCAAG 3' (SEQ ID No: 20) was used to confirm the presence of the mutated PIV-3 F gene. The mutated gene sequence was confirmed by DNA sequencing. The plasmid containing the mutated PIV-3 gene was designated pPI3Fm.

The second step (FIG. 18) in the engineering of the chimeric gene construct involved constructing a Bluescript based vector to contain the truncated PIV-3 Fm gene lacking the nucleotide sequence coding for the transmembrane anchor domain and cytoplasmic tail of the PIV-3 F protein linked in tandem with the RSV G gene lacking both the 5' leader sequence and the nucleotide sequence coding for the transmembrane anchor domain and cytoplasmic tail of the G glycoprotein.

To prepare this chimeric gene, the orientation of the mutated PIV-F gene in plasmid pPI3Fm first was reversed by EcoRI digestion and religation to generate plasmid pPI3Fmr. To prepare the PIV-3 F gene component of the chimeric gene, plasmid pPI3Fmr was cut with NotI and BsrI to release the 1.7 Kb truncated PIV-3 F gene. To prepare the RSV G component, the 0.95 Kb RSV-G gene lacking both the 5' leader sequence and the DNA segment encoding the G protein anchor domain and cytoplasmic tail was released from plasmid pRSVG (Example 1) by cutting the polylinker with EcoRI and the gene with BamHI. The 0.95 Kb EcoRI-BamHI RSV G gene fragment was subcloned into the EcoRI-BamHI sites of a restricted Bluescript vector, pMl3-SK, to produce plasmid pRSVGt. The 0.95 Kb EcoRI-BamHI G gene fragment and the 1.5 Kb NotI-BsrI truncated PIV-3 F gene were linked via a BsrI-BamHI oligonucleotide cassette (SEQ ID No: 9) restoring the F and G gene coding sequences and cloned into the pRSVGt vector restricted with BamHI and NotI in a 3-way ligation. The plasmid thus generated was designated pFG.

Example 16

This Example outlines the construction of the pD2 baculovirus transfer vector (described in Example 8) containing the chimeric $F_{PIV-3}$-$G_{RSV}$ gene consisting of a mutated PIV-3 F gene lacking the hydrophobic anchor and cytoplasmic coding regions linked to the RSV G gene lacking both the 5' leader sequence and the nucleotide sequences encoding the transmembrane anchor domain and cytoplasmic tail of the G protein.

To prepare this construct, plasmid pFG (Example 15) was cut with EcoRI to release the 2.6 Kb $F_{PIV-3}$-$G_{RSV}$ chimeric gene. The 2.6 Kb EcoRI restricted chimeric gene fragment then was sub-cloned into the EcoRI site of the dephosphorylated pD2 vector to generate the 12.1 Kb plasmid pD2F-G (ATCC 75389).

Example 17

This Example outlines the preparation of plaque-purified recombinant baculoviruses containing the chimeric $F_{PIV-3}$-$G_{RSV}$ gene.

Spodoptera frugiperda (Sf9) cells were co-transfected with 2 ug of pD2F-G plasmid DNA (Example 16) and 1 ug of linear wild-type AcNPV DNA (obtained from Invitrogen). Recombinant baculoviruses containing the $F_{PIV-3}$-$G_{RSV}$ gene were plaque-purified twice according to the procedure outlined in Example 10.

Example 18

This Example illustrates the presence of the chimeric $F_{PIV-3}$-$G_{RSV}$ protein in the supernatant of Sf9 and High 5 cells infected with the recombinant baculoviruses.

Sf9 and High 5 cells were infected with recombinant baculoviruses containing the $F_{PIV-3}$-$G_{RSV}$ gene (Example 16) at a m.o.i. of 5 to 10 pfu/cell. The supernatant of cells infected with the recombinant viruses tested positive for expressed protein in the PIV-3 F specific ELISA. Supernatants of infected cells reacted with both anti-F PIV-3 and anti-G RSV monoclonal antibodies in immunoblots. These results confirm the presence of the chimeric $F_{PIV-3}$-$G_{RSV}$ protein in the supernatants of infected Sf9 and High 5 cells.

Example 19

This Example outlines the preparation of recombinant vaccinia viruses expressing the $F_{PIV-3}$-$F_{RSV}$ and $F_{RSV}$-$HN_{PIV-3}$ genes.

Vaccinia virus recombinant viruses expressing the $F_{PIV-3}$-$F_{RSV}$ (designated vP1192) and $F_{RSV}$-$HN_{PIV-3}$ (designated vP1195) genes were produced at Virogenetics Corporation (Troy, N.Y.) (an entity related to assignee hereof) using the COPAK host-range selection system. Insertion plasmids used in the COPAK host-range selection system contained the vaccinia K1L host-range gene [Perkus et al., (1990) Virology 179:276–286] and the modified vaccinia H6 promoter [Perkus et al. (1989), J. Virology 63:3829–3836]. In these insertion plasmids, the K1L gene, H6 promoter and polylinker region are situated between Copenhagen strain vaccinia flanking arms replacing the ATI region [open reading frames (ORFs) A25L, A26L; Goebel et al., (1990), Virology 179: 247–266; 517–563]. COPAK insertion plasmids are designed for use in in vivo recombination using the rescue virus NYVAC (vP866) (Tartaglia et al., (1992) Virology 188: 217–232). Selection of recombinant viruses was done on rabbit kidney cells.

Recombinant viruses, vP1192 and vP1195 were generated using insertion plasmids pES229A-6 and PSD.RN, respectively. To prepare plasmid pES229A-6 containing the $F_{PIV-3}$-$F_{RSV}$ gene, the COPAK-H6 insertion plasmid pSD555 was cut with SmaI and dephosphorylated with intestinal alkaline phosphatase. The 2.6 Kb $F_{PIV-3}$-$F_{RSV}$ gene was retrieved from plasmid pES60A (Example 4) by cutting the plasmid with EcoRI and BamHI. The 2.6 Kb EcoRI-BamHI $F_{PIV-3}$-$F_{RSV}$ gene was blunt ended with Klenow polymerase, isolated from a low melting point agarose gel and cloned into the SmaI site of the COPAK-H6 insertion plasmid pSD555 to generate plasmid pES229A-6. This positioned the $F_{PIV-3}$-$F_{RSV}$ ORF such that the 5' end is nearest the H6 promoter.

To prepare plasmid PSD.RN, the pSD555 vector first was cut with SmaI and BamHI. Plasmid pM RF-HN (Example 9) containing the truncated $F_{RSV}$-$HN_{PIV-3}$ gene was cut with ClaI, blunt ended with Klenow polymerase and then cut with BamHI. The 3.3 Kb $F_{RSV}$-$HN_{PIV-3}$ gene was cloned into the SmaI-BamHI sites of the pSD555 vector to generate plasmid PSD.RN. This positioned the $F_{RSV}$-$HN_{PIV-3}$ ORF such that the H6 5' end is nearest the H6 promoter.

Plasmids pES229A-6 and PSD.RN were used in in vitro recombination experiments in vero cells with NYVAC (vP866) as the rescuing virus. Recombinant progeny virus was selected on rabbit kidney (RK)-13 cells (ATCC #CCL37). Several plaques were passaged two times on RK-13 cells. Virus containing the chimeric genes were confirmed by standard in situ plaque hybridization [Piccini et al. (1987), Methods in Enzymology, 153:545–563] using radiolabeled probes specific for the PIV and RSV inserted DNA sequences. Plaque purified virus containing the $F_{PIV-3}$-$F_{RSV}$ and $F_{RSV}$-$HN_{PIV-3}$ chimeric genes were designated vP1192 and vP1195, respectively.

Radioimmunoprecipitation was done to confirm the expression of the chimeric genes in vP1192 and vP1195 infected cells. These assays were performed with lysates prepared from infected Vero cells [according to the procedure of Taylor et al., (1990) J. Virology 64, 1441–1450] using guinea pig monospecific PIV-3 anti-HN and anti-F antiserum and rabbit anti-RSV F antiserum. Both the anti-PIV F and anti-RSV F antisera precipitated a protein with an apparent molecular weight of approximately 90 koa from vP1192 infected Vero cells. Both anti-RSV F and guinea pig anti-PIV HN antisera precipitated a protein with an apparent molecular weight of approximately 100 kDa from vP1195 infected cells. These results confirmed the production of the $F_{PIV-3}$-$F_{RSV}$ and $F_{RSV}$-$HN_{PIV-3}$ chimeric proteins in Vero cells infected with the recombinant poxviruses.

SUMMARY OF DISCLOSURE

In summary of the disclosure, the present invention provides multimeric hybrid genes which produce chimeric proteins capable of eliciting protection against infection by a plurality of pathogens, particularly PIV and RSV. Modifications are possible within the scope of this invention.

TABLE 1

Secondary antibody response of guinea pigs immunized with the chimeric $F_{RSV}$-$HN_{PIV-3}$ protein

| Antigen Formulation | Dose (ug) | HAI Titre[a] (log$_2$ ± s.e) PIV-3 | | Neutralization Titre[b] (log$_2$ ± s.e.) PIV-3 | | RSV | |
|---|---|---|---|---|---|---|---|
| | | 6 wk Bleed | 8 wk Bleed | 6 wk Bleed | 8 wk Bleed | 6 wk Bleed | 8 wk Bleed |
| Buffer | — | <1.0 ± 0.0 | <1.0 ± 0.0 | <1.0 ± 0.0 | <1.0 ± 0.0 | <1.0 ± 0.0 | <1.0 ± 0.0 |
| $F_{RSV}$-$HN_{PIV-3}$ | 10.0 | 9.1 ± 0.3 | 9.1 ± 0.3 | 7.1 ± 0.3 | 7.1 ± 0.5 | 5.5 ± 0.9 | 4.5 ± 1.2 |
| | 1.0 | 7.0 ± 2.0 | 7.3 ± 2.2 | 5.0 ± 1.5 | 4.5 ± 1.4 | 4.5 ± 0.5 | 3.0 ± 1.0 |
| Live PIV-3 | | 8.6 ± 0.7 | 7.3 ± 0.6 | 7.0 ± 0.4 | 7.3 ± 0.6 | N/A | N/A |
| Live RSV | | N/A[c] | N/A | N/A | N/A | 5.5 ± 1.5 | 5.0 ± 1.0 |

[a]Reciprocal mean log$_2$ serum dilution which inhibits erythrocyte agglutination by 4 hemagglutinating units of PIV-3
[b]Reciprocal mean log$_2$ serum dilution which blocks hemadsorption of 100 TCID$_{50}$ units of PIV-3 or RSV
[c]N/A — not applicable

TABLE 2

Serum antibody response of cotton rats immunized with the chimeric $F_{RSV}$-$HN_{PIV-3}$ protein[a]

| Antigen Formulation | Dose (ug) | HAI Titre[b] (log$_2$ ± s.d.) PIV-3 | | Neutralization Titre[c] (log$_2$ ± s.d.) PIV-3 | | RSV | |
|---|---|---|---|---|---|---|---|
| | | 4 wk Bleed | 5 wk Bleed | 4 wk Bleed | 5 wk Bleed | 4 wk Bleed | 5 wk Bleed |
| Buffer | — | 2.8 ± 0.5 | <3.0 ± 0.0 | <1.0 ± 0.0 | <1.0 ± 0.0 | 1.8 ± 0.3 | 0.8 ± 0.7 |
| $F_{RSV}$-$HN_{PIV-3}$ | 10.0 | 9.5 ± 1.3 | 10.5 ± 0.6 | >9.0 ± 0.0 | >9.0 ± 0.0 | 5.2 ± 1.1 | 5.8 ± 0.9 |
| | 1.0 | 9.3 ± 1.0 | 10.3 ± 0.5 | >9.0 ± 0.0 | >9.0 ± 0.0 | 5.0 ± 0.7 | 5.8 ± 1.2 |
| Live PIV-3 | | 7.0 ± 0.0 | 8.5 ± 0.7 | >9.0 ± 0.0 | 9.2 ± 0.7 | N/A | N/A |
| Live RSV | | N/A[d] | N/A | N/A | N/A | 5.5 ± 0.6 | 8.5 ± 0.6 |

[a]Each value represents the mean titre of antisera from 8 animlas.
[b]Reciprocal mean log$_2$ serum dilution which inhibits erythrocyte agglutination by 4 hemagglutinating units of PIV-3
[c]Reciprocal mean log$_2$ serum dilution which blocks hemadsorption of 100 ICID$_{50}$ units of PIV-3 or RSV
[d]N/A — not applicable

TABLE 3

Response of immunized cotton rats to PIV/RSV challenge[a]

| Antigen Formulation | Dose (ug) | Mean virus lung titre $\log_{10}$/g lung ± s.d. | |
|---|---|---|---|
| | | RSV | PIV-3 |
| Buffer | — | 3.7 ± 0.3 | 3.4 ± 0.3 |
| $F_{RSV}$-$HN_{PIV-3}$ | 10.0 | ≦1.5 ± 0.0 | ≦1.5 ± 0.0 |
| $F_{RSV}$-$HN_{PIV-3}$ | 1.0 | ≦1.5 ± 0.0 | ≦1.5 ± 0.0 |
| Live RSV | | ≦1.5 ± 0.0 | N.D. |
| Live PIV-3 | | N.D. | ≦1.5 ± 0.0 |

[a]Animals were challenged intranasally with 100 $TCID_{50}$ units of PIV-3 or RSV and killed 4 days later. Each value represents the mean virus lung titre of 4 animals.

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
       (A) LENGTH: 1844 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
AAGTCAATAC CAACAACTAT TAGCAGTCAT ACGTGCAAGA ACAAGAAAGA AGAGATTCAA      60

AAAGCTAAAT AAGAGAAATC AAAACAAAAG GTATAGAACA CCCGAACAAC AAAATCAAAA     120

CATCCAATCC ATTTTAAACA AAAATTCCAA AAGAGACCGG CAACACAACA AGCACCAAAC     180

ACAATGCCAA CTTTAATACT GCTAATTATT ACAACAATGA TTATGGCATC TTCCTGCCAA     240

ATAGATATCA CAAAACTACA GCATGTAGGT GTATTGGTCA ACAGTCCCAA AGGGATGAAG     300

ATATCACAAA ACTTCGAAAC AAGATATCTA ATTTTGAGCC TCATACCAAA AATAGAAGAC     360

TCTAACTCTT GTGGTGACCA ACAGATCAAA CAATACAAGA GGTTATTGGA TAGACTGATC     420

ATCCCTCTAT ATGATGGATT AAGATTACAG AAAGATGTGA TAGTAACCAA TCAAGAATCC     480

AATGAAAACA CTGATCCCAG AACAAGACGA TCCTTTGGAG GGGTAATTGG AACCATTGCT     540

CTGGGAGTAG CAACCTCAGC ACAAATTACA GCGGCAGTTG CTCTGGTTGA AGCCAAGCAG     600

GCAAAATCAG ACATCGAAAA ACTCAAAGAA GCAATCAGGG ACACAAACAA AGCAGTGCAG     660

TCAGTTCAGA GCTCTATAGG AAATTTAATA GTAGCAATTA AATCAGTCCA AGATTATGTC     720

AACAACGAAA TGGTGCCATC GATTGCTAGA CTAGGTTGTG AAGCAGCAGG ACTTCAATTA     780

GGAATTGCAT TAACACAGCA TTACTCAGAA TTAACAAACA TATTTGGTGA TAACATAGGA     840

TCGTTACAAG AAAAAGGAAT AAAATTCAA GGTATAGCAT CATTATACCG CACAAATATC     900

ACAGAAATAT TCACAACATC AACAGTTGAT AAATATGATA TCTATGATCT ATTATTTACA     960

GAATCAATAA AGGTGAGAGT TATAGATGTT GATTTGAATG ATTACTCAAT CACCCTCCAA    1020

GTCAGACTCC CTTTATTAAC TAGGCTGCTG AACACTCAGA TCTACAAAGT AGATTCCATA    1080

TCATATAATA TCCAAAACAG AGAATGGTAT ATCCCTCTTC CCAGCCATAT CATGACGAAA    1140
```

```
GGGGCATTTC TAGGTGGAGC AGATGTCAAG GAATGTATAG AAGCATTCAG CAGTTATATA    1200

TGCCCTTCTG ATCCAGGATT TGTACTAAAC CATGAAATGG AGAGCTGCTT ATCAGGAAAC    1260

ATATCCCAAT GTCCAAGAAC CACGGTCACA TCAGACATTG TTCCAAGATA TGCATTTGTC    1320

AATGGAGGAG TGGTTGCAAA CTGTATAACA ACCACCTGTA CATGCAACGG AATCGACAAT    1380

AGAATCAATC AACCACCTGA TCAAGGAGTA AAAATTATAA CACATAAAGA ATGTAATACA    1440

ATAGGTATCA ACGGAATGCT GTTCAATACA AATAAAGAAG GAACTCTTGC ATTCTACACA    1500

CCAAATGATA TAACACTAAA TAATTCTGTT GCACTTGATC CAATTGACAT ATCAATCGAG    1560

CTTAACAAAG CCAAATCAGA TCTAGAAGAA TCAAAAGAAT GGATAAGAAG GTCAAATCAA    1620

AAACTAGATT CTATTGGAAA CTGGCATCAA TCTAGCACTA CAATCATAAT TATTTTAATA    1680

ATGATCATTA TATTGTTTAT AATTAATGTA ACGATAATTA CAATTGCAAT TAAGTATTAC    1740

AGAATTCAAA AGAGAAATCG AGTGGATCAA AATGACAAGC CATATGTACT AACAAACAAA    1800

TGACATATCT ATAGATCATT AGATATTAAA ATTATAAAAA ACTT                      1844

(2) INFORMATION FOR SEQ ID NO:2:

(i) SEQUENCE CHARACTERISTICS:
        (A) LENGTH: 539 amino acids
        (B) TYPE: amino acid
        (C) STRANDEDNESS: single
        (D) TOPOLOGY: linear (xi) SEQUENCE DESCRIPTION: SEQ ID NO:2:

Met Pro Thr Leu Ile Leu Leu Ile Ile Thr Thr Met Ile Met Ala Ser
1               5                  10                  15

Ser Cys Gln Ile Asp Ile Thr Lys Leu Gln His Val Gly Val Leu Val
                20                  25                  30

Asn Ser Pro Lys Gly Met Lys Ile Ser Gln Asn Phe Glu Thr Arg Tyr
            35                  40                  45

Leu Ile Leu Ser Leu Ile Pro Lys Ile Glu Asp Ser Asn Ser Cys Gly
        50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Thr Asn
                85                  90                  95

Gln Glu Ser Asn Glu Asn Thr Asp Pro Arg Thr Arg Ser Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Lys Ser Asp Ile
130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Asn Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240
```

```
Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
                260                 265                 270

Asp Tyr Ser Ile Thr Leu Gln Val Arg Leu Pro Leu Leu Thr Arg Leu
                275                 280                 285

Leu Asn Thr Gln Ile Tyr Lys Val Asp Ser Ile Ser Tyr Asn Ile Gln
                290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
                340                 345                 350

Glu Ser Cys Leu Ser Gly Asn Ile Ser Gln Cys Pro Arg Thr Thr Val
                355                 360                 365

Thr Ser Asp Ile Val Pro Arg Tyr Ala Phe Val Asn Gly Gly Val Val
370                 375                 380

Ala Asn Cys Ile Thr Thr Thr Cys Thr Cys Asn Gly Ile Asp Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
                420                 425                 430

Gly Thr Leu Ala Phe Tyr Thr Pro Asn Asp Ile Thr Leu Asn Asn Ser
                435                 440                 445

Val Ala Leu Asp Pro Ile Asp Ile Ser Ile Glu Leu Asn Lys Ala Lys
                450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Ile Leu Ile Met Ile Ile Ile Leu Phe Ile Ile Asn Val Thr Ile Ile
                500                 505                 510

Thr Ile Ala Ile Lys Tyr Tyr Arg Ile Gln Lys Arg Asn Arg Val Asp
                515                 520                 525

Gln Asn Asp Lys Pro Tyr Val Leu Thr Asn Lys
530                 535

(2) INFORMATION FOR SEQ ID NO:3:

(i) SEQUENCE CHARACTERISTICS:
        (A) LENGTH: 1833 base pairs
        (B) TYPE: nucleic acid
        (C) STRANDEDNESS: single
        (D) TOPOLOGY: linear (xi) SEQUENCE DESCRIPTION: SEQ ID NO:3:

AGACAAATCC AAATTCGAGA TGGAATACTG GAAGCATACC AATCACGGAA AGGATGCTGG     60

CAATGAGCTG GAGACGTCCA TGGCTACTAA TGGCAACAAG CTCACCAATA AGATAACATA    120

TATATTATGG ACAATAATCC TGGTGTTATT ATCAATAGTC TTCATCATAG TGCTAATTAA    180

TTCCATCAAA AGTGAAAAGG CTCATGAATC ATTGCTGCAA GACATAAATA ATGAGTTTAT    240

GGAAATTACA GAAAAGATCC AAATGGCATC GGATAATACC AATGATCTAA TACAGTCAGG    300

AGTGAATACA AGGCTTCTTA CAATTCAGAG TCATGTCCAG AATTATATAC CAATATCACT    360
```

```
GACACAACAG ATGTCAGATC TTAGGAAATT CATTAGTGAA ATTACAATTA GAAATGATAA      420

TCAAGAAGTG CTGCCACAAA GAATAACACA TGATGTGGGT ATAAAACCTT TAAATCCAGA      480

TGATTTTTGG AGATGCACGT CTGGTCTTCC ATCTTTAATG AAAACTCCAA AATAAGGTT      540

AATGCCAGGG CCGGGATTAT TAGCTATGCC AACGACTGTT GATGGCTGTA TCAGAACTCC      600

GTCCTTAGTT ATAAATGATC TGATTTATGC TTATACCTCA AATCTAATTA CTCGAGGTTG      660

TCAGGATATA GGAAAATCAT ATCAAGTCTT ACAGATAGGG ATAATAACTG TAAACTCAGA      720

CTTGGTACCT GACTTAAATC CCAGGATCTC TCATACTTTT AACATAAATG ACAATAGGAA      780

GTCATGTTCT CTAGCACTCC TAAATACAGA TGTATATCAA CTGTGTTCAA CTCCCAAAGT      840

TGATGAAAGA TCAGATTATG CATCATCAGG CATAGAAGAT ATTGTACTTG ATATTGTCAA      900

TTATGATGGC TCAATCTCAA CAACAAGATT TAAGAATAAT AACATAAGCT TGATCAACC      960

TTATGCTGCA CTATACCCAT CTGTTGGACC AGGGATATAC TACAAAGGCA AATAATATT     1020

TCTCGGGTAT GGAGGTCTTG AACATCCAAT AAATGAGAAT GTAATCTGCA ACACAACTGG     1080

GTGTCCCGGG AAAACACAGA GAGACTGCAA TCAGGCATCT CATAGTCCAT GGTTTTCAGA     1140

TAGGAGGATG GTCAACTCTA TCATTGTTGT TGACAAAGGC TTAAACTCAA TTCCAAAATT     1200

GAAGGTATGG ACGATATCTA TGAGACAGAA TTACTGGGGG TCAGAAGGAA GGTTACTTCT     1260

ACTAGGTAAC AAGATCTATA TATATACAAG ATCCACAAGT TGGCATAGCA AGTTACAATT     1320

AGGAATAATT GATATTACTG ATTACAGTGA TATAAGGATA AAATGGACAT GGCATAATGT     1380

GCTATCAAGA CCAGGAAACA ATGAATGTCC ATGGGGACAT TCATGTCCAG ATGGATGTAT     1440

AACAGGAGTA TATACTGATG CATATCCACT CAATCCCACA GGGAGCATTG TGTCATCTGT     1500

CATATTAGAT TCACAAAAAT CGAGAGTGAA CCCAGTCATA ACTTACTCAA CAGCAACCGA     1560

AAGAGTAAAC GAGCTGGCCA TCCGAAACAG AACACTCTCA GCTGGATATA CAACAACAAG     1620

CTGCATCACA CACTATAACA AAGGATATTG TTTTCATATA GTAGAAATAA ATCAGAAAAG     1680

CTTAAACACA CTTCAACCCA TGTTGTTCAA GACAGAGGTT CCAAAAAGCT GCAGTTAATC     1740

ATAATTAACC GCAATATGCA TTAACCTATC TATAATACAA GTATATGATA AGTAATCAGC     1800

AATCAGACAA TAGACAAAAG GGAAATATAA AAA                                   1833
```

(2) INFORMATION FOR SEQ ID NO:4:

(i) SEQUENCE CHARACTERISTICS:
        (A) LENGTH: 572 amino acids
        (B) TYPE: amino acid
        (C) STRANDEDNESS: single
        (D) TOPOLOGY: linear (xi) SEQUENCE DESCRIPTION: SEQ ID NO:4:

```
Met Glu Tyr Trp Lys His Thr Asn His Gly Lys Asp Ala Gly Asn Glu
 1               5                  10                  15

Leu Glu Thr Ser Met Ala Thr Asn Gly Asn Lys Leu Thr Asn Lys Ile
                20                  25                  30

Thr Tyr Ile Leu Trp Thr Ile Ile Leu Val Leu Leu Ser Ile Val Phe
            35                  40                  45

Ile Ile Val Leu Ile Asn Ser Ile Lys Ser Glu Lys Ala His Glu Ser
        50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95
```

```
Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
            115                 120                 125

Thr Ile Arg Asn Asp Asn Gln Glu Val Leu Pro Gln Arg Ile Thr His
            130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
            165                 170                 175

Gly Pro Gly Leu Leu Ala Met Pro Thr Thr Val Asp Gly Cys Ile Arg
            180                 185                 190

Thr Pro Ser Leu Val Ile Asn Asp Leu Ile Tyr Ala Tyr Thr Ser Asn
            195                 200                 205

Leu Ile Thr Arg Gly Cys Gln Asp Ile Gly Lys Ser Tyr Gln Val Leu
            210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
            245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
            275                 280                 285

Val Leu Asp Ile Val Asn Tyr Asp Gly Ser Ile Ser Thr Thr Arg Phe
            290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
            325                 330                 335

Tyr Gly Gly Leu Glu His Pro Ile Asn Glu Asn Val Ile Cys Asn Thr
            340                 345                 350

Thr Gly Cys Pro Gly Lys Thr Gln Arg Asp Cys Asn Gln Ala Ser His
            355                 360                 365

Ser Pro Trp Phe Ser Asp Arg Arg Met Val Asn Ser Ile Ile Val Val
            370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
            405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
            435                 440                 445

Trp Thr Trp His Asn Val Leu Ser Arg Pro Gly Asn Asn Glu Cys Pro
            450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
            485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Arg Asn Arg Thr Leu Ser Ala
            515                 520                 525
```

```
Gly Tyr Thr Thr Thr Ser Cys Ile Thr His Tyr Asn Lys Gly Tyr Cys
    530                 535                 540

Phe His Ile Val Glu Ile Asn Gln Lys Ser Leu Asn Thr Leu Gln Pro
545                 550                 555                 560

Met Leu Phe Lys Thr Glu Val Pro Lys Ser Cys Ser
                565                 570
```

(2) INFORMATION FOR SEQ ID NO:5:

(i) SEQUENCE CHARACTERISTICS:
        (A) LENGTH: 1886 base pairs
        (B) TYPE: nucleic acid
        (C) STRANDEDNESS: single
        (D) TOPOLOGY: linear (xi) SEQUENCE DESCRIPTION: SEQ ID NO:5:

```
ATGGAGTTGC CAATCCTCAA AGCAAATGCA ATTACCACAA TCCTCGCTGC AGTCACATTT      60

TGCTTTGCTT CTAGTCAAAA CATCACTGAA GAATTTTATC AATCAACATG CAGTGCAGTT     120

AGCAAAGGCT ATCTTAGTGC TCTAAGAACT GGTTGGTATA CTAGTGTTAT AACTATAGAA     180

TTAAGTAATA TCAAGGAAAA TAAGTGTAAT GGAACAGATG CTAAGGTAAA ATTGATGAAA     240

CAAGAATTAG ATAAATATAA AAATGCTGTA ACAGAATTGC AGTTGCTCAT GCAAAGCACA     300

CCAGCAGCAA ACAATCGAGC CAGAAGAGAA CTACCAAGGT TTATGAATTA TACACTCAAC     360

AATACCAAAA AAACCAATGT AACATTAAGC AAGAAAAGGA AAAGAAGATT TCTTGGTTTT     420

TTGTTAGGTG TTGGATCTGC AATCGCCAGT GGCATTGCTG TATCTAAGGT CCTGCACTTA     480

GAAGGAGAAG TGAACAAGAT CAAAAGTGCT CTACTATCCA CAAACAAGGC CGTAGTCAGC     540

TTATCAAATG GAGTTAGTGT CTTAACCAGC AAAGTGTTAG ACCTCAAAAA CTATATAGAT     600

AAACAATTGT TACCTATTGT GAATAAGCGA AGCTGCAGAA TATCAAATAT AGAAACTGTG     660

ATAGAGTTCC AACAAAAGAA CAACAGACTA CTAGAGATTA CCAGGGAATT TAGTGTTAAT     720

GCAGGTGTAA CTACACCTGT AAGCACTTAC ATGTTAACTA ATAGTGAATT ATTGTCATTA     780

ATCAATGATA TGCCTATAAC AAATGATCAG AAAAAGTTAA TGTCCAACAA TGTTCAAATA     840

GTTAGACAGC AAAGTTACTC TATCATGTCC ATAATAAAAG AGGAAGTCTT AGCATATGTA     900

GTACAATTAC CACTATATGG TGTGATAGAT ACACCTTGTT GGAAATTACA CACATCCCCT     960

CTATGTACAA CCAACACAAA AGAAGGGTCA AACATCTGTT TAACAAGAAC TGACAGAGGA    1020

TGGTACTGTG ACAATGCAGG ATCAGTATCT TTCTTCCCAC AAGCTGAAAC ATGTAAAGTT    1080

CAATCGAATC GAGTATTTTG TGACACAATG AACAGTTTAA CATTACCAAG TGAAGTAAAT    1140

CTCTGCAATG TTGACATATT CAATCCCAAA TATGATTGTA AAATTATGAC TTCAAAAACA    1200

GATGTAAGCA GCTCCGTTAT CACATCTCTA GGAGCCATTG TGTCATGCTA TGGCAAAACT    1260

AAATGTACAG CATCCAATAA AAATCGTGGA ATCATAAAGA CATTTTCTAA CGGGTGTGAT    1320

TATGTATCAA ATAAAGGGGT GGACACTGTG TCTGTAGGTA ACACATTATA TTATGTAAAT    1380

AAGCAAGAAG GCAAAAGTCT CTATGTAAAA GGTGAACCAA TAATAAATTT CTATGACCCA    1440

TTAGTATTCC CCTCTGATGA ATTTGATGCA TCAATATCTC AAGTCAATGA AAGATTAAC    1500

CAGAGTTTAG CATTTATTCG TAAATCCGAT GAATTATTAC ATAATGTAAA TGCTGGTAAA    1560

TCAACCACAA ATATCATGAT AACTACTATA ATTATAGTGA TTATAGTAAT ATTGTTATCA    1620

TTAATTGCTG TTGGACTGCT CCTATACTGT AAGGCCAGAA GCACACCAGT CACACTAAGC    1680

AAGGATCAAC TGAGTGGTAT AAATAATATT GCATTTAGTA ACTGAATAAA AATAGCACCT    1740

AATCATGTTC TTACAATGGT TTACTATCTG CTCATAGACA ACCCATCTAT CATTGGATTT    1800
```

```
TCTTAAAATC TGAACTTCAT CGAAACTCTT ATCTATAAAC CATCTCACTT ACACTATTTA    1860

AGTAGATTCC TAGTTTATAG TTATAT                                        1886
```

(2) INFORMATION FOR SEQ ID NO:6:

(i) SEQUENCE CHARACTERISTICS:
        (A) LENGTH: 594 amino acids
        (B) TYPE: amino acid
        (C) STRANDEDNESS: single
        (D) TOPOLOGY: linear (xi) SEQUENCE DESCRIPTION: SEQ ID NO:6:

```
Met Glu Leu Pro Ile Leu Lys Ala Asn Ala Ile Thr Thr Ile Leu Ala
1               5                  10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Arg Ser Cys Arg Ile Ser Asn Ile Glu Thr Val Ile Glu Phe Gln
    210                 215                 220

His Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
```

|   | 340 |   |   | 345 |   |   | 350 |   |   |
|---|---|---|---|---|---|---|---|---|---|

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Leu Val Phe Pro Ser Asp Glu Phe Asp Ala Ser Ile
                500                 505                 510

Ser Gln Val Asn Glu Lys Ile Asn Gln Ser Leu Ala Phe Ile Arg Lys
                515                 520                 525

Ser Asp Glu Leu Leu His Asn Val Asn Ala Gly Lys Ser Thr Thr Asn
                530                 535                 540

Ile Met Ile Thr Thr Ile Ile Ile Glu Ile Val Ile Leu Leu Ser
545                 550                 555                 560

Leu Ile Ala Val Gly Leu Leu Leu Tyr Cys Lys Ala Arg Ser Thr Pro
                565                 570                 575

Val Thr Leu Ser Lys Asp Gln Leu Ser Gly Ile Asn Asn Ile Ala Phe
                580                 585                 590

Ser Asn (2) INFORMATION FOR SEQ ID NO:7:

(i) SEQUENCE CHARACTERISTICS:
        (A) LENGTH: 920 base pairs
        (B) TYPE: nucleic acid
        (C) STRANDEDNESS: single
        (D) TOPOLOGY: linear (xi) SEQUENCE DESCRIPTION: SEQ ID NO:7:

| | | | | | |
|---|---|---|---|---|---|
| TGCAAACATG | TCCAAAAACA | AGGACCAACG | CACCGCTAAG | ACACTAGAAA | AGACCTGGGA | 60 |
| CACTCTCAAT | CATTTATTAT | TCATATCATC | GGGCTTATAT | AAGTTAAATC | TTAAATCTGT | 120 |
| AGCACAAATC | ACATTATCCA | TTCTGGCAAT | GATAATCTCA | ACTTCACTTA | TAATTACAGC | 180 |
| CATCATATTC | ATAGCCTCGG | CAAACCACAA | AGTCACACTA | ACAACTGCAA | TCATACAAGA | 240 |
| TGCAACAAGC | CAGATCAAGA | ACACAACCCC | AACATACCTC | ACTCAGGATC | CTCAGCTTGG | 300 |
| AATCAGCTTC | TCCAATCTGT | CTGAAATTAC | ATCACAAACC | ACCACCATAC | TAGCTTCAAC | 360 |
| AACACCAGGA | GTCAAGTCAA | ACCTGCAACC | CACAACAGTC | AAGACTAAAA | ACACAACAAC | 420 |
| AACCCAAACA | CAACCCAGCA | AGCCCACTAC | AAAACAACGC | CAAAACAAAC | CACCAAACAA | 480 |
| ACCCAATAAT | GATTTTCACT | TCGAAGTGTT | TAACTTTGTA | CCCTGCAGCA | TATGCAGCAA | 540 |
| CAATCCAACC | TGCTGGGCTA | TCTGCAAAAG | AATACCAAAC | AAAAAACCAG | GAAAGAAAAC | 600 |

```
CACCACCAAG CCTACAAAAA AACCAACCTT CAAGACAACC AAAAAAGATC TCAAACCTCA      660

AACCACTAAA CCAAAGGAAG TACCCACCAC CAAGCCCACA GAAGAGCCAA CCATCAACAC      720

CACCAAAACA AACATCACAA CTACACTGCT CACCAACAAC ACCACAGGAA ATCCAAAACT      780

CACAAGTCAA ATGGAAACCT TCCACTCAAC CTCCTCCGAA GGCAATCTAA GCCCTTCTCA      840

AGTCTCCACA ACATCCGAGC ACCCATCACA ACCCTCATCT CCACCCAACA CAACACGCCA      900

GTAGTTATTA AAAAAAAAA                                                   920
```

(2) INFORMATION FOR SEQ ID NO:8:

(i) SEQUENCE CHARACTERISTICS:
        (A) LENGTH: 298 amino acids
        (B) TYPE: amino acid
        (C) STRANDEDNESS: single
        (D) TOPOLOGY: linear (xi) SEQUENCE DESCRIPTION: SEQ ID NO:8:

```
Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Thr Ala Ile Ile Phe Ile Ala Ser
50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
            85                  90                  95

Leu Gly Ile Ser Phe Ser Asn Leu Ser Glu Ile Thr Ser Gln Thr Thr
        100                 105                 110

Thr Ile Leu Ala Ser Thr Thr Pro Gly Val Lys Ser Asn Leu Gln Pro
    115                 120                 125

Thr Thr Val Lys Thr Lys Asn Thr Thr Thr Gln Thr Gln Pro Ser
130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
            165                 170                 175

Ser Asn Asn Pro Thr Cys Trp Ala Ile Cys Lys Arg Ile Pro Asn Lys
        180                 185                 190

Lys Pro Gly Lys Lys Thr Thr Thr Lys Pro Thr Lys Lys Pro Thr Phe
    195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
            245                 250                 255

Lys Leu Thr Ser Gln Met Glu Thr Phe His Ser Thr Ser Ser Glu Gly
        260                 265                 270

Asn Leu Ser Pro Ser Gln Val Ser Thr Thr Ser Glu His Pro Ser Gln
    275                 280                 285

Pro Ser Ser Pro Pro Asn Thr Thr Arg Gln
290                 295
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:9:

```
ATCAATCAAA GGTCCTGTGA TAATAG                                          26
```

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:10:

```
CATGACTTGA TAATGAG                                                    17
```

(2) INFORMATION FOR SEQ ID NO:11:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:11:

```
AATTCATGGA GTTGCTAATC CTCAAAGCAA ATGCAATTAC CACAATCCTC ACTGCAGTCA     60

CATTTTGTTT TGCTTCTGGT TCTAAG                                          86
```

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:12:

```
ACTGGCATCA ATCTAGCACT ACATGAG                                         27
```

(2) INFORMATION FOR SEQ ID NO:13:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (xi) SEQUENCE DESCRIPTION: SEQ ID NO:13:

```
AATTCATGCC AACTTTAATA CTGCTAATTA TTACAACAAT GATTATGGCA TCTTCCTGCC     60

AAATAGATAT CACAAAACTA CAGCATGTAG GTGTATTGGT CAACAGTCCC AAAGGGATGA    120

AGATATCACA AAACTT                                                    136
```

(2) INFORMATION FOR SEQ ID NO:14:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO:14:

ATCATGGAGA TAATTAAAAT GATAACCATC TCGCAAATAA ATAAGTATTT TACTGTTTTC      60

GTAACAGTTT TGTAATAAAA AAACCTATAA ATAG      94

(2) INFORMATION FOR SEQ ID NO:15:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (xi) SEQUENCE DESCRIPTION: SEQ ID NO:15:

ATCATGGAGA TAATTAAAAT GATAACCATC TCGCAAATAA ATAAGTATTT TACTGTTTTC      60

GTAACAGTTT TGTAATAAAA AAACCTATAA ATATTCCGGA ATTCAGATCT GCAGCGGCCG     120

CTCCATCTAG AAGGTACCCG G      141

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:16:

CATGACTAAT TCCATCAAAA GTGAAAAGGC T      31

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:17:

CAAGAAAAAG GAATAAAA      18

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:18:

ATTTCTGTGA TATTTGTGCG GTATAATGAT GCTATACCT      39

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:19:

CAGGAGAAGG GTATCAAG      18

(2) INFORMATION FOR SEQ ID NO:20:

(i) SEQUENCE CHARACTERISTICS:
        (A) LENGTH: 17 base pairs (B) TYPE: nucleic acid
(C) STRANDEDNESS: single
(D) TOPOLOGY: linear (xi) SEQUENCE DESCRIPTION: SEQ ID NO:20:

AGGAGAAGGG TATCAAG                                                     17

(2) INFORMATION FOR SEQ ID NO:21:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO:21:

ATCATGGAGA TAATTAAAAT GATAACCATC TCGCAAATAA ATAAGTATTT TACTGTTTTC       60

GTAACAGTTT TGTAATAAAA AAACCTATAA ATAG                                  94

(2) INFORMATION FOR SEQ ID NO:22:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:22:

Gln Glu Lys Gly Ile Lys
1               5

(2) INFORMATION FOR SEQ ID NO:23:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:23:

Gln Glu Lys Gly Ile Lys
1               5

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:24:

ATCAATCTAG CACTACACAG                                                  20

(2) INFORMATION FOR SEQ ID NO:25:

(i) SEQUENCE CHARACTERISTICS:
        (A) LENGTH: 1617 base pairs
        (B) TYPE: nucleic acid
        (C) STRANDEDNESS: single
        (D) TOPOLOGY: linear (xi) SEQUENCE DESCRIPTION: SEQ ID NO:25:

ATGCCAACTT TAATACTGCT AATTATTACA ACAATGATTA TGGCATCTTC CTGCCAAATA       60

GATATCACAA AACTACAGCA TGTAGGTGTA TTGGTCAACA GTCCCAAAGG GATGAAGATA      120

TCACAAAACT TCGAAACAAG ATATCTAATT TTGAGCCTCA TACCAAAAAT AGAAGACTCT      180

AACTCTTGTG GTGACCAACA GATCAAACAA TACAAGAGGT TATTGGATAG ACTGATCATC      240

-continued

```
CCTCTATATG ATGGATTAAG ATTACAGAAA GATGTGATAG TAACCAATCA AGAATCCAAT      300

GAAAACACTG ATCCCAGAAC AAGACGATCC TTTGGAGGGG TAATTGGAAC CATTGCTCTG      360

GGAGTAGCAA CCTCAGCACA AATTACAGCG GCAGTTGCTC TGGTTGAAGC CAAGCAGGCA      420

AAATCAGACA TCGAAAAACT CAAAGAAGCA ATCAGGGACA CAAACAAAGC AGTGCAGTCA      480

GTTCAGAGCT CTATAGGAAA TTTAATAGTA GCAATTAAAT CAGTCCAAGA TTATGTCAAC      540

AACGAAATGG TGCCATCGAT TGCTAGACTA GGTTGTGAAG CAGCAGGACT TCAATTAGGA      600

ATTGCATTAA CACAGCATTA CTCAGAATTA ACAAACATAT TGGTGATAA CATAGGATCG       660

TTACAAGAAA AAGGAATAAA ATTACAAGGT ATAGCATCAT TATACCGCAC AAATATCACA      720

GAAATATTCA ACATCAAC AGTTGATAAA TATGATATCT ATGATCTATT ATTTACAGAA        780

TCAATAAAGG TGAGAGTTAT AGATGTTGAT TTGAATGATT ACTCAATCAC CCTCCAAGTC      840

AGACTCCCTT TATTAACTAG GCTGCTGAAC ACTCAGATCT ACAAAGTAGA TTCCATATCA      900

TATAATATCC AAAACAGAGA ATGGTATATC CCTCTTCCCA GCCATATCAT GACGAAAGGG      960

GCATTTCTAG TGGAGCAGA TGTCAAGGAA TGTATAGAAG CATTCAGCAG TTATATATGC       1020

CCTTCTGATC CAGGATTTGT ACTAAACCAT GAAATGGAGA GCTGCTTATC AGGAAACATA     1080

TCCCAATGTC CAAGAACCAC GGTCACATCA GACATTGTTC CAAGATATGC ATTTGTCAAT      1140

GGAGGAGTGG TTGCAAACTG TATAACAACC ACCTGTACAT GCAACGGAAT CGACAATAGA     1200

ATCAATCAAC CACCTGATCA AGGAGTAAAA ATTATAACAC ATAAAGAATG TAATACAATA     1260

GGTATCAACG GAATGCTGTT CAATACAAAT AAAGAAGGAA CTCTTGCATT CTACACACCA      1320

AATGATATAA CACTAAATAA TTCTGTTGCA CTTGATCCAA TTGACATATC AATCGAGCTT     1380

AACAAAGCCA ATCAGATCT AGAAGAATCA AAAGAATGGA TAAGAAGGTC AAATCAAAAA       1440

CTAGATTCTA TTGGAAACTG GCATCAATCT AGCACTACAA TCATAATTAT TTTAATAATG     1500

ATCATTATAT TGTTTATAAT TAATGTAACG ATAATTACAA TTGCAATTAA GTATTACAGA     1560

ATTCAAAAGA GAAATCGAGT GGATCAAAAT GACAAGCCAT ATGTACTAAC AAACAAA        1617

(2) INFORMATION FOR SEQ ID NO:26:

(i) SEQUENCE CHARACTERISTICS:
        (A) LENGTH: 1715 base pairs
        (B) TYPE: nucleic acid
        (C) STRANDEDNESS: single
        (D) TOPOLOGY: linear (xi) SEQUENCE DESCRIPTION: SEQ ID NO:26:

ATGGAATACT GGAAGCATAC CAATCACGGA AAGGATGCTG GCAATGAGCT GGAGACGTCC       60

ATGGCTACTA ATGGCAACAA GCTCACCAAT AAGATAACAT ATATATTATG GACAATAATC      120

CTGGTGTTAT TATCAATAGT CTTCATCATA GTGCTAATTA ATTCCATCAA AAGTGAAAAG      180

GCTCATGAAT CATTGCTGCA AGACATAAAT AATGAGTTTA TGGAAATTAC AGAAAAGATC      240

CAAATGGCAT CGGATAATAC CAATGATCTA ATACAGTCAG GAGTGAATAC AAGGCTTCTT      300

ACAATTCAGA GTCATGTCCA GAATTATATA CCAATATCAC TGACACAACA GATGTCAGAT      360

CTTAGGAAAT TCATTAGTGA AATTACAATT AGAAATGATA ATCAAGAAGT GCTGCCACAA      420

AGAATAACAC ATGATGTGGG TATAAAACCT TTAAATCCAG ATGATTTTTG GAGATGCACG      480

TCTGGTCTTC CATCTTTAAT GAAAACTCCA AAAATAAGGT TAATGCCAGG GCCGGGATTA      540

TTAGCTATGC CAACGACTGT TGATGGCTGT ATCAGAACTC CGTCCTTAGT TATAAATGAT      600

CTGATTTATG CTTATACCTC AAATCTAATT ACTCGAGGTT GTCAGGATAT AGGAAAATCA      660
```

-continued

| | |
|---|---|
| TATCAAGTCT TACAGATAGG GATAATAACT GTAAACTCAG ACTTGGTACC TGACTTAAAT | 720 |
| CCCAGGATCT CTCATACTTT TAACATAAAT GACAATAGGA AGTCATGTTC TCTAGCACTC | 780 |
| CTAAATACAG ATGTATATCA ACTGTGTTCA ACTCCCAAAG TTGATGAAAG ATCAGATTAT | 840 |
| GCATCATCAG GCATAGAAGA TATTGTACTT GATATTGTCA ATTATGATGG CTCAATCTCA | 900 |
| ACAACAAGAT TTAAGAATAA TAACATAAGC TTTGATCAAC CTTATGCTGC ACTATACCCA | 960 |
| TCTGTTGGAC CAGGGATATA CTACAAAGGC AAAATAATAT TTCTCGGGTA TGGAGGTCTT | 1020 |
| GAACATCCAA TAAATGAGAA TGTAATCTGC AACACAACTG GGTGTCCCGG GAAAACACAG | 1080 |
| AGAGACTGCA ATCAGGCATC TCATAGTCCA TGGTTTTCAG ATAGGAGGAT GGTCAACTCT | 1140 |
| ATCATTGTTG TTGACAAAGG CTTAAACTCA ATTCCAAAAT TGAAGGTATG GACGATATCT | 1200 |
| ATGAGACAGA ATTACTGGGG GTCAGAAGGA AGGTTACTTC TACTAGGTAA CAAGATCTAT | 1260 |
| ATATATACAA GATCCACAAG TTGGCATAGC AAGTTACAAT TAGGAATAAT TGATATTACT | 1320 |
| GATTACAGTG ATATAAGGAT AAAATGGACA TGGCATAATG TGCTATCAAG ACCAGGAAAC | 1380 |
| AATGAATGTC CATGGGGACA TTCATGTCCA GATGGATGTA TAACAGGAGT ATATACTGAT | 1440 |
| GCATATCCAC TCAATCCCAC AGGGAGCATT GTGTCATCTG TCATATTAGA TTCACAAAAA | 1500 |
| TCGAGAGTGA ACCCAGTCAT AACTTACTCA ACAGCAACCG AAAGAGTAAA CGAGCTGGCC | 1560 |
| ATCCGAAACA GAACACTCTC AGCTGGATAT ACAACAACAA GCTGCATCAC ACACTATAAC | 1620 |
| AAAGGATATT GTTTTCATAT AGTAGAAATA AATCAGAAAA GCTTAAACAC ACTTCAACCC | 1680 |
| ATGTTGTTCA AGACAGAGGT TCCAAAAAGC TGCAG | 1715 |

(2) INFORMATION FOR SEQ ID NO:27:

(i) SEQUENCE CHARACTERISTICS:
        (A) LENGTH: 1722 base pairs
        (B) TYPE: nucleic acid
        (C) STRANDEDNESS: single
        (D) TOPOLOGY: linear (xi) SEQUENCE DESCRIPTION: SEQ ID NO:27:

| | |
|---|---|
| ATGGAGTTGC CAATCCTCAA AGCAAATGCA ATTACCACAA TCCTCGCTGC AGTCACATTT | 60 |
| TGCTTTGCTT CTAGTCAAAA CATCACTGAA GAATTTTATC AATCAACATG CAGTGCAGTT | 120 |
| AGCAAAGGCT ATCTTAGTGC TCTAAGAACT GGTTGGTATA CTAGTGTTAT AACTATAGAA | 180 |
| TTAAGTAATA TCAAGGAAAA TAAGTGTAAT GGAACAGATG CTAAGGTAAA ATTGATGAAA | 240 |
| CAAGAATTAG ATAAATATAA AAATGCTGTA ACAGAATTGC AGTTGCTCAT GCAAAGCACA | 300 |
| CCAGCAGCAA ACAATCGAGC CAGAAGAGAA CTACCAAGGT TTATGAATTA CACTCAAC | 360 |
| AATACCAAAA AAACCAATGT AACATTAAGC AAGAAAAGGA AAAGAAGATT TCTTGGTTTT | 420 |
| TTGTTAGGTG TTGGATCTGC AATCGCCAGT GGCATTGCTG TATCTAAGGT CCTGCACTTA | 480 |
| GAAGGAGAAG TGAACAAGAT CAAAAGTGCT CTACTATCCA CAAACAAGGC CGTAGTCAGC | 540 |
| TTATCAAATG GAGTTAGTGT CTTAACCAGC AAAGTGTTAG ACCTCAAAAA CTATATAGAT | 600 |
| AAACAATTGT TACCTATTGT GAATAAGCAA AGCTGCAGAA TATCAAATAT AGAAACTGTG | 660 |
| ATAGAGTTCC AACAAAAGAA CAACAGACTA CTAGAGATTA CCAGGGAATT TAGTGTTAAT | 720 |
| GCAGGTGTAA CTACACCTGT AAGCACTTAC ATGTTAACTA ATAGTGAATT ATTGTCATTA | 780 |
| ATCAATGATA TGCCTATAAC AAATGATCAG AAAAAGTTAA TGTCCAACAA TGTTCAAATA | 840 |
| GTTAGACAGC AAAGTTACTC TATCATGTCC ATAATAAAAG AGGAAGTCTT AGCATATGTA | 900 |
| GTACAATTAC CACTATATGG TGTGATAGAT ACACCTTGTT GGAAATTACA CACATCCCCT | 960 |
| CTATGTACAA CCAACACAAA AGAAGGGTCA AACATCTGTT TAACAAGAAC TGACAGAGGA | 1020 |

```
TGGTACTGTG ACAATGCAGG ATCAGTATCT TCTTCCCAC AAGCTGAAAC ATGTAAAGTT    1080

CAATCGAATC GAGTATTTTG TGACACAATG AACAGTTTAA CATTACCAAG TGAAGTAAAT    1140

CTCTGCAATG TTGACATATT CAATCCCAAA TATGATTGTA AAATTATGAC TTCAAAAACA    1200

GATGTAAGCA GCTCCGTTAT CACATCTCTA GGAGCCATTG TGTCATGCTA TGGCAAAACT    1260

AAATGTACAG CATCCAATAA AAATCGTGGA ATCATAAAGA CATTTTCTAA CGGGTGTGAT    1320

TATGTATCAA ATAAAGGGGT GGACACTGTG TCTGTAGGTA ACACATTATA TTATGTAAAT    1380

AAGCAAGAAG GCAAAAGTCT CTATGTAAAA GGTGAACCAA TAATAAATTT CTATGACCCA    1440

TTAGTATTCC CCTCTGATGA ATTTGATGCA TCAATATCTC AAGTCAATGA GAAGATTAAC    1500

CAGAGTTTAG CATTTATTCG TAAATCCGAT GAATTATTAC ATAATGTAAA TGCTGGTAAA    1560

TCAACCACAA ATATCATGAT AACTACTATA ATTATAGTGA TTATAGTAAT ATTGTTATCA    1620

TTAATTGCTG TTGGACTGCT CCTATACTGT AAGGCCAGAA GCACACCAGT CACACTAAGC    1680

AAGGATCAAC TGAGTGGTAT AAATAATATT GCATTTAGTA AC                      1722
```

(2) INFORMATION FOR SEQ ID NO:28:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (xi) SEQUENCE DESCRIPTION: SEQ ID NO:28:

```
ATGTCCAAAA ACAAGGACCA ACGCACCGCT AAGACACTAG AAAAGACCTG GACACTCTC      60

AATCATTTAT TATTCATATC ATCGGGCTTA TATAAGTTAA ATCTTAAATC TGTAGCACAA    120

ATCACATTAT CCATTCTGGC AATGATAATC TCAACTTCAC TTATAATTAC AGCCATCATA    180

TTCATAGCCT CGGCAAACCA CAAAGTCACA CTAACAACTG CAATCATACA AGATGCAACA    240

AGCCAGATCA AGAACACAAC CCCAACATAC CTCACTCAGG ATCCTCAGCT TGGAATCAGC    300

TTCTCCAATC TGTCTGAAAT TACATCACAA ACCACCACCA TACTAGCTTC AACAACACCA    360

GGAGTCAAGT CAAACCTGCA ACCCACAACA GTCAAGACTA AAAACACAAC AACAACCCAA    420

ACACAACCCA GCAAGCCCAC TACAAAACAA CGCCAAAACA AACCACCAAA CAAACCCAAT    480

AATGATTTTC ACTTCGAAGT GTTTAACTTT GTACCCTGCA GCATATGCAG CAACAATCCA    540

ACCTGCTGGG CTATCTGCAA AAGAATACCA AACAAAAAAC CAGGAAAGAA AACCACCACC    600

AAGCCTACAA AAAAACCAAC CTTCAAGACA ACCAAAAAAG ATCTCAAACC TCAAACCACT    660

AAACCAAAGG AAGTACCCAC CACCAAGCCC ACAGAAGAGC CAACCATCAA CACCACCAAA    720

ACAAACATCA CAACTACACT GCTCACCAAC AACACCACAG GAAATCCAAA ACTCACAAGT    780

CAAATGGAAA CCTTCCACTC AACCTCCTCC GAAGGCAATC TAAGCCCTTC TCAAGTCTCC    840

ACAACATCCG AGCACCCATC ACAACCCTCA TCTCCACCCA ACACAACACG CCAG          894
```

(2) INFORMATION FOR SEQ ID NO:29:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:29:

```
CGTAGTTAGT TTCCAGGACA CTATTATCCT AG                                   32
```

(2) INFORMATION FOR SEQ ID NO:30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:30:

```
TGAACTATTA CTCCTAG                                                    17
```

(2) INFORMATION FOR SEQ ID NO:31:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:31:

```
GTACCTCAAC GATTAGGAGT TTCGTTTACG TTAATGGTGT TAGGAGTGAC GTCAGTGTAA     60

AACAAAACGA AGACCAAGAT TCCAG                                           85
```

(2) INFORMATION FOR SEQ ID NO:32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:32:

```
CGTAGTTAGA TCGTGATGTA CTCCTAG                                         27
```

(2) INFORMATION FOR SEQ ID NO:33:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (xi) SEQUENCE DESCRIPTION: SEQ ID NO:33:

```
GTACGGTTGA AATTATGACG ATTAATAATG TTGTTACTAA TACCGTAGAA GGACGGTTTA     60

TCTATAGTGT TTTGATGTCG TACATCCACA TAACCAGTTG TCAGGGTTTC CCTACTTCTA    120

TAGTGTTTTG AAGCTT                                                    136
```

(2) INFORMATION FOR SEQ ID NO:34:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO:34:

```
TAGTACCTCT ATTAATTTTA CTATTGGTAG AGCGTTTATT TATTCATAAA ATGACAAAAG     60

CATTGTCAAA ACATTATTTT TTTGGATATT TATCTTAA                             98
```

(2) INFORMATION FOR SEQ ID NO:35:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (xi) SEQUENCE DESCRIPTION: SEQ ID NO:35:

TAGTACCTCT ATTAATTTTA CTATTGGTAG AGCGTTTATT TATTCATAAA ATGACAAAAG    60

CATTGTCAAA ACATTATTTT TTTGGATATT TATAAGGCCT TAAGTCTAGA CGTCGCCGGC   120

GAGGTAGATC TTCCATGGGC CCTAG                                        145

(2) INFORMATION FOR SEQ ID NO:36:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:36:

TGATTAAGGT AGTTTTCACT TTTCCGAGTA C                                  31

(2) INFORMATION FOR SEQ ID NO:37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:37:

TAAAGACACT ATAAACACGC CATATTACTA CGATATGGA                          39

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:38:

AGGACAAAAG                                                          10

What is claim is:

1. A multimeric hybrid gene encoding a chimeric protein including a protein from parainfluenza virus (PIV) and a protein from respiratory syncytial virus (RSV), comprising a nucleotide sequence encoding a fragment of a PIV-3 F protein having fusion activity or a fragment of a PIV-3 HN protein having haemagglutinin-neuramidase activity linked to a nucleotide sequence coding for a fragment of a RSV G protein having attachment activity or a RSV F protein having fusion activity, wherein said nucleotide sequences code for the respective protein lacking the hydrophobic anchor and cytoplasmic tail domains of the respective protein.

2. A multimeric hybrid gene encoding a chimeric protein including a protein from parainfluenza virus (PIV) and a protein from respiratory syncytial virus (RSV), comprising a nucleotide sequence coding for a PIV F protein or an immunogenic fragment thereof having fusion activity or a nucleotide sequence coding for a PIV HN protein or an immunogenic fragment thereof having haemagglutinin-neuramidase activity linked to a nucleotide sequence coding for a RSV G protein or an immunogenic fragment thereof having attachment activity or a nucleotide sequence coding for a RSV F protein or an immunogenic fragment thereof having fusion activity and further comprising an upstream nucleotide sequence and a downstream nucleotide sequence wherein said downstream nucleotide sequence lacks a 5'-untranslated region.

3. The hybrid gene of claim 2 wherein said upstream nucleotide sequence also lacks a 5'-untranslated region.

4. The hybrid gene of claim 2 wherein both said upstream and downstream nucleotide sequences lack a region coding for the transmembrane anchor and cytoplasmic tail of the respective protein.

5. The hybrid gene of claim 2 wherein said downstream sequence codes for a F1 subunit only of the RSV F protein.

6. The hybrid gene of claim 5 wherein said upstream nucleotide sequence codes for a PIV-3 F protein lacking its hydrophobic anchor and cytoplasmic tail domains and said downstream nucleotide sequence codes for a F1 subunit only of the RSV F protein which lacks its hydrophobic anchor and cytoplasmic tail domains.

7. The hybrid gene of claim 6 wherein said upstream nucleotide sequence lacks a 5'-untranslated region.

8. The hybrid gene of claim 2 wherein said downstream nucleotide sequence codes for a PIV-3 HN protein or a RSV G protein each lacking its hydrophobic anchor and cytoplasmic tail domains.

9. The hybrid gene of claim 8 wherein said upstream nucleotide sequence codes for a PIV-3 F or RSV F protein each lacking its hydrophobic anchor and cytoplasmic tail domains.

10. A process for the preparation of a chimeric protein including a protein from parainfluenza virus (PIV) and a protein from respiratory syncytial virus (RSV), which comprises:

isolating a first nucleotide sequence encoding a fragment of a PIV-3 F protein having fusion activity or a first nucleotide sequence encoding a fragment of a PIV-3 HN protein having haemagglutinin-neuramidase activity, isolating a second nucleotide sequence encoding a fragment of a RSV G protein having attachment activity or a second nucleotide sequence encoding a fragment of a RSV F protein having fusion activity, said first and second nucleotide sequences coding for the respective protein lacking the hydrophobic anchor and cytoplasmic tail domains of the respective protein, linking said first and second nucleotide sequences to form a multimeric hybrid gene, and expressing the multimeric hybrid gene in a eukaryotic cellular expression system.

11. A process for the preparation of a chimeric protein including a protein from parainfluenza virus (PIV) and a protein from respiratory syncytial virus (RSV), which comprises:

isolating a first nucleotide sequence coding for a PIV F protein or an immunogenic fragment thereof having fusion activity or a first nucleotide sequence coding for a PIV HN protein or an immunogenic fragment thereof having haemagglutinin-neuramidase activity, isolating a second nucleotide sequence coding for a RSV G protein or an immunogenic fragment thereof having attachment activity or a second nucleotide sequence coding for a RSV F protein or an immunogenic fragment thereof having fusion activity, wherein one of said first and second nucleotide sequences comprises an upstream nucleotide sequence and the other of said first and second nucleotide sequences comprises a downstream nucleotide sequence wherein said downstream nucleotide sequence lacks a 5'-untranslated region, linking said first and second nucleotide sequences to form a multimeric hybrid gene, and expressing the multimeric hybrid gene in a eukaryotic cellular expression system.

12. The process of claim 11 wherein said upstream nucleotide sequence also lacks a 5'-untranslated region.

13. The process of claim 11 wherein both said upstream and downstream nucleotide sequences lack a region coding for the transmembrane anchor and cytoplasmic tail of the respective protein.

14. The process of claim 11 wherein said downstream sequence codes for a F1 subunit only of the RSV F protein.

15. The process of claim 14 wherein said upstream nucleotide sequence codes for a PIV-3 F protein lacking its hydrophobic anchor and cytoplasmic tail domains and said downstream nucleotide sequence codes for a F1 subunit only of the RSV F protein which lacks its hydrophobic anchor and cytoplasmic tail domains.

16. The process of claim 15 wherein said upstream nucleotide sequence lacks a 5'-untranslated region.

17. The process of claim 11 wherein said downstream nucleotide sequence codes for a PIV-3 HN protein or a RSV G protein each lacking its hydrophobic anchor and cytoplasmic tail domains.

18. The process of claim 17 wherein said upstream nucleotide sequence codes for a PIV-3 F or RSV F protein each lacking its hydrophobic anchor and cytoplasmic tail domains.

* * * * *